(12) United States Patent
Yasu et al.

(10) Patent No.: US 11,543,525 B2
(45) Date of Patent: Jan. 3, 2023

(54) SIGNAL GENERATION APPARATUS

(71) Applicant: Sony Semiconductor Solutions Corporation, Kanagawa (JP)

(72) Inventors: Yohtaro Yasu, Kanagawa (JP); Nobuhiko Shigyo, Fukuoka (JP)

(73) Assignee: Sony Semiconductor Solutions Corporation, Kanagawa (JP)

( * ) Notice: Subject to any disclaimer, the term of this patent is extended or adjusted under 35 U.S.C. 154(b) by 263 days.

(21) Appl. No.: 16/478,961

(22) PCT Filed: Oct. 25, 2018

(86) PCT No.: PCT/JP2018/039683
§ 371 (c)(1),
(2) Date: Jul. 18, 2019

(87) PCT Pub. No.: WO2019/123828
PCT Pub. Date: Jun. 27, 2019

(65) Prior Publication Data
US 2021/0325535 A1 Oct. 21, 2021

(30) Foreign Application Priority Data
Dec. 22, 2017 (JP) .............................. JP2017-245946

(51) Int. Cl.
*G01S 17/10* (2020.01)
*G01S 17/89* (2020.01)
(Continued)

(52) U.S. Cl.
CPC ............ *G01S 17/10* (2013.01); *G01S 7/4865* (2013.01); *G01S 17/36* (2013.01); *G01S 17/89* (2013.01); *G01S 17/894* (2020.01)

(58) Field of Classification Search
CPC ................................. G01S 17/10; G01S 7/4865
See application file for complete search history.

(56) References Cited

U.S. PATENT DOCUMENTS 7,027,945 B2    4/2006  Kelly
2015/0253429 A1* 9/2015 Dorrington ........... G01S 17/894
                                                            356/5.01
(Continued)

FOREIGN PATENT DOCUMENTS

DE    44 39 298 A1    6/1996
EP    3379291 A1      9/2018
(Continued)

OTHER PUBLICATIONS

International Search Report and English translation thereof dated Jan. 29, 2019 in connection with International Application No. PCT/JP2018/039683.

(Continued)

*Primary Examiner* — Jerry T Jean Baptiste
(74) *Attorney, Agent, or Firm* — Wolf, Greenfield & Sacks, P.C.

(57) ABSTRACT

To provide a signal generation apparatus that is used in a ToF camera system especially adopting an indirect system and can suppress occurrence of erroneous distance measurement caused by distance measurement of a same target by a plurality of cameras with a simple configuration.
There is provided a signal generation apparatus including a first pulse generator configured to generate a pulse to be supplied to a light source that irradiates light upon a distance measurement target, a second pulse generator configured to generate a pulse to be supplied to a pixel that receives the light reflected by the distance measurement target, and a signal generation section configured to generate a pseudo-random signal for inverting a phase of signals to be generated by the first pulse generator and the second pulse generator.

9 Claims, 67 Drawing Sheets

(51) Int. Cl.
  *G01S 17/894* (2020.01)
  *G01S 7/4865* (2020.01)
  *G01S 17/36* (2006.01)

(56) References Cited

U.S. PATENT DOCUMENTS

| | | | |
|---|---|---|---|
| 2016/0109575 A1* | 4/2016 | Oggier | G01S 7/4915 356/51 |
| 2016/0365846 A1 | 12/2016 | Wyland | |
| 2018/0227475 A1 | 8/2018 | Kishimoto et al. | |
| 2018/0259647 A1* | 9/2018 | Takano | G01S 7/487 |
| 2020/0195825 A1* | 6/2020 | Takemoto | H04N 5/2352 |
| 2021/0286083 A1 | 9/2021 | Yasu et al. | |

FOREIGN PATENT DOCUMENTS

| | | |
|---|---|---|
| JP | 58-011340 U | 1/1983 |
| JP | 62-054189 A | 3/1987 |
| JP | 03-120127 U | 12/1991 |
| JP | 2013-076645 A | 4/2013 |
| JP | 2016-224062 A | 12/2016 |
| WO | WO 2017/061104 A1 | 4/2017 |
| WO | WO 2017/085916 A1 | 5/2017 |

OTHER PUBLICATIONS

U.S. Appl. No. 16/479,004, filed Jul. 18, 2019, Yasu et al.
International Search Report and English translation thereof dated Jan. 29, 2019 in connection with International Application No. PCT/JP2018/039702.
Extended European Search Report dated Feb. 7, 2020 in connection with European Application No. 18892632.3.
JAI: Technical Note Tips for using the Pulse Generator. Dec. 11, 2015. Retrieved from the Internet: Https://www.jai.com/uploads/documents/Technical-notes/English/TN-2015XII11-000-TechNote-PulseGenerator-tips.pdf [retrieved on Jan. 28, 2020]. pp. 1-14.
International Written Opinion and English translation thereof dated Jan. 29, 2019 in connection with International Application No. PCT/JP2018/039683.
International Written Opinion and English translation thereof dated Jan. 29, 2019 in connection with International Application No. PCT/JP2018/039702.
International Preliminary Report on Patentability and English translation thereof dated Jul. 2, 2020 in connection with International Application No. PCT/JP2018/039683.
International Preliminary Report on Patentability and English translation thereof dated Jul. 2, 2020 in connection with International Application No. PCT/JP2018/039702.
Extended European Search Report dated Apr. 17, 2020 in connection with European Application No. 18890595.4.

* cited by examiner

F I G. 4
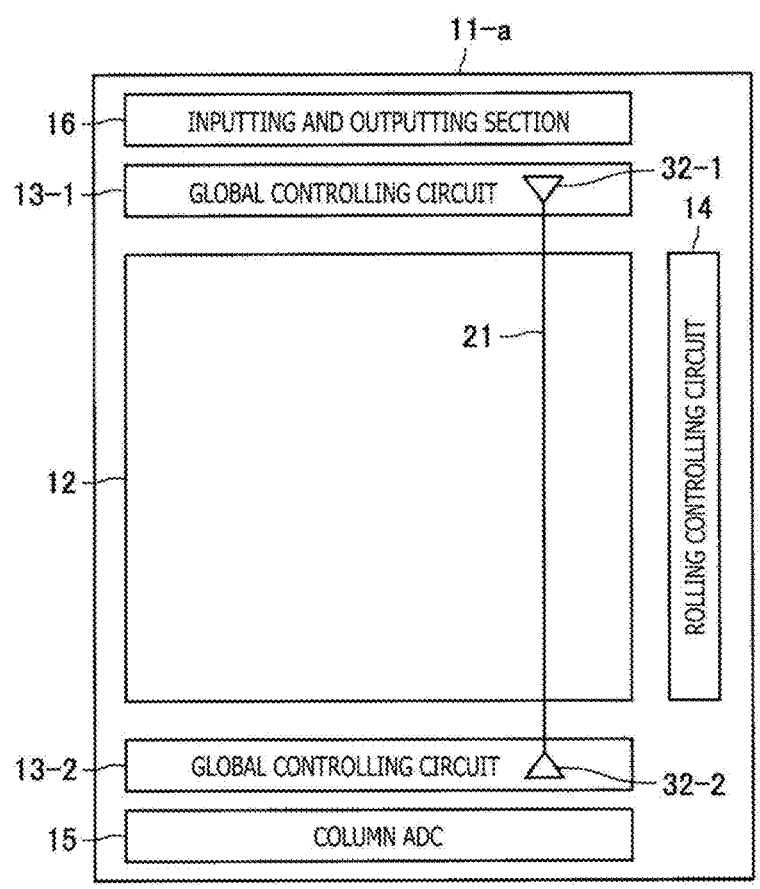

SIGNAL GENERATION APPARATUS

CROSS-REFERENCE TO RELATED APPLICATIONS

This application claims the benefit under 35 U.S.C. § 371 as a U.S. National Stage Entry of International Application No. PCT/JP2018/039683, filed in the Japanese Patent Office as a Receiving Office on Oct. 25, 2018, which claims priority to Japanese Patent Application Number JP2017-245946, filed in the Japanese Patent Office on Dec. 22, 2017, each of which is hereby incorporated by reference in its entirety.

TECHNICAL FIELD

The present disclosure relates to a signal generation apparatus.

BACKGROUND ART

A time-of-flight (ToF) camera system is a system in which a period of time after light is emitted from a light source until the light returns after it is reflected by an object is analyzed to derive information relating to the distance to the object. An example of application of the ToF camera system is a camera that can take in a three-dimensional (3D) image of a scene, namely, two-dimensional information and depth, namely, distance, information. Such a camera system as just described is utilized in many application examples in which it is necessary to decide the depth from a fixed point, namely, distance information. Generally, depth information, namely, distance information, is measured from a ToF camera system.

As the distance measurement system of the ToF camera system, a direct system of measuring the distance by directly measuring the time and an indirect system of measuring the distance indirectly from the exposure amount. The indirect system is higher in accuracy, and it is expected that a ToF camera system that adopts the indirect system spreads widely. As a literature that discloses a ToF camera system that adopts the indirect system, for example, PTL 1 and so forth are available.

CITATION LIST

Patent Literature

[PTL 1]
Japanese Patent Laid-Open No. 2016-224062

SUMMARY

Technical Problem

In an active distance measurement system, light is emitted from a light source and light reflected by an object of the distance measurement target is detected to perform distance measurement to the distance measurement target. In this active distance measurement system, if a plurality of cameras measure the distance to a same target, then signals of them mix up, which gives rise to erroneous distance measurement.

Therefore, the present disclosure proposes a signal generation apparatus that is used in a ToF camera system especially adopting the indirect system and is novel and improved in that it can suppress occurrence of erroneous distance measurement caused by distance measurement of a same target by a plurality of cameras with a simple configuration.

Solution to Problem

According to the present disclosure, there is provided a signal generation apparatus including a first pulse generator configured to generate a pulse to be supplied to a light source that irradiates light upon a distance measurement target, a second pulse generator configured to generate a pulse to be supplied to a pixel that receives the light reflected by the distance measurement target, and a signal selection section configured to select and output a duty of a signal to be outputted from the first pulse generator from between a first duty and a second duty different from the first duty.

Advantageous Effects of Invention

As described above, according to the present disclosure, the signal generation apparatus that is used in a ToF camera system especially adopting the indirect system and is novel and improved in that it can suppress occurrence of erroneous distance measurement caused by distance measurement of a same target by a plurality of cameras with a simple configuration.

It is to be noted that the advantageous effect described above is not necessarily restrictive, and some advantageous effects indicated in the present specification or other advantageous effects that can be recognized from the present specification may be applicable together with the advantageous effect described above or in place of the advantageous effect described above.

BRIEF DESCRIPTION OF DRAWINGS

FIG. 4 is a block diagram depicting a first modification of a sensor chip of FIG. 1.

DESCRIPTION OF EMBODIMENTS

Figure 1:
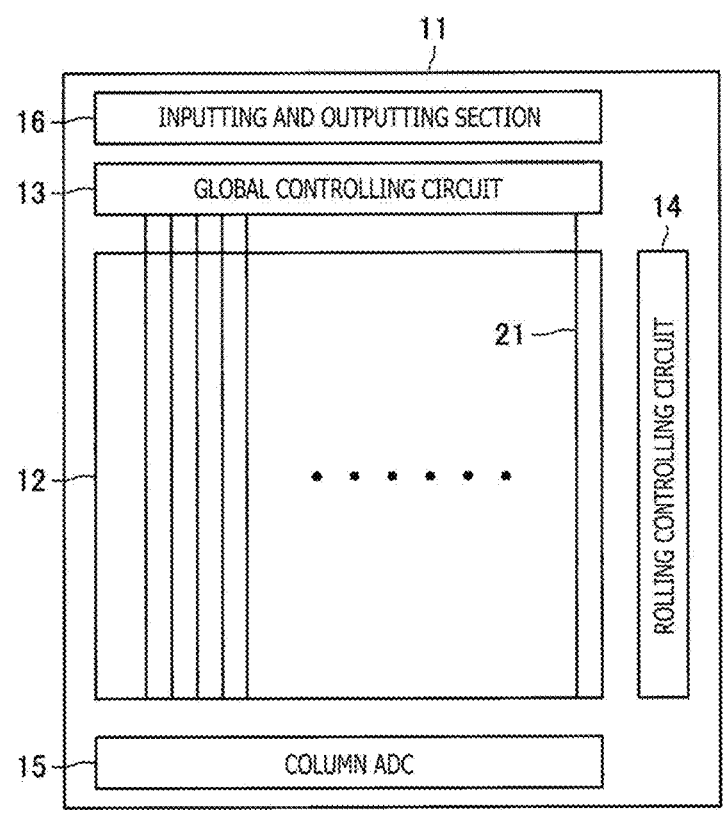
FIG. 1 is a block diagram depicting a configuration example of a first embodiment of a sensor chip to which the present technology is applied.

In the following, a preferred embodiment of the present disclosure is described in detail with reference to the accompanying drawings. It is to be noted that, in the present specification and drawings, components having substantially same functional configurations are denoted by like reference characters and overlapping description of them is omitted.

It is to be noted that the description is given in the following order.

1. Embodiment of Present Disclosure
1.1. Overview
1.2. Configuration Example of Sensor Chip
1.3. Particular Configuration Example of Distance Image Sensor
2. Summary <1. Embodiment of Present Disclosure>
[1.1. Overview]

First, an overview of the embodiment of the present disclosure is described.

A ToF camera system is a system in which a period of time after light is emitted from a light source until the light returns after it is reflected by an object is analyzed to derive information relating to the distance to the object. An example of application of the ToF camera system is a camera that can take in a three-dimensional (3D) image of a scene, namely, two-dimensional information and depth, namely, distance, information. Such a camera system as just described is utilized in many application examples in which it is necessary to decide the depth from a fixed point, namely, distance information. Generally, depth information, namely, distance information, is measured from a ToF camera system.

As the distance measurement system of the ToF camera system, a direct system of measuring the distance by directly measuring the time and an indirect system of measuring the distance indirectly from the exposure amount. The indirect system is higher in accuracy, and it is expected that a ToF camera system that adopts the indirect system spreads widely.

The disclosing person of the present case has improved a ToF camera system that adopts the conventional direct method and has conceived a ToF camera system that adopts the indirect system and a configuration that is used in the ToF camera system, which can increase the accuracy in distance measurement with a simple configuration as described below.

[1.2. Configuration Example of Sensor Chip]
<First Configuration Example of Sensor Chip>

FIG. 1 is a block diagram depicting a configuration example of a first embodiment of a sensor chip to which the present technology is applied.

As depicted in FIG. 1, the sensor chip 11 is configured including a pixel array section 12, a global controlling circuit 13, a rolling controlling circuit 14, a column ADC (Analog-to-Digital Converter) 15 and an inputting and outputting section 16, which are disposed on a semiconductor substrate.

The pixel array section 12 is a rectangular region in which various sensor elements according to functions of the sensor chip 11, for example, photoelectric conversion elements that perform photoelectric conversion of light, are disposed in an array. In the example depicted in FIG. 1, the pixel array section 12 is a horizontally elongated rectangular region having a long side extending in the horizontal direction and a short side extending in the vertical direction.

The global controlling circuit 13 is a control circuit that outputs a global controlling signal for controlling the plurality of sensor elements disposed in the pixel array section 12 such that they are driven all at once (simultaneously) at a substantially same timing. In the configuration example of FIG. 1, the global controlling circuit 13 is disposed on the upper side of the pixel array section 12 such that the longitudinal direction thereof extends along a long side of the pixel array section 12. Accordingly, in the sensor chip 11, a control line 21 for supplying the global controlling signal outputted from the global controlling circuit 13 to the sensor elements of the pixel array section 12 is disposed in the upward and downward direction of the pixel array section 12 for each column of the sensor elements disposed in a matrix in the pixel array section 12.

The rolling controlling circuit 14 is a control circuit that outputs rolling controlling signals for controlling the plurality of sensor elements disposed in the pixel array section 12 such that the sensor elements are successively (sequentially) driven in order for each row. In the configuration example depicted in FIG. 1, the rolling controlling circuit 14 is disposed on the right side of the pixel array section 12 such that the longitudinal direction thereof extends along a short side of the pixel array section 12.

The column ADC 15 converts analog sensor signals outputted from the sensor elements of the pixel array section 12 to digital values with AD (Analog-to-Digital)) in parallel for the individual columns. At this time, the column ADC 15 can remove reset noise included in the sensor signals, for example, by performing a CDS (Correlated Double Sampling: correlated double sampling) process for the sensor signals.

The inputting and outputting section 16 has provided thereon terminals for performing inputting and outputting between the sensor chip 11 and an external circuit, and for example, power necessary for driving the global controlling circuit 13 is inputted to the sensor chip 11, for example, through the inputting and outputting section 16. In the configuration example depicted in FIG. 1, the inputting and outputting section 16 is disposed along the global controlling circuit 13 such that it is positioned adjacent the global controlling circuit 13. For example, since the global controlling circuit 13 has high power consumption, in order to reduce the influence of an IR drop (voltage drop), preferably the inputting and outputting section 16 is disposed in the proximity of the global controlling circuit 13.

The sensor chip 11 is configured in this manner, and a layout in which the global controlling circuit 13 is disposed so as to extend along a long side of the pixel array section 12 is adopted. Consequently, the distance from the global controlling circuit 13 to a sensor element disposed at the remote end of the control line 21 (the lower end in the example of FIG. 1) can be made shorter than that in an alternative layout in which the global controlling circuit 13 is disposed so as to extend along a short side of the pixel array section 12.

Accordingly, since the sensor chip 11 can improve the delay amount and the slew rate that occur with a global controlling signal outputted from the global controlling circuit 13, it can perform control for the sensor elements at a high speed. Especially, in the case where the sensor chip 11 is an image sensor that performs global shutter driving, high speed control of a transfer signal or a reset signal to be supplied to the pixels, an overflow gate signal and so forth becomes possible. On the other hand, in the case where the sensor chip 11 is a ToF sensor, high speed control of a MIX signal becomes possible.

For example, in a ToF sensor, a fluorescence detection sensor or the like, if the slew rate of a global controlling signal or the delay amount of a global controlling signal, which occurs in accordance with the distance from a driving element, or the like differs for each sensor element, then this gives rise to a detection error. In contrast, since the sensor chip 11 can improve the delay amount and the slew rage that occur in the global controlling signal as described above, such a detection error as described above can be suppressed.

Further, in the case where the sensor chip 11 is a ToF sensor, a fluorescence detection sensor or the like, not only such a number of times of on/off control as may exceed 100 times is required for an exposure period but also the current consumption increases because the toggle frequency is high. In contrast, in the sensor chip 11, the inputting and outputting section 16 can be disposed in the proximity of the global controlling circuit 13 as described above such that an independent wiring line can be provided for the power supply.

Further, while, in the sensor chip 11, the global controlling circuit 13 frequently operates during an exposure period, the rolling controlling circuit 14 remains stopping. On the other hand, in the sensor chip 11, while the rolling controlling circuit 14 operates within a reading out period, the global controlling circuit 13 frequently is stopping. Therefore, in the sensor chip 11, it is demanded to control the global controlling circuit 13 and the rolling controlling circuit 14 independently of each other. Further, in the sensor chip 11, in order to secure in-plane synchronization, it is general to adopt such a clock tree structure depicted in FIG. 2C as hereinafter described, preferably the global controlling circuit 13 is disposed independently of the rolling controlling circuit 14.

Accordingly, in the case where higher speed control is demanded as in the sensor chip 11, better control can be anticipated by adopting the layout in which the global controlling circuit 13 and the rolling controlling circuit 14 are individually and independently of each other. It is to be noted, if the global controlling circuit 13 and the rolling controlling circuit 14 are disposed individually and independently of each other, then any one of a layout in which they extend along a same direction and another layout in which they extend orthogonally to each other may be adopted.

It is to be noted that, although, in the description of the present embodiment, it is described that the upper side in each figure is the upper side of the pixel array section 12 and the lower side in each figure is the lower side of the pixel array section 12 in accordance with the configuration example depicted, if, for example, the global controlling circuit 13 is disposed so as to extend along a long side of the pixel array section 12, then similar working effects can be achieved on whichever one of the upper side and the lower side the global controlling circuit 13 is disposed. Further, this similarly applies also to the pixel array section 12 and the column ADC 15.

A configuration of the global controlling circuit 13 is described with reference to FIG. 2.

Figure 2:
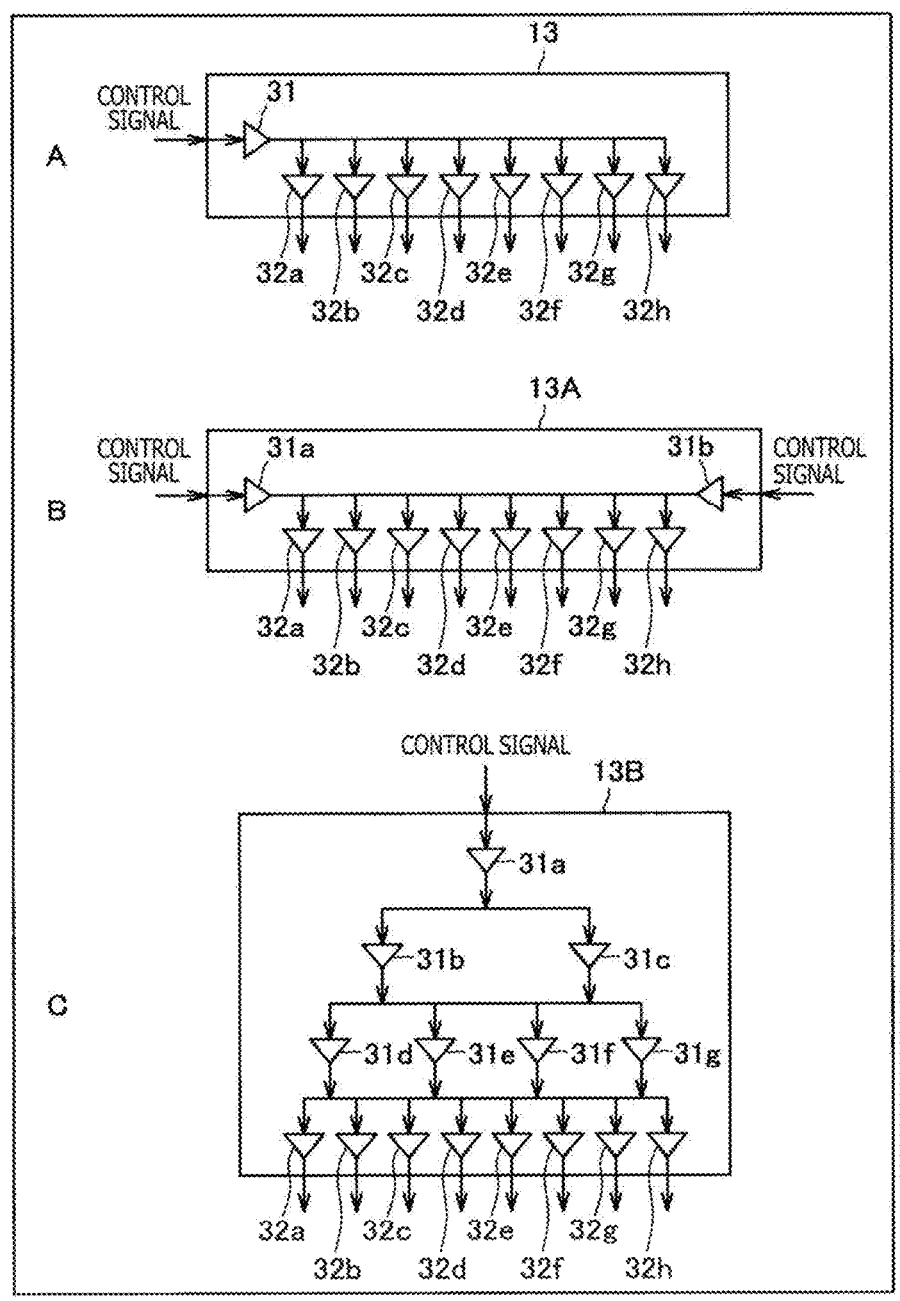
FIG. 2 is a view depicting a configuration example of a global controlling circuit.

FIG. 2A depicts a first configuration example of the global controlling circuit 13; FIG. 2B depicts a second configuration example of the global controlling circuit 13; and FIG. 2C depicts a third configuration example of the global controlling circuit 13. It is to be noted that, although the global controlling circuit 13 is configured such that it simultaneously outputs global controlling signals in accordance with the number of columns of sensor elements disposed in the pixel array section 12, in FIG. 2, as part of the configuration, a configuration that outputs eight global controlling signals at the same time is schematically depicted.

The global controlling circuit 13 depicted in FIG. 2A is configured including one internal buffer 31 and eight driving elements 32a to 32h.

As depicted in FIG. 2A, the global controlling circuit 13 has such a connection configuration that the internal buffer 31 is connected to one end of an internal wiring line provided along the longitudinal direction and the driving elements 32a to 32h are connected to the internal wiring line toward one direction according to the positions of the control lines 21. Accordingly, a global controlling signal inputted to the global controlling circuit 13 is supplied from one end side of the internal wiring line (in the example of FIG. 2, the left side) to the driving elements 32a to 32h through the internal buffer 31 and is simultaneously outputted to the control lines 21 individually connected to the driving elements 32a to 32h.

The global controlling circuit 13A depicted in FIG. 2B is configured including two internal buffers 31a and 31b and eight driving elements 32a to 32h.

As depicted in FIG. 2B, the global controlling circuit 13A has such a connection configuration that the internal buffers 31a and 31b are connected to the opposite ends of an internal wiring line provided along the longitudinal direction of the global controlling circuit 13A and the driving elements 32a to 32h are connected to the internal wiring line toward one direction according to the positions of the control lines 21 of FIG. 1. Accordingly, a global controlling signal inputted to the global controlling circuit 13A is supplied from the opposite ends of the internal wiring line through the internal buffers 31a and 31b to the driving elements 32a to 32h and is simultaneously outputted to the control lines 21 individually connected to the driving elements 32a to 32h.

The global controlling circuit 13B depicted in FIG. 2C is configured including seven internal buffers 31a to 31g and eight driving elements 32a to 32h.

As depicted in FIG. 2C, the global controlling circuit 13B has such a connection configuration that a clock tree structure is configured from the internal buffers 31a to 31g and, in the final stage, it is connected to the driving elements 32a to 32h disposed along one direction according to the positions of the control lines 21. For example, the clock tree structure is such a structure that a structure that, in the first stage, an output of one internal buffer 31 is inputted to two internal buffers 31 and, in the second state, inputs of the two internal buffers 31 are inputted to four internal buffers 31 is repeated in a plurality of stages. Accordingly, a global controlling signal inputted to the global controlling circuit 13B is supplied to the driving elements 32a to 32h through the clock tree structure configured from the internal buffers 31a to 31g and is simultaneously outputted to the control lines 21 connected to the driving elements 32a to 32h.

The global controlling circuit 13B having such a configuration as described above can avoid occurrence of a delay between the driving elements 32a to 32h and can ensure in-plane uniformity, for example, in comparison with the global controlling circuits 13 and 13A. In other words, it is preferable to adopt the global controlling circuit 13B in an application in which synchronization is requested strongly over a direction in which the driving elements 32 are lined up.

A configuration of the rolling controlling circuit 14 is described with reference to FIG. 3.

Figure 3:
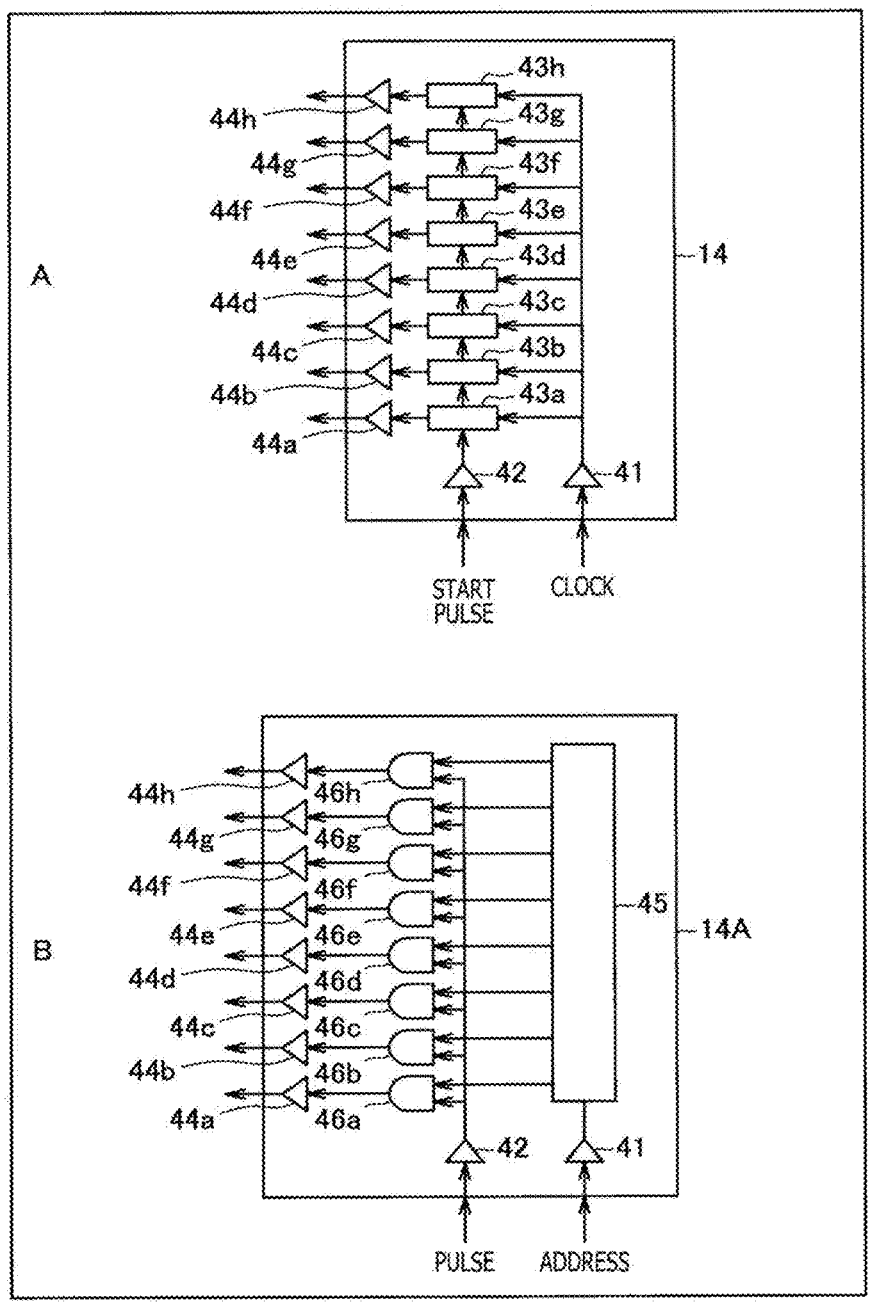
FIG. 3 is a view depicting a configuration of a rolling controlling circuit.

FIG. 3A depicts a first configuration example of the rolling controlling circuit 14, and FIG. 3B depicts a second configuration example of the rolling controlling circuit 14. It is to be noted that, although the rolling controlling circuit 14 is configured such that it sequentially outputs rolling controlling signals according to the row number of the sensor elements disposed in the pixel array section 12, in FIG. 3, as part of the configuration, a configuration that outputs eight rolling controlling signals sequentially is schematically depicted.

The rolling controlling circuit 14 depicted in FIG. 3A adopts a shift register system and is configured including two internal buffers 41 and 42, eight registers 43a to 43h and eight driving elements 44a to 44h. It is to be noted that, although the configuration example in which two internal buffers 41 and 42 are disposed is depicted for simplification, a configuration may otherwise be adopted in which a plurality of internal buffers are disposed according to wiring line lengths of the internal buffers.

As depicted in FIG. 3A, the rolling controlling circuit 14 has such a connection configuration that the internal buffer 41 is connected to one end of an internal wiring line provided along the longitudinal direction and the registers 43a to 43h are connected to the internal wiring line according to the positions of the rows of the sensor elements disposed in the pixel array section 12. Further, the rolling controlling circuit 14 has such a connection configuration that the internal buffer 42 is connected to the register 43a and the registers 43a to 43h are connected sequentially and besides the driving elements 44a to 44h are connected to the registers 43a to 43h, respectively.

Accordingly, in the rolling controlling circuit 14, a start pulse supplied to the register 43a through the internal buffer 42 is sequentially shifted to the registers 43a to 43h in accordance with a clock supplied through the internal buffer 41 and is sequentially outputted as rolling controlling signals from the driving elements 44a to 44h connected to the registers 43a to 43h, respectively.

The rolling controlling circuit 14A depicted in FIG. 3B adopts a decoder system and is configured including two internal buffers 41 and 42, a decoder 45, eight AND gates 46a to 46h and eight driving elements 44a to 44h. It is to be noted that, for the decoder 45, any one of a decoder of a type that includes a latch and a decoder of another type that does not include a latch may be used. For example, in the case where the decoder 45 is of the type that latches a signal, a system by which addresses are sent at once, another system by which addresses are sent divisionally or the like can be adopted.

As depicted in FIG. 3B, in the rolling controlling circuit 14A, the internal buffer 41 is connected to the decoder 45, and the internal buffer 42 is connected to an input terminal of the AND gates 46a to 46h and the decoder 45 is connected to an input terminal of the AND gates 46a to 46h for each row. Further, the rolling controlling circuit 14A has a connection configuration in which output terminals of the AND gates 46a to 46h are connected to the driving elements 44a to 44h, respectively.

Accordingly, in the rolling controlling circuit 14A, a pulse supplied to the AND gates 46a to 46h through the internal buffer 42 is sequentially outputted as rolling controlling signals from the driving elements 44a to 44h of rows designated by addresses supplied to the decoder 45 through the internal buffer 41.

As described with reference to FIGS. 2 and 3, the global controlling circuit 13 and the rolling controlling circuit 14 have circuit configurations different from each other.

FIG. 4 is a block diagram depicting a first modification of the sensor chip 11 depicted in FIG. 1. It is to be noted that, from among blocks configuring the sensor chip 11-a depicted in FIG. 4, components common to those of the sensor chip 11 of FIG. 1 are denoted by like reference characters, and detailed description of them is omitted.

In particular, as depicted in FIG. 4, the sensor chip 11-a has a configuration common to the sensor chip 11 of FIG. 1 in terms of the disposition of the pixel array section 12, rolling controlling circuit 14, column ADC 15 and inputting and outputting section 16.

Figure 11:
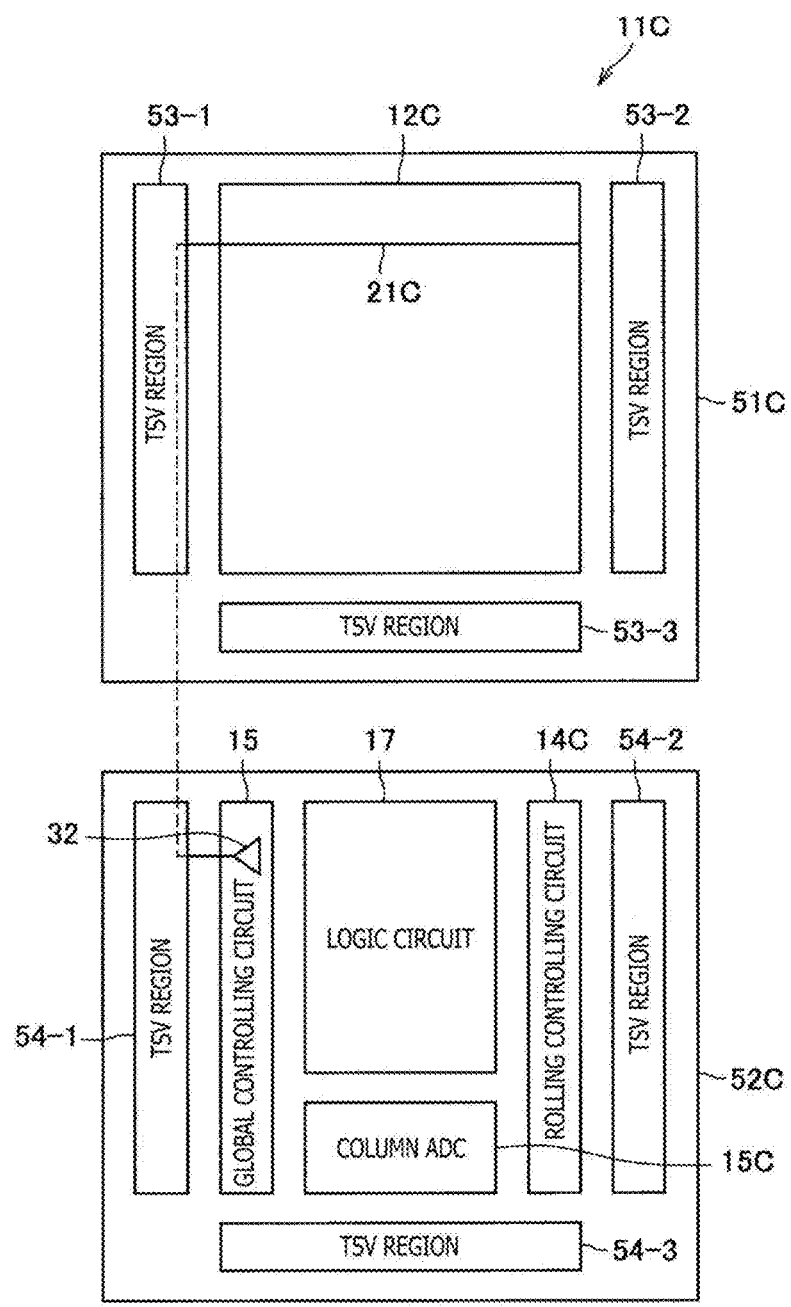
FIG. 11 is a block diagram depicting a configuration example of a fourth embodiment of the sensor chip.

Meanwhile, the sensor chip 11-a has a configuration different from that of the sensor chip 11 of FIG. 11 in that two global controlling circuits 13-1 and 13-2 are disposed so as to extend along the upper side and the lower side of the pixel array section 12, respectively, and the driving elements 32-1 and 32-2 are connected to the opposite ends of the control line 21. In particular, the sensor chip 11-a is configured such that the driving element 32-1 included in the global controlling circuit 13-1 supplies a global controlling signal from the upper end of the control line 21 and the driving element 32-2 included in the global controlling circuit 13-2 supplies a global controlling signal from the lower end of the control line 21.

The sensor chip 11-a configured in this manner can suppress a skew between the two driving element 32-1 and driving element 32-2 and can eliminate a dispersion in delay time that occurs in global controlling signals propagated along the control line 21. Consequently, in the sensor chip 11-a, control for the sensor elements can be performed at a higher speed. It is to be noted that, in the sensor chip 11-a, it is necessary to perform the control such that the delay difference in outputting of global controlling signals is avoided from becoming great such that through current may not be generated.

Figure 5:
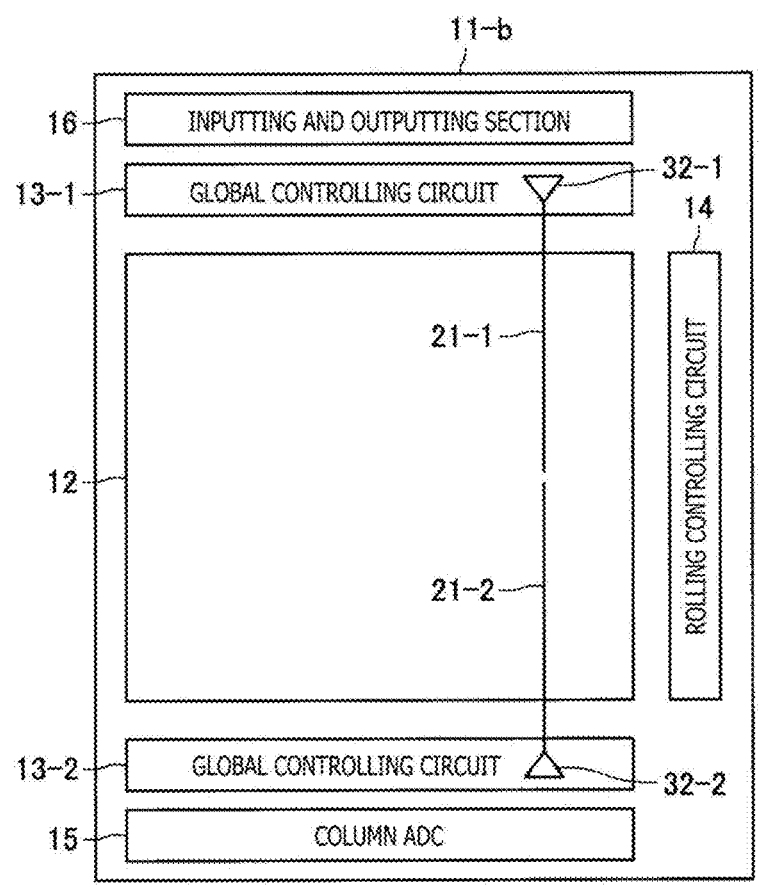
FIG. 5 is a block diagram depicting a second modification of the sensor chip of FIG. 1.

FIG. 5 is a block diagram depicting a second modification of the sensor chip 11 depicted in FIG. 1. It is to be noted that, from among blocks configuring the sensor chip 11-b depicted in FIG. 5, components common to those of the sensor chip 11 of FIG. 1 are denoted by like reference characters, and detailed description of them is omitted.

In particular, as depicted in FIG. 5, the sensor chip 11-b is configured commonly to the sensor chip 11 of FIG. 1 in terms of the disposition of the sensor chip 11-b, pixel array section 12, rolling controlling circuit 14, column ADC 15 and inputting and outputting section 16.

On the other hand, the sensor chip 11-b has a different configuration from that of the sensor chip 11 of FIG. 1 in that the two global controlling circuits 13-1 and 13-2 are disposed so as to extend along the upper side and the lower side of the pixel array section 12, respectively, and the two control lines 21-1 and 21-2 are disposed such that they are separate at the center of a column of the sensor elements disposed in a matrix in the pixel array section 12. Further, in the sensor chip 11-b, the driving element 32-1 is connected to an upper end of the control line 21-1, and the driving element 32-2 is connected to a lower end of the control line 21-2.

Accordingly, the sensor chip 11-b is configured such that, to the sensor elements disposed on the upper side with respect to the center of the pixel array section 12, the driving element 32-1 included in the global controlling circuit 13-1 supplies a global controlling signal from the upper end of the control line 21-1. Further, the sensor chip 11-b is configured such that, to the sensor elements disposed on the lower side with respect to the center of the pixel array section 12, the driving element 32-2 included in the global controlling circuit 13-2 supplies a global controlling signal from the lower end of the control line 21-2.

According to the sensor chip 11-b configured in this manner, the distance from the driving element 32-1 to a sensor element disposed at the remote end (in the example of FIG. 5, the lower end) of the control line 21-1 and the distance from the driving element 32-2 to a sensor element disposed at the remote end (in the example of FIG. 5, the upper end) of the control line 21-2 can made shorter, for example, than that in the sensor chip 11 of FIG. 1. Consequently, the sensor chip 11-*b* can perform control for the sensor elements at a further higher speed because the delay amount and the slew rate occurring with global controlling signals outputted from the global controlling circuits 13-1 and 13-2 can be further reduced.

<Second Configuration Example of Sensor Chip>

A second embodiment of a sensor chip to which the present technology is applied is described with reference to FIG. 6. It is to be noted that, from among blocks configuring the sensor chip 11A depicted in FIG. 6, components common to those of the sensor chip 11 of FIG. 1 are denoted by like reference characters, and detailed description of them is omitted.

Figure 6:
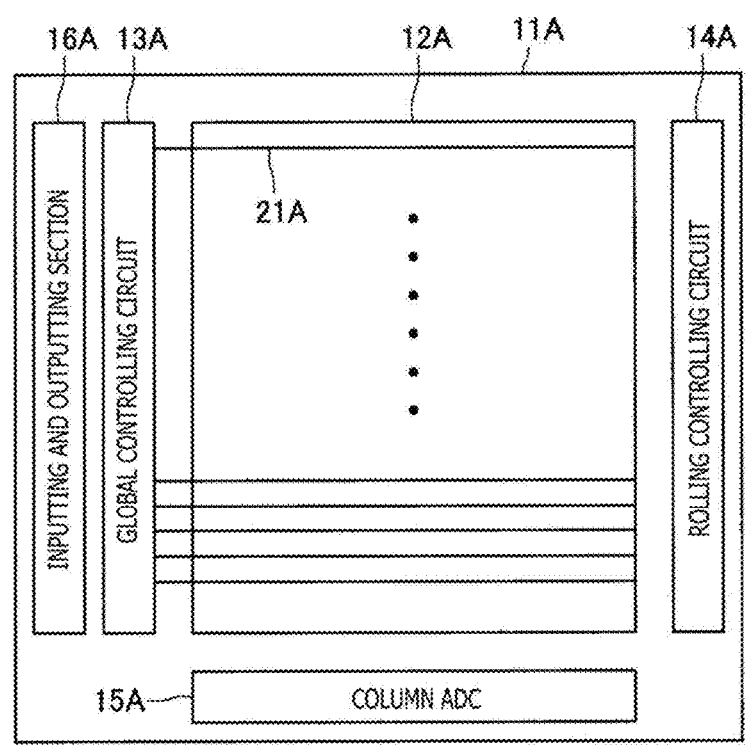
FIG. 6 is a block diagram depicting a configuration example of a second embodiment of the sensor chip.

As depicted in FIG. 6, the sensor chip 11A is configured such that a pixel array section 12A, a global controlling circuit 13A, a rolling controlling circuit 14A, a column ADC 15A and an inputting and outputting section 16A are disposed on a semiconductor substrate.

The sensor chip 11A is different in configuration from the sensor chip 11 of FIG. 1 in that the pixel array section 12A is a vertically elongated rectangular area in which the longer sides are provided to extend in the vertical direction and the shorter sides are provided to extend in the horizontal direction. Accordingly, in the sensor chip 11A, the global controlling circuit 13A and the inputting and outputting section 16A are disposed on the left side of the pixel array section 12A so as to extend along a long side of the pixel array section 12A. With this, a control line 21A is disposed, for each row of the sensor elements disposed in a matrix in the pixel array section 12A, toward the leftward and rightward direction of the pixel array section 12A.

Further, in the sensor chip 11A, the rolling controlling circuit 14A is disposed on the right side of the pixel array section 12A (on the side opposing to the global controlling circuit 13A) so as to extend along a long side of the pixel array section 12A. It is to be noted that, although the global controlling circuit 13A and the pixel array section 12A may be disposed on the same side with respect to the pixel array section 12A, in this case, since it is supposed that the wiring line length of any one of them becomes longer, it is preferable to adopt such arrangement as depicted in FIG. 6.

Further, in the sensor chip 11A, the column ADC 15A is disposed on the lower side of the pixel array section 12A so as to extend along a short side of the pixel array section 12A. The reason why the column ADC 15A is disposed in a direction orthogonal to the rolling controlling circuit 14A in this manner is that it is necessary to turn on the sensor elements connected to one AD converter one by one, and such a layout that individual wiring lines overlap with each other is avoided.

According to the sensor chip 11A configured in this manner, the wiring line length of the control line 21A can be reduced by the layout in which the global controlling circuit 13A is disposed so as to extend along a long side of the pixel array section 12A similarly to the sensor chip 11 of FIG. 1. Accordingly, the sensor chip 11A can perform control for the sensor elements at a higher speed similarly to the sensor chip 11 of FIG. 1.

<Third Configuration Example of Sensor Chip>

A third embodiment of a sensor chip to which the present technology is applied is described with reference to FIGS. 7 to 10. It is to be noted that, from among blocks configuring the sensor chip 11B depicted in FIGS. 7 to 10, components common to those of the sensor chip 11 of FIG. 1 are denoted by like reference characters, and detailed description of them is omitted.

Figure 7:
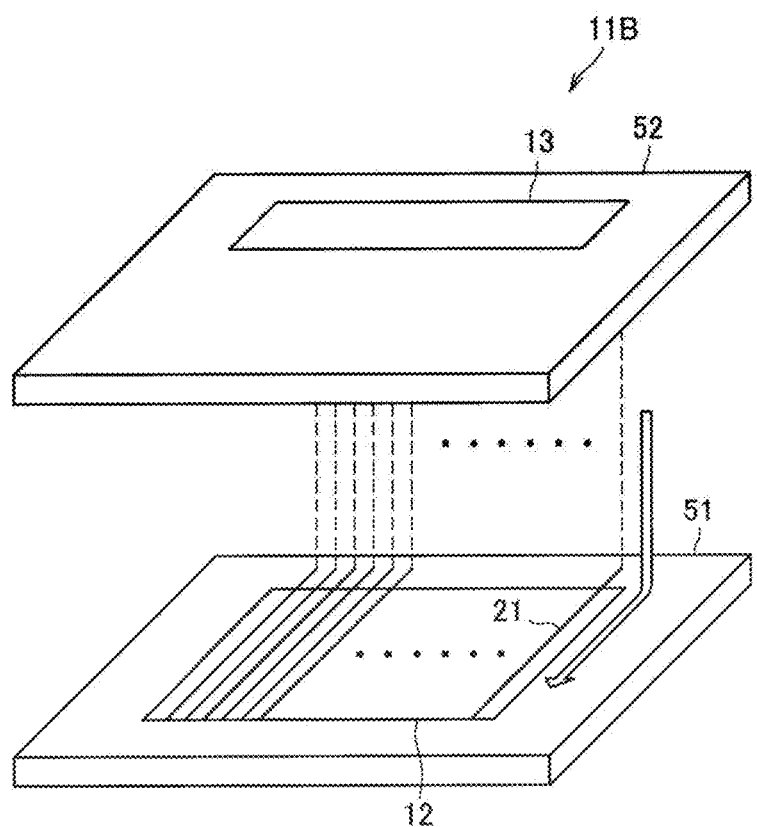
FIG. 7 is a perspective view depicting a configuration example of a third embodiment of the sensor chip.
Figure 8:
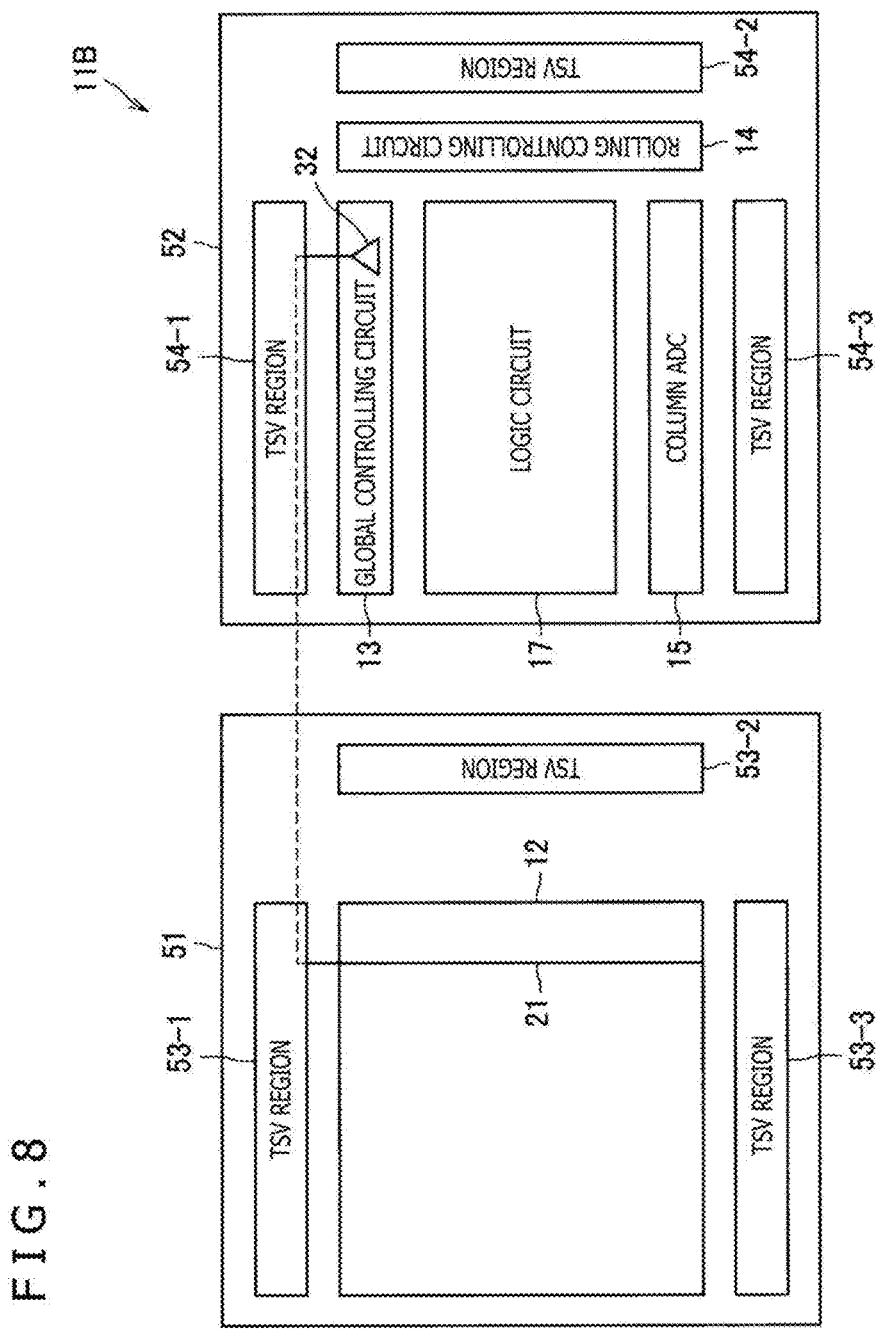
FIG. 8 is a block diagram depicting the configuration example of the third embodiment of the sensor chip.

FIG. 7 depicts a perspective view of the sensor chip 11B, and FIG. 8 depicts a block diagram of the sensor chip 11B.

As depicted in FIG. 7, the sensor chip 11B has a stacked structure in which a sensor substrate 51 on which a pixel array section 12 is formed and a logic substrate 52 on which a global controlling circuit 13 is formed are stacked. Further, the sensor chip 11B has such a connection structure that, in a peripheral region of the sensor chip 11B in which it does not overlap with the pixel array section 12 as viewed in plan, control lines 21 of the sensor substrate 51 and the global controlling circuit 13 of the logic substrate 52 are connected to each other. In particular, in the example depicted in FIG. 7, in the sensor chip 11B, a plurality of control lines 21 disposed along a column direction of the sensor elements disposed in a matrix in the pixel array section 12 are connected to the global controlling circuit 13 side on the upper side of the sensor substrate 51.

Accordingly, in the sensor chip 11B, a global controlling signal outputted from the global controlling circuit 13 is supplied to the sensor elements of the pixel array section 12 from the upper side of the sensor substrate 51 as indicated by a void arrow mark in FIG. 7. At this time, the global controlling circuit 13 is configured such that it is disposed such that the longitudinal direction thereof extends along a long side of the pixel array section 12 and the sensor chip 11B has the shortest distance from the global controlling circuit 13B to the sensor elements of the pixel array section 12.

A configuration of the sensor chip 11B is described further with reference to FIG. 8.

The sensor substrate 51 has a pixel array section 12 and TSV (Through Silicon Via) regions 53-1 to 53-3 disposed thereon. The logic substrate 52 has a global controlling circuit 13, a rolling controlling circuit 14, a column ADC 15, a logic circuit 17 and TSV regions 54-1 to 54-3 disposed thereon. For example, in the sensor chip 11B, a sensor signal outputted from each sensor element of the pixel array section 12 is AD converted by the column ADC 15 and is subjected to various signal processes by the logic circuit 17, whereafter it is outputted to the outside.

The TSV regions 53-1 to 53-3 and the TSV regions 54-1 to 54-3 are regions in which through-electrodes for electrically connecting the sensor substrate 51 and the logic substrate 52 to each other are formed, and a through electrode is disposed for each control line 21. Accordingly, the TSV regions 53-1 to 53-3 and the TSV regions 54-1 to 54-3 are disposed such that they overlap with each other when the sensor substrate 51 and the logic substrate 52 are stacked. It is to be noted that not only through electrodes can be used for connection in the TSV regions 54, but also, for example, micro bump or copper (Cu—Cu) connection can be utilized.

According to the sensor chip 11B configured in this manner, the wiring line length of the control line 21 can be made short by the layout in which the global controlling circuit 13 is disposed so as to extend along a long side of the pixel array section 12 similarly to the sensor chip 11 of FIG. 1. Accordingly, the sensor chip 11B can perform control for the sensor elements at a higher speed similarly to the sensor chip 11 of FIG. 1.

Figure 9:
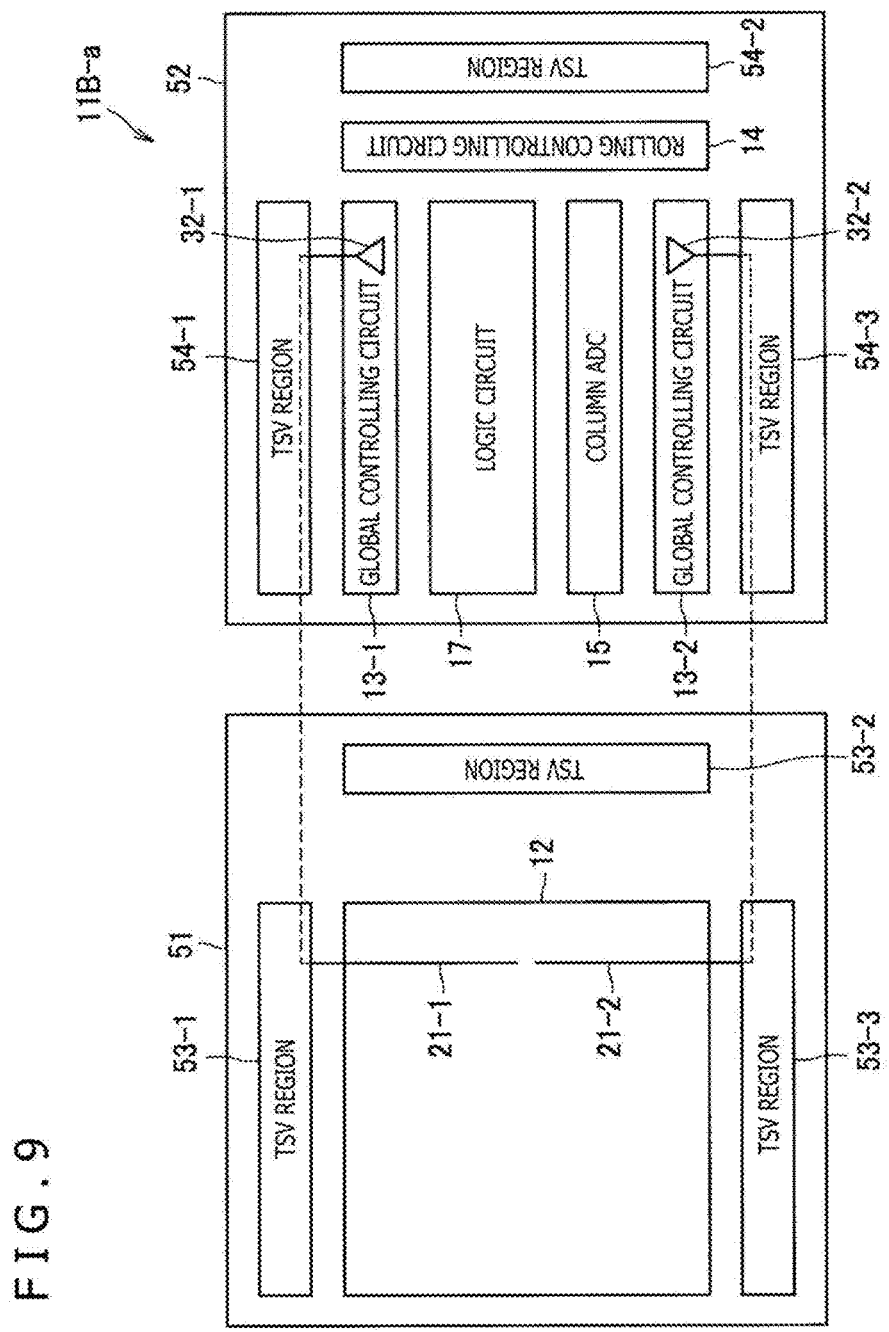
FIG. 9 is a block diagram depicting a first modification of the sensor chip of FIG. 8.

FIG. 9 is a block diagram depicting a first modification of the sensor chip 11B depicted in FIG. 8. It is to be noted that, from among blocks configuring the sensor chip 11B-*a* depicted in FIG. 9, components common to those of the sensor chip 11B of FIG. 8 are denoted by like reference characters, and detailed description of them is omitted.

As depicted in FIG. 9, in particular, the sensor chip 11B-a is configured commonly to the sensor chip 11B of FIG. 8 in that it has such a stacked structure that the sensor substrate 51 on which the pixel array section 12 is formed and the logic substrate 52 on which the global controlling circuit 13 is formed are stacked.

On the other hand, the sensor chip 11B-a is different in configuration from the sensor chip 11B of FIG. 8 in that the two global controlling circuits 13-1 and 13-2 are disposed on the logic substrate 52 so as to extend along the upper side and the lower side of the pixel array section 12, respectively, and two control lines 21-1 and 21-2 are disposed such that they are separate from each other at the center of the columns of the sensor elements disposed in a matrix on the pixel array section 12.

In particular, in the sensor chip 11B-a, the driving element 32-1 is connected to an upper end of the control line 21-1 and the driving element 32-2 is connected to the lower end of the control line 21-2 similarly as in the sensor chip 11-*b* depicted in FIG. 5. Accordingly, the sensor chip 11B-a is configured such that, to the sensor elements disposed on the upper side with respect to the center of the pixel array section 12, the driving element 32-1 included in the global controlling circuit 13-1 supplies a global controlling signal from the upper end of the control line 21-1. Further, the sensor chip 11B-a is configured such that, to the sensor elements disposed on the lower side with respect to the center of the pixel array section 12, the driving element 32-2 included in the global controlling circuit 13-2 supplies a global controlling signal from the lower end of the control line 21-2.

In the sensor chip 11B-a configured in such a manner as described above, the distance from the driving element 32-1 to a sensor element disposed at the remote end (in the example of FIG. 9, at the lower end) of the control line 21-1 and the distance from the driving element 32-2 to a sensor element disposed at the remote end (in the example of FIG. 9, at the upper end) of the control line 21-2 can be made shorter, for example, than that in the sensor chip 11B of FIG. 8. Consequently, the sensor chip 11B-a can perform control for the sensor elements at a higher speed because the delay amount and the slew rate occurring with global signals outputted from the global controlling circuits 13-1 and 13-2 can be further reduced.

Figure 10:
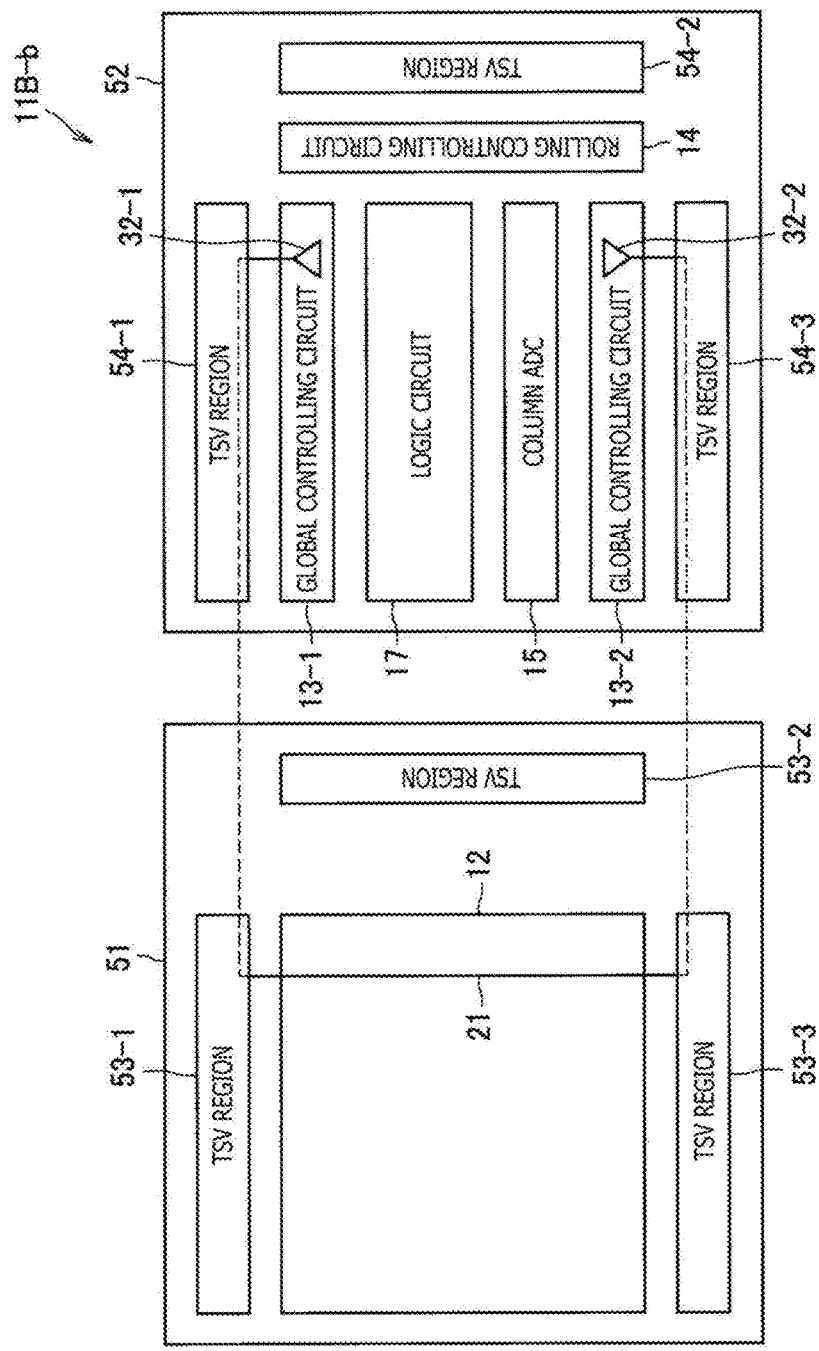
FIG. 10 is a block diagram depicting a second modification of the sensor chip of FIG. 8.

FIG. 10 is a block diagram depicting a second modification of the sensor chip 11B depicted in FIG. 8. It is to be noted that, from among blocks configuring the sensor chip 11B-b depicted in FIG. 10, components common to those of the sensor chip 11B of FIG. 8 are denoted by like reference characters, and detailed description of them is omitted.

In particular, as depicted in FIG. 10, the sensor chip 11B-b is common in configuration to the sensor chip 11B of FIG. 8 in that it has a stacked structure in which a sensor substrate 51 on which a pixel array section 12 is formed and a logic substrate 52 on which a global controlling circuit 13 is formed are stacked.

On the other hand, the sensor chip 11B-b is different in configuration from the sensor chip 11B of FIG. 8 in that two global controlling circuits 13-1 and 13-2 are disposed on the logic substrate 52 so as to extend along the upper side and the lower side of the pixel array section 12, respectively, and driving elements 32-1 and 32-2 are connected to the opposite ends of a control line 21.

In particular, in the sensor chip 11B-b, the driving element 32-1 included in the global controlling circuit 13-1 supplies a global controlling signal from the upper end of the control line 21 and the driving element 32-2 included in the global controlling circuit 13-2 supplies a global controlling signal from the lower end of the control line 21 similarly to the sensor chip 11-*a* depicted in FIG. 4.

The sensor chip 11B-b configured in this manner can suppress a skew between the two driving element 32-1 and driving element 32-2 and can eliminate a dispersion in delay time that occurs in a global controlling signal propagated along the control line 21. Consequently, in the sensor chip 11B-b, control for the sensor elements can be performed at a higher speed. It is to be noted that, in the sensor chip 11B-b, it is necessary to perform the control such that the delay difference in outputting of global controlling signals is avoided from becoming great such that through current may not be generated.

In the sensor chip 11B configured in such a manner as described above, control for the sensor elements in the stacked structure in which the sensor substrate 51 and the logic substrate 52 are stacked can be performed at a higher speed similarly as in the sensor chip 11 of FIG. 1.

It is to be noted that, in the configuration examples depicted in FIGS. 8 to 10, the column ADC 15 is configured such that sensor signal is read out from the lower end side of the pixel array section 12 through the TSV region 53-3 and the TSV region 54-3 disposed on the lower side. In addition to such a configuration as just described, for example, two column ADCs 15 are disposed in the proximity of the upper and lower sides and configured such that a sensor signal is read out from the upper end side and the lower end side of the pixel array section 12 by the two column ADCs 15.

<Fourth Configuration Example of Sensor Chip>

A fourth embodiment of a sensor chip to which the present technology is applied is described with reference to FIG. 11. It is to be noted that, from among blocks configuring the sensor chip 11C depicted in FIG. 11, components common to those of the sensor chip 11B of FIG. 8 are denoted by like reference characters, and detailed description of them is omitted.

In particular, as depicted in FIG. 11, the sensor chip 11C is common in configuration to the sensor chip 11B of FIG. 8 in that it has a stacked structure in which a sensor substrate 51 on which a pixel array section 12 is formed and a logic substrate 52 on which a global controlling circuit 13 is formed are stacked.

On the other hand, the sensor chip 11C is different in configuration from the sensor chip 11B of FIG. 8 in that a pixel array section 12C has a vertically elongated rectangular region similarly to the pixel array section 12A of the sensor chip 11A depicted in FIG. 6. Accordingly, in the sensor chip 11C, the global controlling circuit 13C is disposed on the left side of the logic substrate 52 so as to extend along a long side of the pixel array section 12C. With this, a control line 21C is disposed toward the leftward and rightward direction of the pixel array section 12C for each row of the sensor elements disposed in a matrix in the pixel array section 12C.

Further, in the sensor chip 11C, a rolling controlling circuit 14C is disposed on the right side of the logic substrate 52 (side opposing to the global controlling circuit 13C) so as to extend along a long side of the pixel array section 12C. It is to be noted that, although the global controlling circuit 13C and the pixel array section 12C may be disposed on the same side with respect to the logic substrate 52, in this case, since it is supposed that the wiring line length of any one of them becomes longer, it is preferable to adopt such arrangement as depicted in FIG. 11.

Furthermore, in the sensor chip 11C, the column ADC 15C is disposed on the lower side of the logic substrate 52 so as to extend along a short side of the pixel array section 12C. The reason why the column ADC 15C is disposed in a direction orthogonal to the rolling controlling circuit 14C in this manner is that it is necessary to turn on the sensor elements connected to one AD converter one by one, and such a layout that individual wiring lines overlap with each other is avoided.

According to the sensor chip 11C configured in this manner, the wiring line length of the control line 21C can be reduced by the layout in which the global controlling circuit 13C is disposed so as to extend along a long side of the pixel array section 12C similarly to the sensor chip 11B of FIG. 8. Accordingly, the sensor chip 11C can perform control for the sensor elements at a higher speed similarly to the sensor chip 11B of FIG. 8.

<Fifth Configuration Example of Sensor Chip>

A fifth embodiment of a sensor chip to which the present technology is applied is described with reference to FIG. 12. It is to be noted that, from among blocks configuring the sensor chip 11D depicted in FIG. 12, components common to those of the sensor chip 11B of FIG. 8 are denoted by like reference characters, and detailed description of them is omitted.

Figure 12:
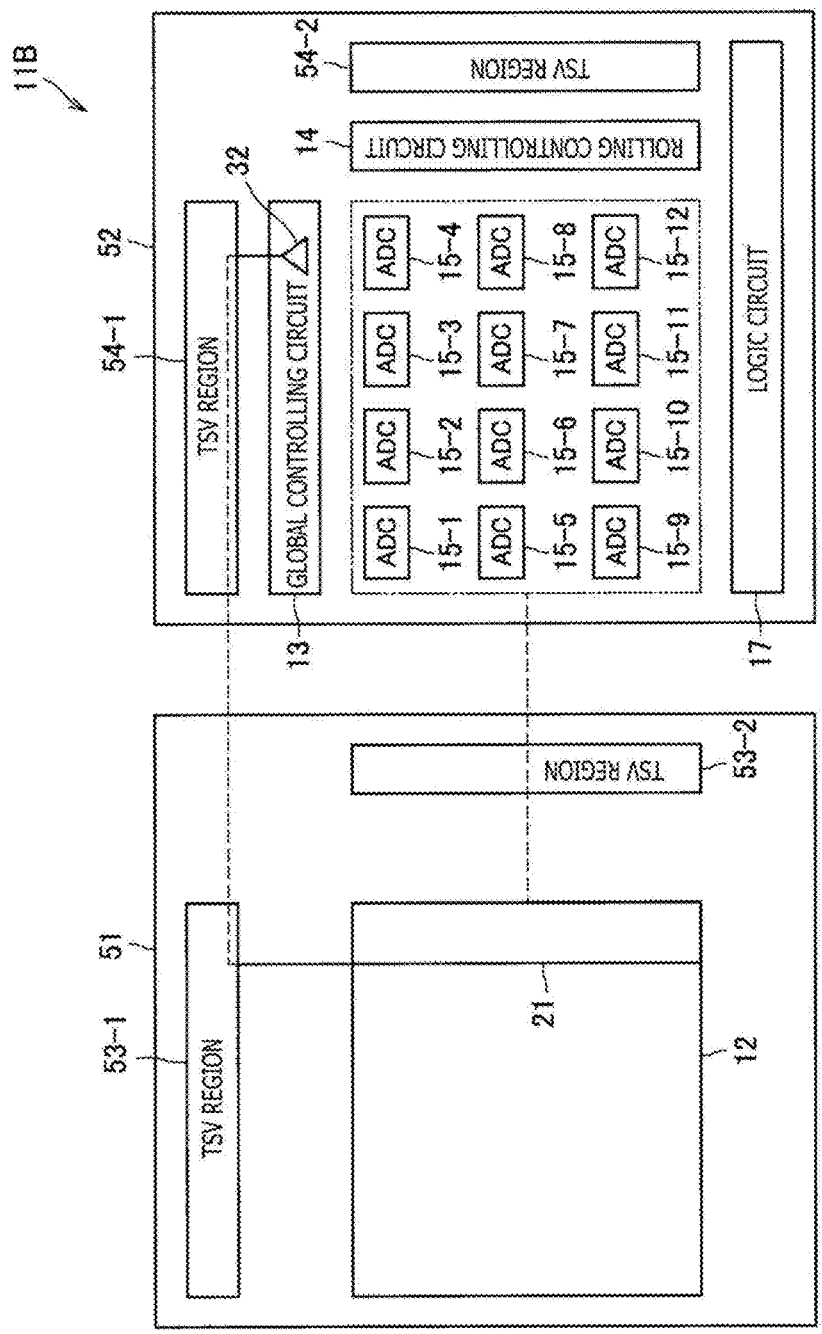
FIG. 12 is a block diagram depicting a configuration example of a fifth embodiment of the sensor chip.

In particular, as depicted in FIG. 12, the sensor chip 11D is common in configuration to the sensor chip 11B of FIG. 8 in that it has a stacked structure in which a sensor substrate 51 on which a pixel array section 12 is formed and a logic substrate 52 on which a global controlling circuit 13 is formed are stacked.

On the other hand, the sensor chip 11D is different in configuration from the sensor chip 11B of FIG. 8 in that, a plurality of column ADCs 15, in the example of FIG. 12, ADCs 15-1 to 15-12, are disposed corresponding to a region of the sensor substrate 51, in which the pixel array section 12 is formed, are disposed on the logic substrate 52.

For example, the sensor chip 11D is configured such that an ADC 15 is disposed for each predetermined region of the pixel array section 12. In the case where the 12 ADCs 15-1 to 15-12 are used as depicted in FIG. 12, an ADC 15 is disposed for each of 12 divisional regions into which the pixel array section 12 is divided equally, and AD conversion of sensor signals outputted from the sensor elements provided in the individual regions is performed in parallel. It is to be noted that, in addition to the configuration in which an ADC 15 is disposed for each of predetermined regions of the pixel array section 12, for example, a configuration in which one ADC 15 is disposed for each of sensor elements included in the pixel array section 12 may be applied.

According to the sensor chip 11D configured in this manner, the wiring line length of the control line 21 can be made short by the layout in which the global controlling circuit 13 is disposed so as to extend along a long side of the pixel array section 12 similarly to the sensor chip 11B of FIG. 8. Accordingly, the sensor chip 11D can perform control for the sensor elements at a higher speed similarly to the sensor chip 11B of FIG. 8.

Further, in the sensor chip 11D, restriction of the positional relationship between the rolling controlling circuit 14 and the column ADC 15 to such constraints to the column ADC 15 depicted in FIG. 8 is eliminated. For example, although, in the sensor chip 11D depicted in FIG. 12, the rolling controlling circuit 14 is disposed on the right side of the logic substrate 52, the rolling controlling circuit 14 may be disposed on any of the upper side and the lower side. In other words, the rolling controlling circuit 14 may be disposed at any place if there is no restriction in regard to the location of the pixel array section 12 with respect to the sensor chip 11D (for example, the center position of the sensor chip 11D with respect to the optical center).

As an alternative, for example, in the case where there is a strong restriction to the optical center and the center position of the sensor chip 11D, the layout can be balanced well by disposing the rolling controlling circuit 14 at a position on the opposite side to the region in which the column ADC 15 is disposed with respect to the global controlling circuit 13. This makes it possible to improve the characteristic of the sensor chip 11D.

<Sixth Configuration Example of Sensor Chip>

A sixth embodiment of a sensor chip to which the present technology is applied is described with reference to FIGS. 13 to 22. It is to be noted that, from among blocks configuring the sensor chip 11E depicted in FIGS. 13 to 22, components common to those of the sensor chip 11B of FIGS. 7 and 8 are denoted by like reference characters, and detailed description of them is omitted.

Figure 13:
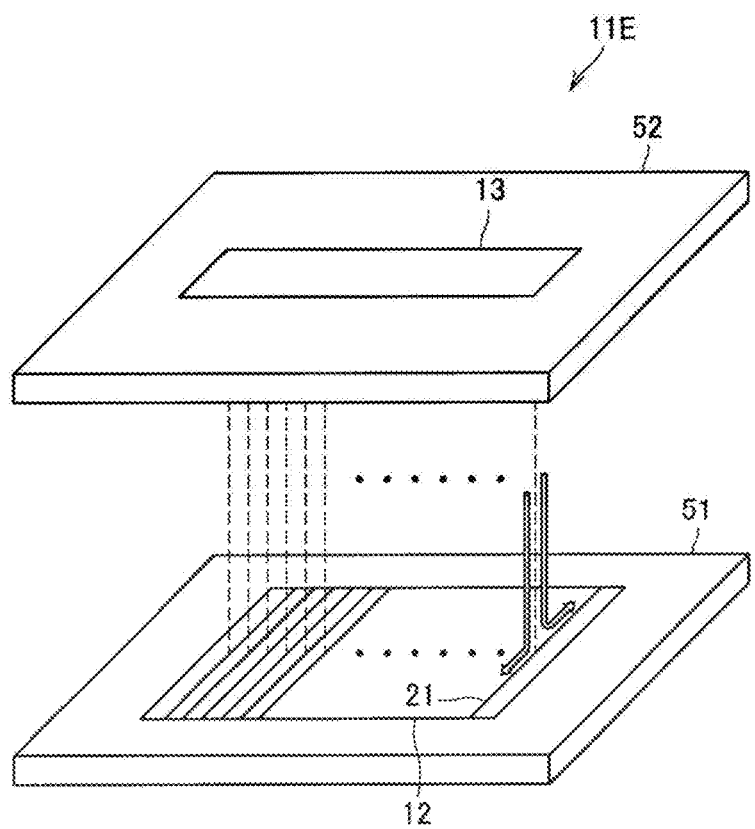
FIG. 13 is a perspective view depicting a configuration example of a sixth embodiment of the sensor chip.

As depicted in FIG. 13, the sensor chip 11E has a stacked structure in which a sensor substrate 51 on which a pixel array section 12 is formed and a logic substrate 52 on which a global controlling circuit 13 is formed are stacked similarly to the sensor chip 11B depicted in FIG. 7. Further, the sensor chip 11E has such a connection structure that the global controlling circuit 13 is disposed such that it overlaps with the center of the pixel array section 12 when the sensor chip 11E is viewed in plan and the global controlling circuit 13 is connected to the control line 21 at the central portion of the pixel array section 12.

For example, in the case where the sensor chip 11E is connectable at the pixel array section 12 by interconnection of copper (Cu) configuring wiring lines, connection utilizing micro bumps or TSVs or like connection, the distance from the driving element 32 to a sensor element disposed at the remote end of the control line 21 can be made short.

A configuration of the sensor chip 11E is further described with reference to FIG. 14.

Figure 14:
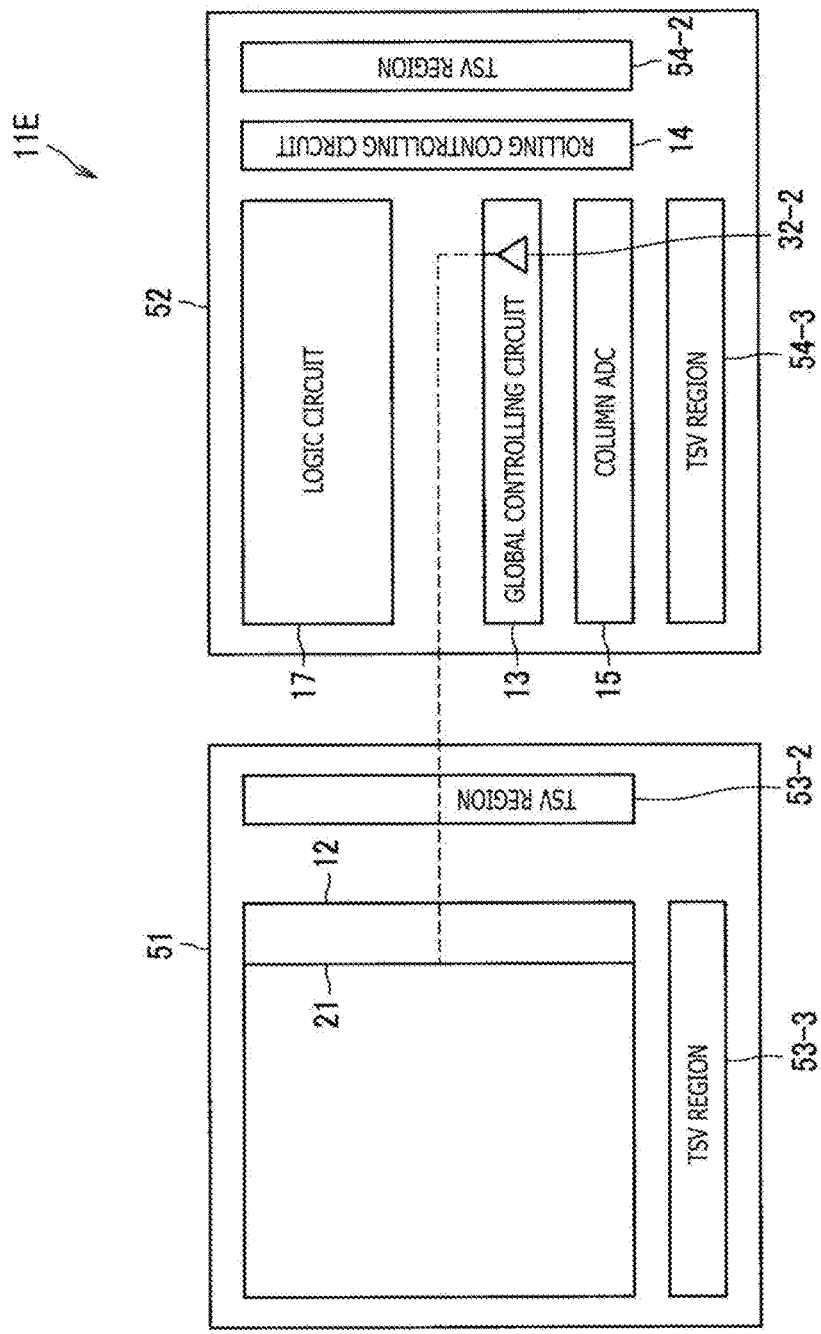
FIG. 14 is a block diagram depicting the configuration example of the sixth embodiment of the sensor chip.

As depicted in FIG. 14, in the sensor substrate 51, the pixel array section 12 is a horizontally elongated rectangular region having long sides extending in the horizontal direction and short sides extending in the vertical direction. Accordingly, on the logic substrate 52, the global controlling circuit 13 is disposed such that the longitudinal direction thereof extends along a long side of the pixel array section 12. Further, the global controlling circuit 13 is disposed substantially at the center of the logic substrate 52 such that a wiring line for outputting from the driving element 32 of the global controlling circuit 13 is connected to the center of a control line 21 disposed toward the upward and downward direction of the pixel array section 12. It is to be noted that such a configuration may be used that a wiring line for outputting from the driving element 32 extends through the substrate from the global controlling circuit 13 directly toward the pixel array section 12.

In the sensor chip 11E configured in this manner, the distances from the driving element 32 to sensor elements at the opposite ends of the control line 21 can be made short. Accordingly, since the delay amount and the slew rate of a global controlling signal can be improved, the sensor chip 11E can perform control for the sensor elements at a higher speed.

Further, such a configuration as indicated by the sensor chip 11E is preferable for application, for example, to a ToF sensor.

Figure 15:
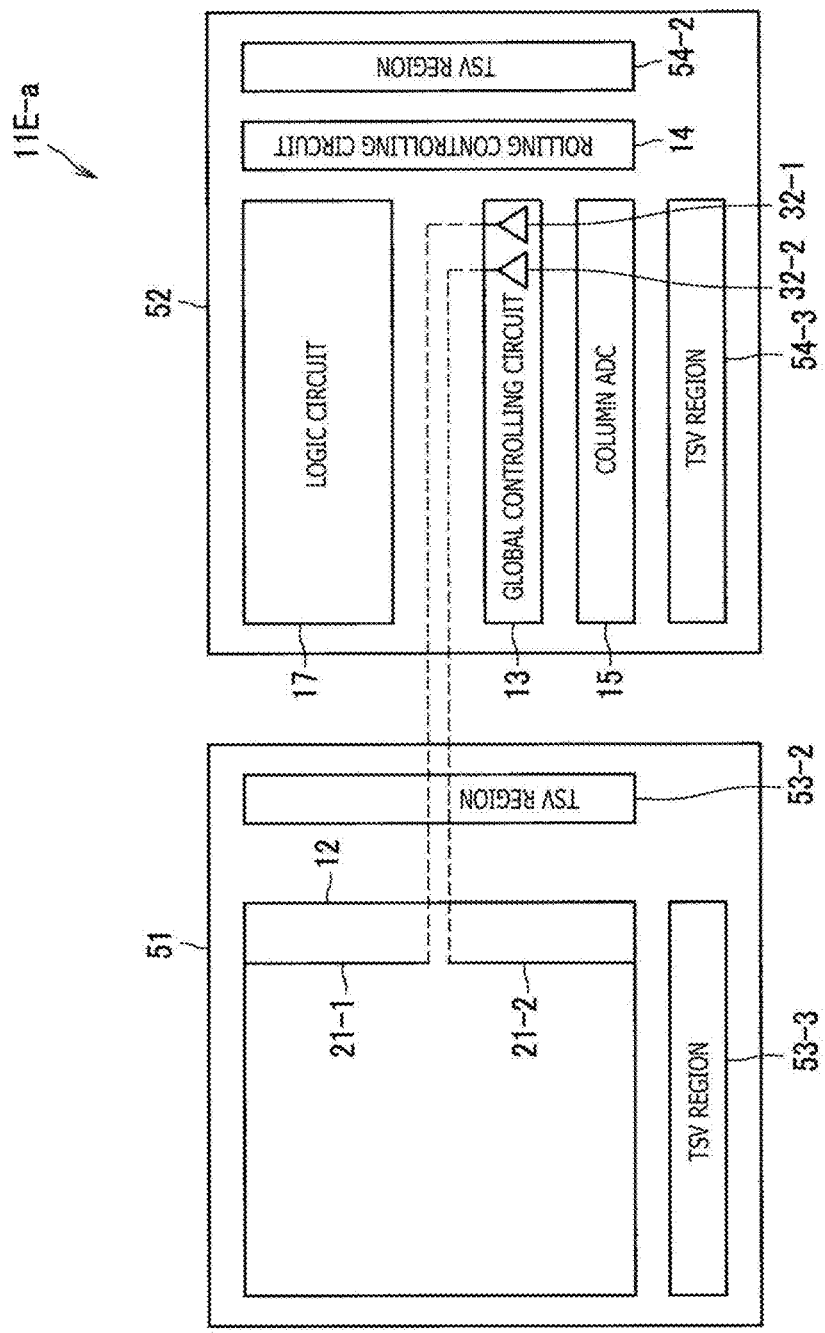
FIG. 15 is a block diagram depicting a first modification of the sensor chip of FIG. 14.

FIG. 15 is a block diagram depicting a first modification of the sensor chip 11E depicted in FIG. 14. It is to be noted that, from among blocks configuring the sensor chip 11E-a depicted in FIG. 15, components common to those of the sensor chip 11E of FIG. 14 are denoted by like reference characters, and detailed description of them is omitted.

In particular, as depicted in FIG. 15, the sensor chip 11E-a is common in configuration to the sensor chip 11E of FIG. 14 in that it has a stacked structure in which a sensor substrate 51 on which a pixel array section 12 is formed and a logic substrate 52 on which a global controlling circuit 13 is formed are stacked.

On the other hand, on the sensor substrate 51, the sensor chip 11E-a is different in configuration from the sensor chip 11E of FIG. 14 in that two control lines 21-1 and 21-2 divided at the center are disposed for one row of sensor elements disposed in a matrix in the pixel array section 12. Further, the sensor chip 11E-a is different in configuration from the sensor chip 11E of FIG. 14 in that the global controlling circuit 13 on the logic substrate 52 includes two driving elements 32-1 and 32-2 for one row of the sensor elements.

Further, the sensor chip 11E-a has such a connection structure that the driving element 32-1 is connected to a center side end portion of the control line 21-1 and the driving element 32-2 is connected to a center side end portion of the control line 21-2. In particular, the sensor chip 11E-a is configured such that, from among a plurality of sensor elements disposed on one row of the pixel array section 12, the sensor elements disposed on the upper side with respect to the center are driven by the driving element 32-1 through the control line 21-1, and the sensor elements disposed on the lower side with respect to the center are driven by the driving element 32-2 through the control line 21-2.

According to the sensor chip 11E-a configured in this manner, the distance from the driving element 32-1 to a sensor element disposed at the remote end of the control line 21-1 and the distance from the driving element 32-2 to a sensor element disposed at the remote end of the control line 21-2 can be made short similarly to the sensor chip 11E of FIG. 14. Accordingly, the sensor chip 11E-a can improve the delay amount and the slew rate of a global controlling signal similarly to the sensor chip 11E of FIG. 14.

Further, in the sensor chip 11E-a, since the load per one driving element 32 can be reduced, the size of the driving element 32 can be reduced from that of the sensor chip 11E of FIG. 14. Furthermore, where the sensor chip 11E-a is configured such that two driving elements 32 are disposed for one column of sensor elements, the layout of the driving elements 32 is integrated to one place, and the overall layout structure can be simplified.

Figure 16:
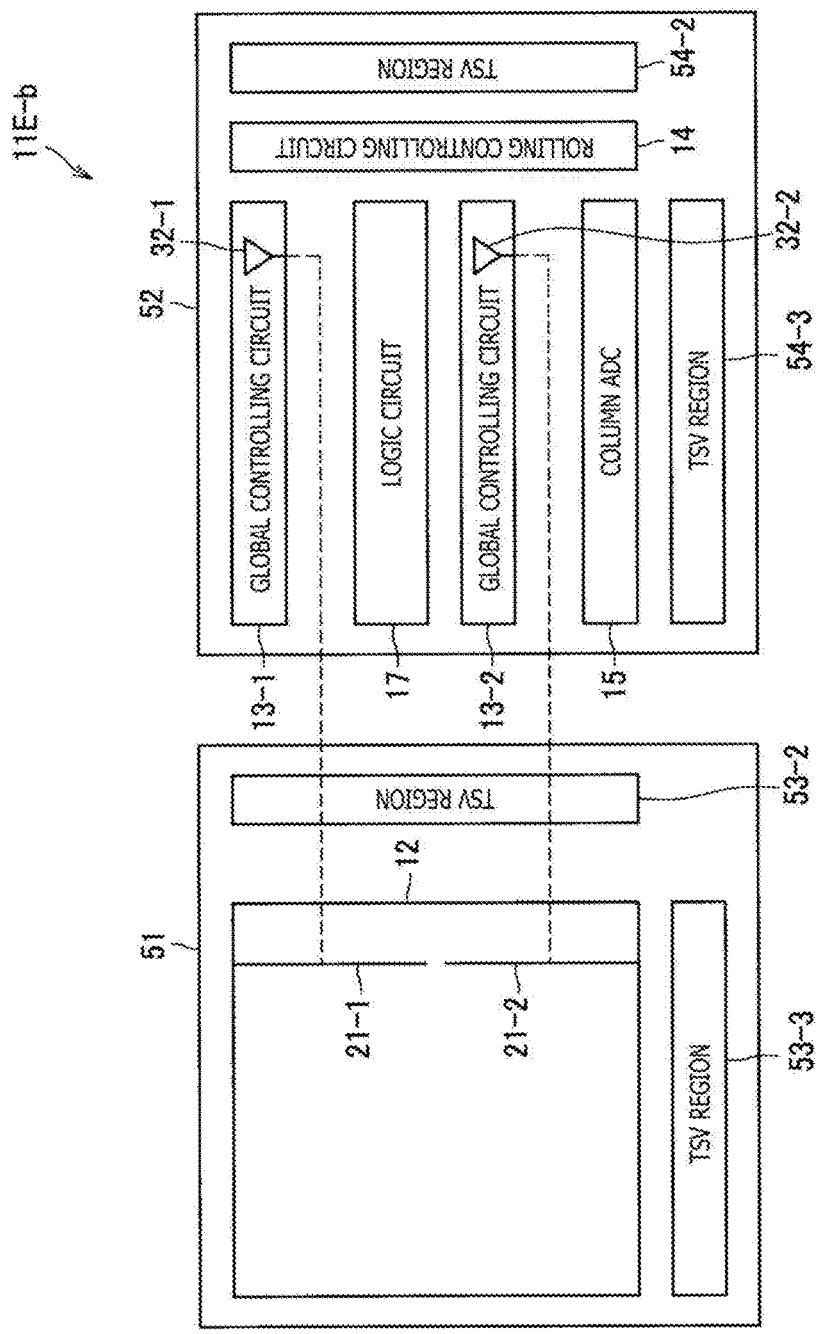
FIG. 16 is a block diagram depicting a second modification of the sensor chip of FIG. 14.

FIG. 16 is a block diagram depicting a second modification of the sensor chip 11E depicted in FIG. 14. It is to be noted that, from among blocks configuring the sensor chip 11E-b depicted in FIG. 16, components common to those of the sensor chip 11E of FIG. 14 are denoted by like reference characters, and detailed description of them is omitted.

In particular, the sensor chip 11E-b depicted in FIG. 16 is common in configuration to the sensor chip 11E of FIG. 14 in that it has a stacked structure in which a sensor substrate 51 on which a pixel array section 12 is formed and a logic substrate 52 on which a global controlling circuit 13 is formed are stacked.

On the other hand, the sensor chip 11E-b is different in configuration from the sensor chip 11E of FIG. 14 in that, on the sensor substrate 51, two control lines 21-1 and 21-2 separate at the center are disposed for one row of sensor elements disposed in a matrix in the pixel array section 12. Further, the sensor chip 11E-b is different in configuration from the sensor chip 11E of FIG. 14 in that, on the logic substrate 52, two global controlling circuits 13-1 and 13-2 are disposed.

Further, the sensor chip 11E-b has such a connection structure that the driving element 32-1 is connected to the center of the control line 21-1 and the driving element 32-2 is connected to the center of the control line 21-2. In particular, the sensor chip 11E-b is configured such that, from among a plurality of sensor elements disposed in one row of the pixel array section 12, the sensor elements disposed on the upper side with respect to the center are driven by the driving element 32-1 through the control line 21-1 and the sensor elements disposed on the lower side with respect to the center are driven by the driving element 32-2 through the control line 21-2.

In the sensor chip 11E-b configured in this manner, the distance from the driving element 32-1 to a sensor element disposed at the remote end of the control line 21-1 and the distance from the driving element 32-2 to a sensor element disposed at the remote end of the control line 21-2 can be made shorter in comparison with the sensor chip 11E of FIG. 14. Consequently, the sensor chip 11E-b can achieve driving at a higher speed than the sensor chip 11E of FIG. 14 and can achieve further improvement of the delay amount and the slew rate of a global controlling signal.

Further, as depicted in FIG. 16, in the sensor chip 11E-b, since the global controlling circuits 13-1 and 13-2 can be disposed divisionally, the logic circuit 17 can be disposed at a central location between them. It is to be noted that, though not depicted, the column ADC 15 may be disposed at a central location between the global controlling circuits 13-1 and 13-2.

Further, such a configuration as indicated by the sensor chip 11E-b is suitable for application, for example, to a ToF sensor.

Figure 17:
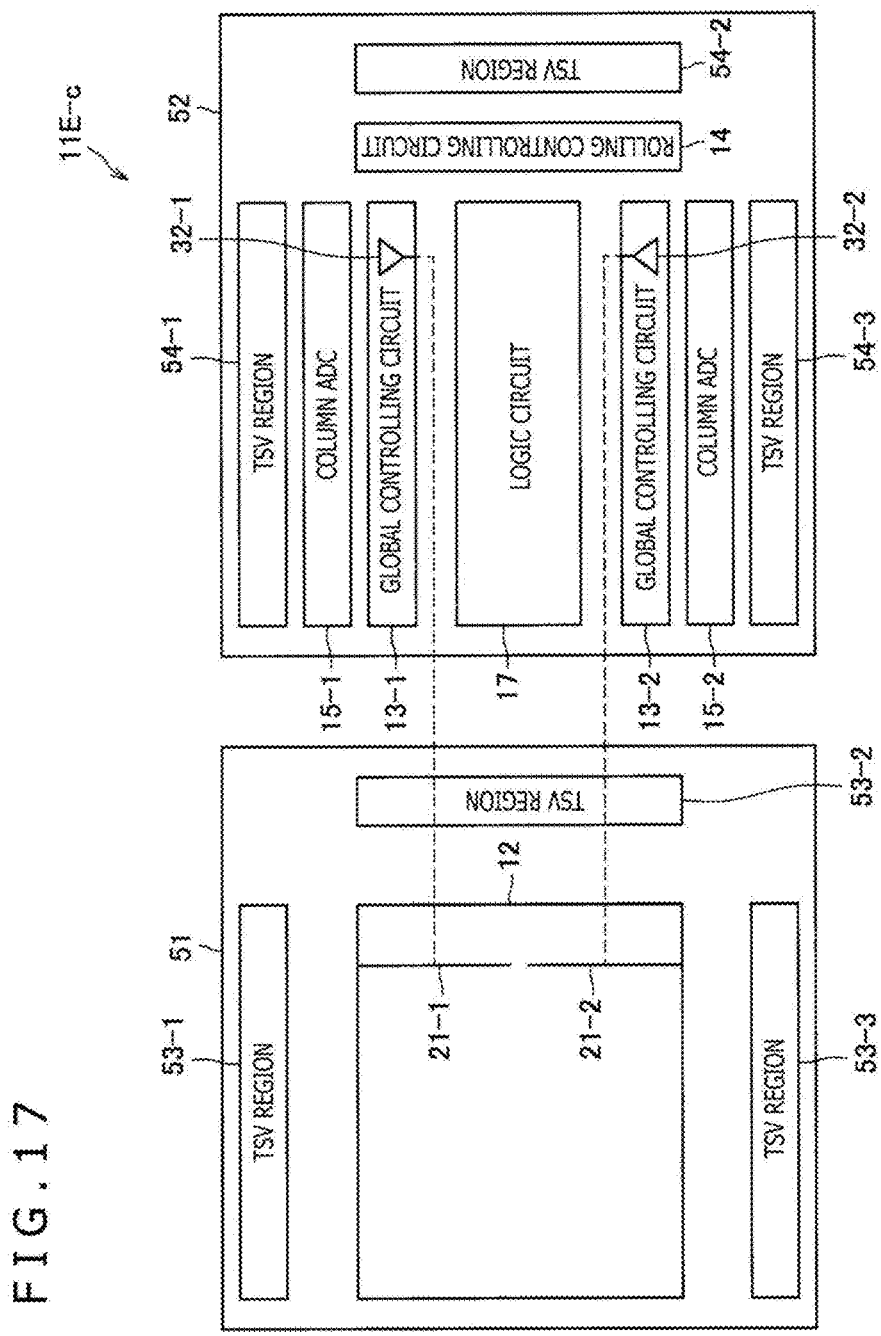
FIG. 17 is a block diagram depicting a third modification of the sensor chip of FIG. 14.

FIG. 17 is a block diagram depicting a third modification of the sensor chip 11E depicted in FIG. 14. It is to be noted that, from among blocks configuring the sensor chip 11E-c depicted in FIG. 17, components common to those of the sensor chip 11E of FIG. 14 are denoted by like reference characters, and detailed description of them is omitted.

In particular, the sensor chip 11E-c depicted in FIG. 17 is common in configuration to the sensor chip 11E of FIG. 14 in that it has a stacked structure in which a sensor substrate 51 on which a pixel array section 12 is formed and a logic substrate 52 on which a global controlling circuit 13 is formed are stacked.

On the other hand, the sensor chip 11E-c is different in configuration from the sensor chip 11E of FIG. 14 in that, on the sensor substrate 51, two control lines 21-1 and 21-2 divided at the center are disposed for one row of sensor elements disposed in a matrix in the pixel array section 12. Further, the sensor chip 11E-c is different in configuration from the sensor chip 11E of FIG. 14 in that two global controlling circuits 13-1 and 13-2 are disposed on the logic substrate 52.

Further, the sensor chip 11E-c has such a connection structure that the driving element 32-1 is connected to the center of the control line 21-1 and the driving element 32-2 is connected to the center of the control line 21-2 similarly to the sensor chip 11E-b of FIG. 16. Accordingly, the sensor chip 11E-c can achieve driving at a higher speed than the sensor chip 11E of FIG. 14 and can achieve further improvement of the delay amount and the slew rate of a global controlling signal in comparison with the sensor chip 11E of FIG. 14 similarly to the sensor chip 11E-b of FIG. 16.

Further, in the sensor chip 11E-c, the column ADC 15-1 is disposed on the upper side of the logic substrate 52 and the column ADC 15-2 is disposed on the lower side of the logic substrate 52. In the sensor chip 11E-c configured in this manner, since it has a structure in which the layout thereof is symmetrical upwardly and downwardly, it is improved in symmetry, and consequently, the sensor chip 11E-c can be improved in characteristic.

Figure 18:
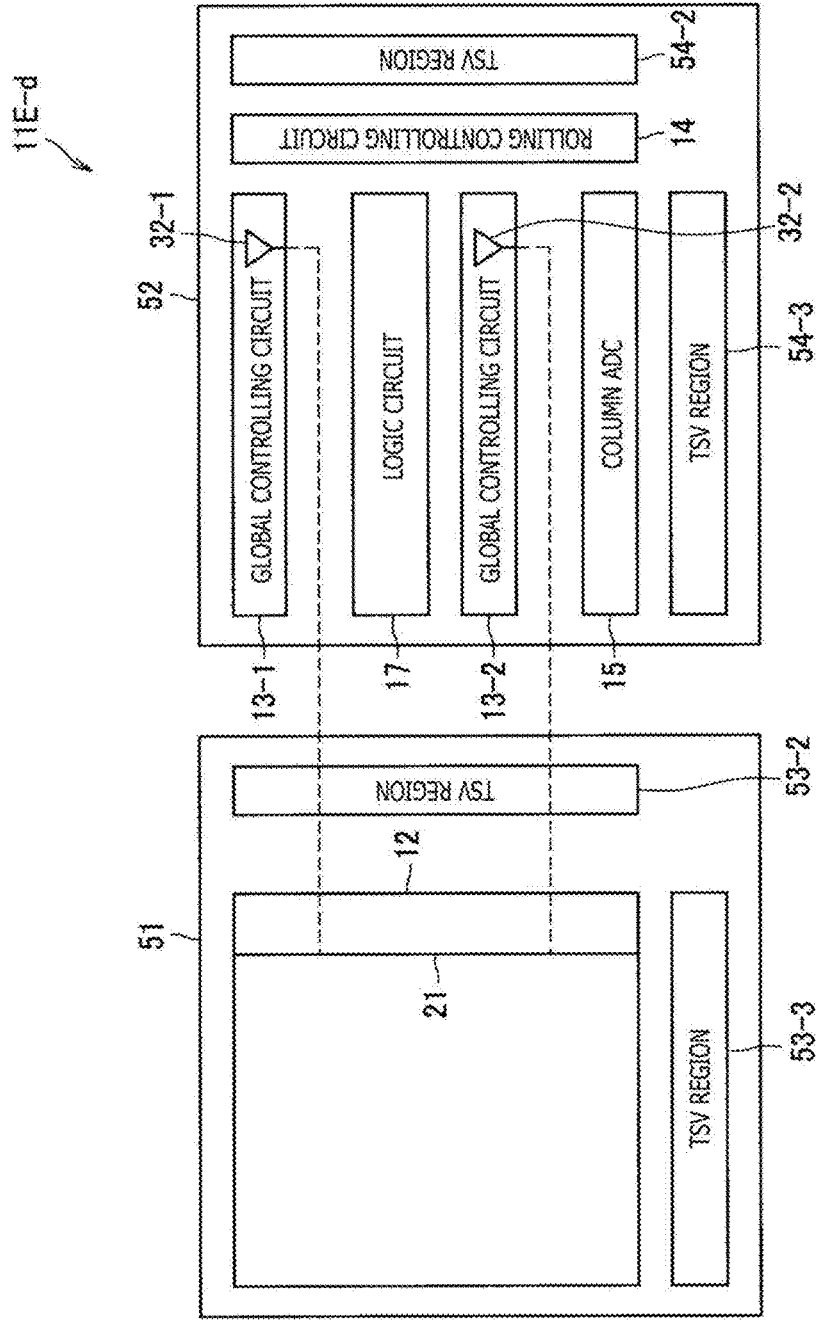
FIG. 18 is a block diagram depicting a fourth modification of the sensor chip of FIG. 14.

FIG. 18 is a block diagram depicting a fourth modification of the sensor block 11E depicted in FIG. 14. It is to be noted that, from among blocks configuring the sensor chip 11E-d depicted in FIG. 18, components common to those of the sensor chip 11E of FIG. 14 are denoted by like reference characters, and detailed description of them is omitted.

In particular, the sensor chip 11E-d depicted in FIG. 18 is common in configuration to the sensor chip 11E of FIG. 14 in that it has a stacked structure in which a sensor substrate 51 on which a pixel array section 12 is formed and a logic substrate 52 on which a global controlling circuit 13 is formed are stacked.

On the other hand, the sensor chip 11E-d is different in configuration from the sensor chip 11E of FIG. 14 in that, on the logic substrate 52, two global controlling circuits 13-1 and 13-2 are disposed and that the sensor chip 11E-d has such a connection structure that the global controlling circuit 13-1 is connected to a substantially center of an upper half of the control line 21 and the global controlling circuit 13-2 is connected to a substantially center of a lower half of the control line 21. In other words, the sensor chip 11E-d is configured such that it uses a single control line 21 to which the control lines 21-1 and 21-2 of FIG. 17 are connected.

The sensor chip 11E-d configured in this manner can suppress a skew between the two driving element 32-1 and driving element 32-2 and can eliminate a dispersion in delay time that occurs in a global controlling signal propagated along the control line 21. Consequently, in the sensor chip 11E-d, control for the sensor elements can be performed at a higher speed. It is to be noted that, in the sensor chip 11E-d, it is necessary to perform the control such that the delay difference in outputting of global controlling signals is avoided from becoming great such that through current may not be generated.

Figure 19:
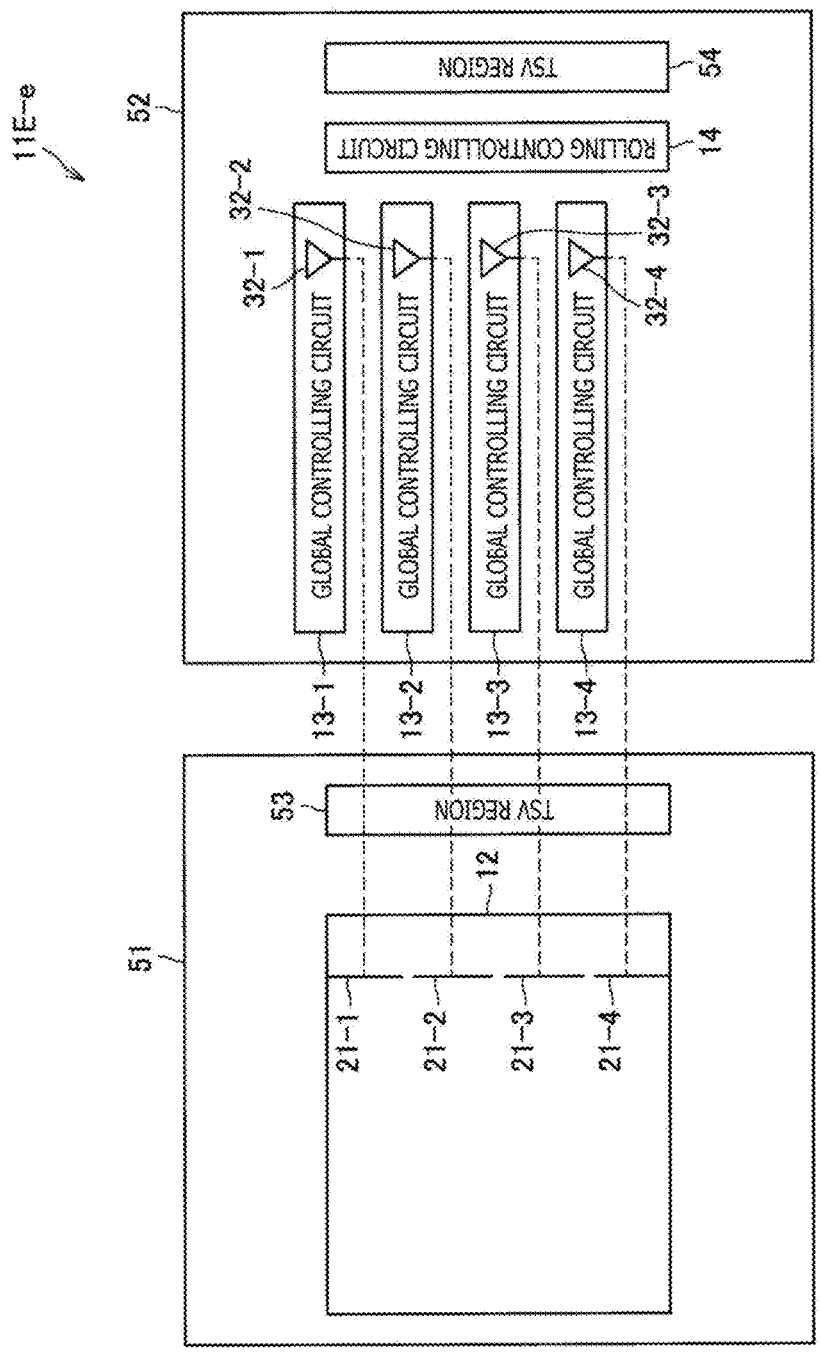
FIG. 19 is a block diagram depicting a fifth modification of the sensor chip of FIG. 14.

FIG. 19 is a block diagram depicting a fifth modification of the sensor block 11E depicted in FIG. 14. It is to be noted that, from among blocks configuring the sensor chip 11E-e depicted in FIG. 19, components common to those of the sensor chip 11E of FIG. 14 are denoted by like reference characters, and detailed description of them is omitted. Further, in the sensor chip 11E-e depicted in FIG. 19, in order to avoid the illustration from becoming complicated, illustration of part of blocks configuring the sensor chip 11E-e is omitted.

In particular, the sensor chip 11E-e depicted in FIG. 19 is common in configuration to the sensor chip 11E of FIG. 14 in that it has a stacked structure in which a sensor substrate 51 on which a pixel array section 12 is formed and a logic substrate 52 on which a global controlling circuit 13 is formed are stacked.

On the other hand, the sensor chip 11E-e is different in configuration from the sensor chip 11E of FIG. 14 in that, on the sensor substrate 51, four divisional control lines 21-1 to 21-4 are disposed for one row of sensor elements disposed in a matrix in the pixel array section 12. Further, the sensor chip 11E-e is different in configuration from the sensor chip 11E of FIG. 14 in that, on the logic substrate 52, four global controlling circuits 13-1 to 13-4 are disposed.

Further, the sensor chip 11E-e has such a connection configuration that driving elements 32-1 to 32-4 of the global controlling circuits 13-1 to 13-4 are connected to central points of the control lines 21-1 to 21-4, respectively. Accordingly, in the sensor chip 11E-e, the distance from the driving elements 32-1 to 32-4 to sensor elements disposed at the remote end of the respective control lines 21-1 to 21-4 can be further reduced. Consequently, the sensor chip 11E-e can achieve further increase in speed of control for the sensor elements. It is to be noted that, although it is supposed that the column ADC 15A, logic circuit 17 and so forth are disposed separately, also in such a case as just described, it is necessary to adopt a layout in which this does not have an influence on a characteristic.

It is to be noted that, although the configuration example depicted in FIG. 19 is described using the four divisional control lines 21-1 to 21-4, the control line 21 may otherwise be divided into three control lines or five or more control lines. Thus, such a configuration can be taken that, to substantially central portions of the divisional control lines 21, respectively corresponding global controlling circuits 13 are connected.

Figure 20:
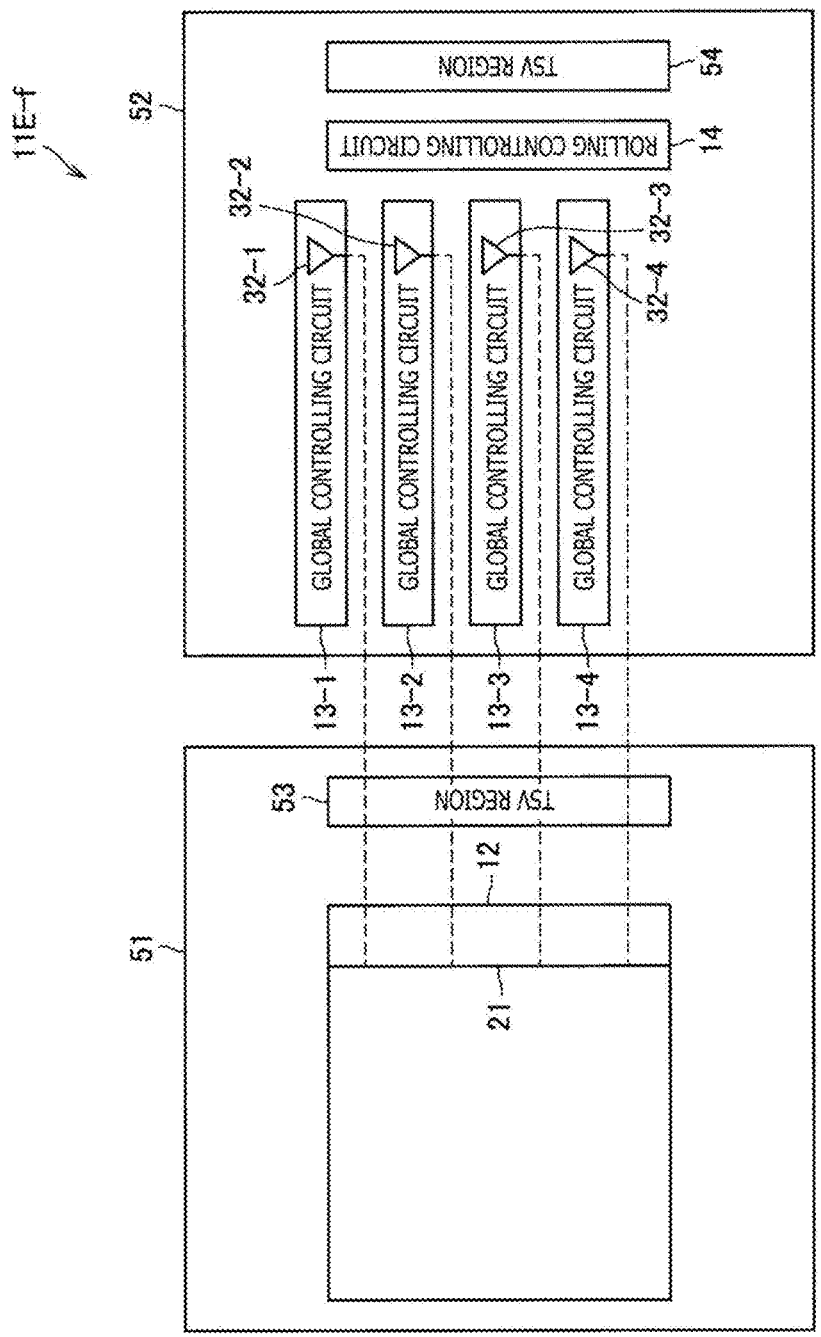
FIG. 20 is a block diagram depicting a sixth modification of the sensor chip of FIG. 14.

FIG. 20 is a block diagram depicting a sixth modification of the sensor block 11E depicted in FIG. 14. It is to be noted that, from among blocks configuring the sensor chip 11E-f depicted in FIG. 20, components common to those of the sensor chip 11E of FIG. 14 are denoted by like reference characters, and detailed description of them is omitted.

In particular, the sensor chip 11E-f depicted in FIG. 20 is common in configuration to the sensor chip 11E of FIG. 14 in that it has a stacked structure in which a sensor substrate 51 on which a pixel array section 12 is formed and a logic substrate 52 on which a global controlling circuit 13 is formed are stacked.

On the other hand, the sensor chip 11E-f is different in configuration from the sensor chip 11E of FIG. 14 in that four global controlling circuits 13-1 to 13-4 are disposed on the logic substrate 52 and global controlling circuits 13-1 to 13-4 are connected at equal distances to the control line 21. In other words, the sensor chip 11E-d is configured such that it uses a single control line 21 to which the control lines 21-1 to 21-4 of FIG. 19 are connected.

The sensor chip 11E-f configured in this manner can suppress a skew among the four driving elements 32-1 to 32-4 and can eliminate a dispersion in delay time that occurs in a global controlling signal propagated along the control line 21. Consequently, in the sensor chip 11E-f, control for the sensor elements can be performed at a higher speed. It is to be noted that, in the sensor chip 11E-f, it is necessary to perform the control such that the delay difference in outputting of global controlling signals becomes great such that through current may not be generated.

Figure 21:
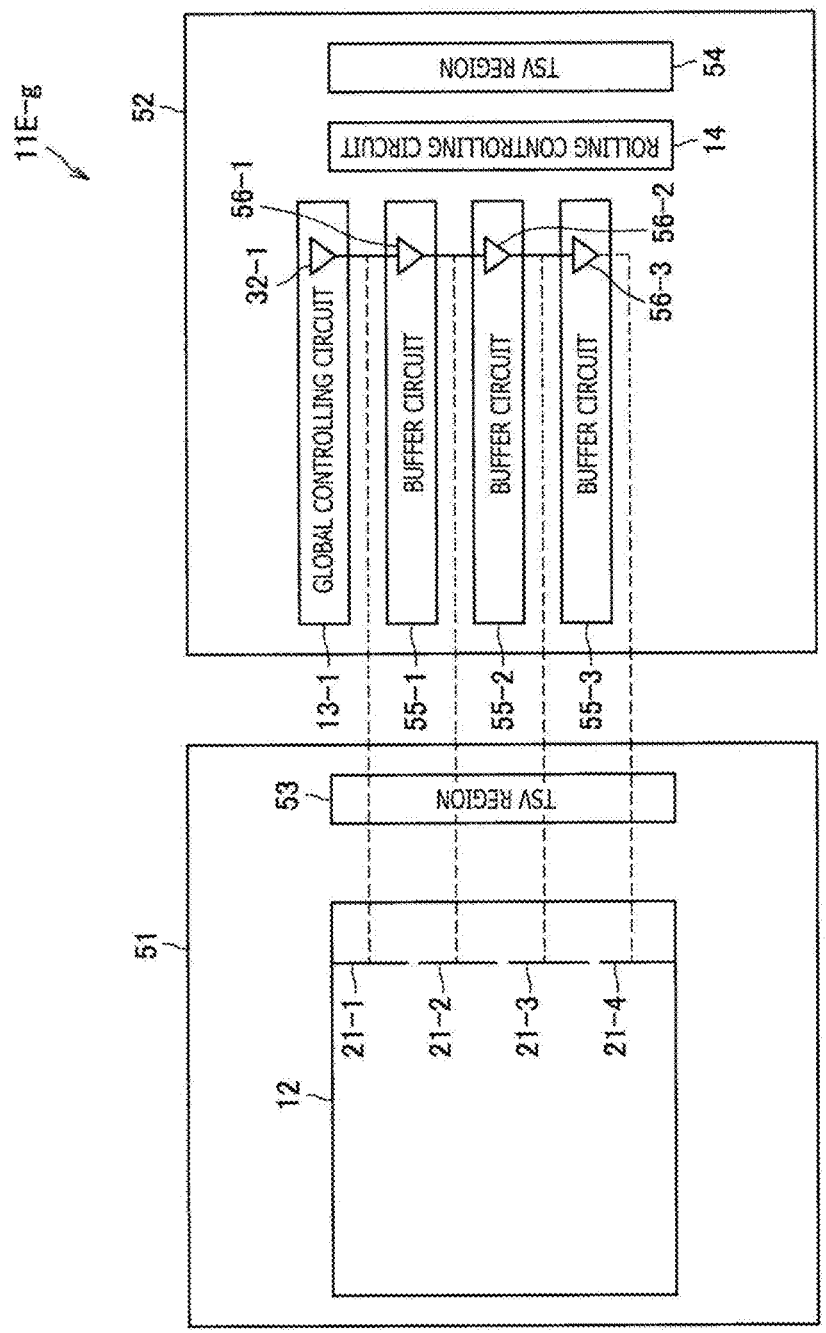
FIG. 21 is a block diagram depicting a seventh modification of the sensor chip of FIG. 14.

FIG. 21 is a block diagram depicting a seventh modification of the sensor block 11E depicted in FIG. 14. It is to be noted that, from among blocks configuring the sensor chip 11E-g depicted in FIG. 21, components common to those of the sensor chip 11E-e of FIG. 19 are denoted by like reference characters, and detailed description of them is omitted.

In particular, the sensor chip 11E-g is configured including a single global controlling circuit 13 and is configured including buffer circuits 55-1 to 55-3 in place of the global controlling circuits 13-2 to 13-4 of the sensor chip 11E-e of FIG. 19. The buffer circuits 55-1 to 55-3 have buffers 56-1 to 56-3, respectively, and an output of the driving element 32 of the global controlling circuit 13 is branched by the buffers 56-1 to 56-3 and connected to four divisional control lines 21-1 to 21-4.

Also with the sensor chip 11E-g configured in this manner, further increase in speed of control for the sensor elements can be achieved similarly with the sensor chip 11E-e of FIG. 19.

Figure 22:
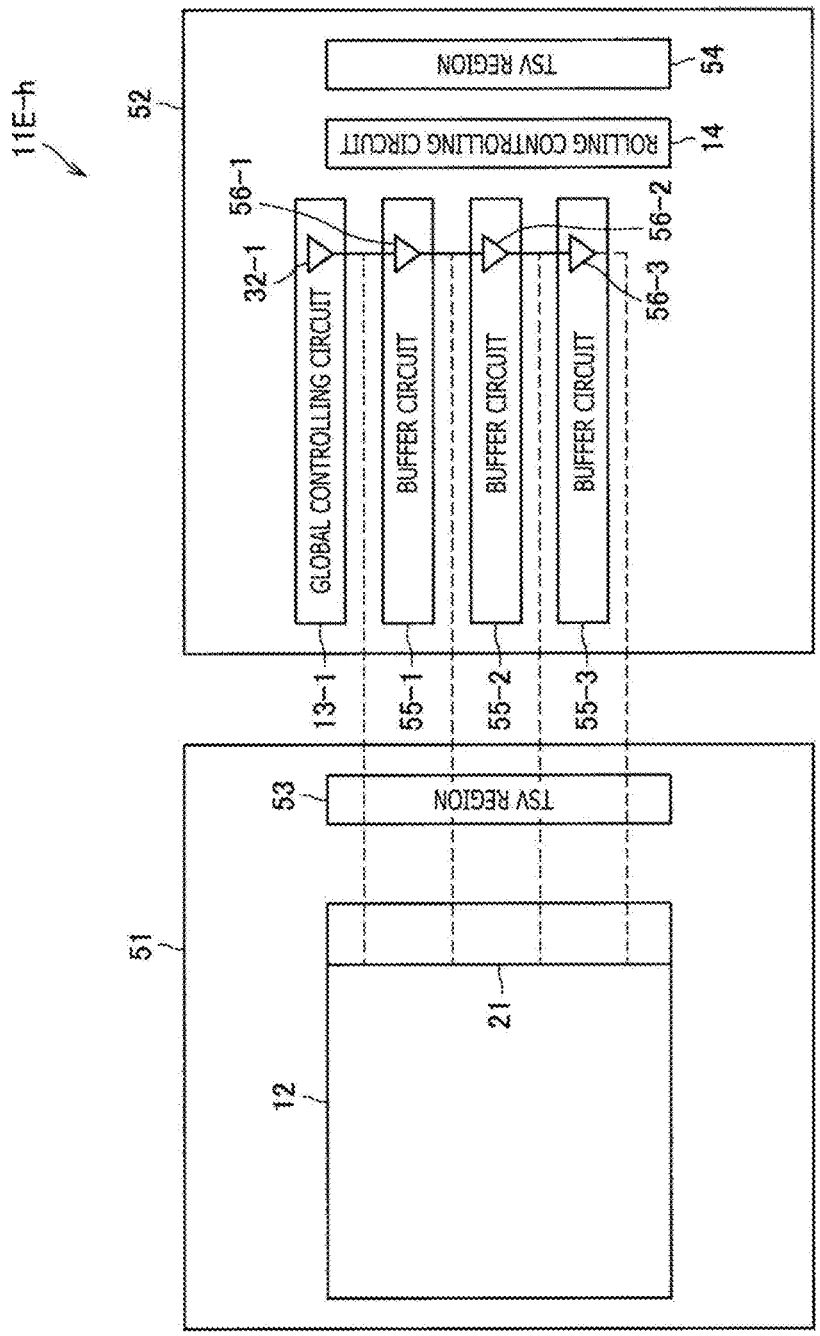
FIG. 22 is a block diagram depicting an eighth modification of the sensor chip of FIG. 14.

FIG. 22 is a block diagram depicting an eighth modification of the sensor block 11E depicted in FIG. 14. It is to be noted that, from among blocks configuring the sensor chip 11E-h depicted in FIG. 22, components common to those of the sensor chip 11E-f of FIG. 20 are denoted by like reference characters, and detailed description of them is omitted.

In particular, the sensor chip 11E-g is configured including a single global controlling circuit 13 and is configured including buffer circuits 55-1 to 55-3 in place of the global controlling circuits 13-2 to 13-4 of the sensor chip 11E-f of FIG. 20. The buffer circuits 55-1 to 55-3 have buffers 56-1 to 56-3, respectively, and an output of the driving element 32 of the global controlling circuit 13 is branched by the buffers 56-1 to 56-3 and connected to a control line 21.

Also with the sensor chip 11E-h configured in this manner, further increase in speed of control for the sensor elements can be achieved similarly with the sensor chip 11E-f of FIG. 20.

<Seventh Configuration Example of Sensor Chip>

A seventh embodiment of a sensor chip to which the present technology is applied is described with reference to FIGS. 23 to 25. It is to be noted that, from among blocks configuring the sensor chip 11F depicted in FIGS. 23 to 25, components common to those of the sensor chip 11E of FIG. 13 are denoted by like reference characters, and detailed description of them is omitted.

Figure 23:
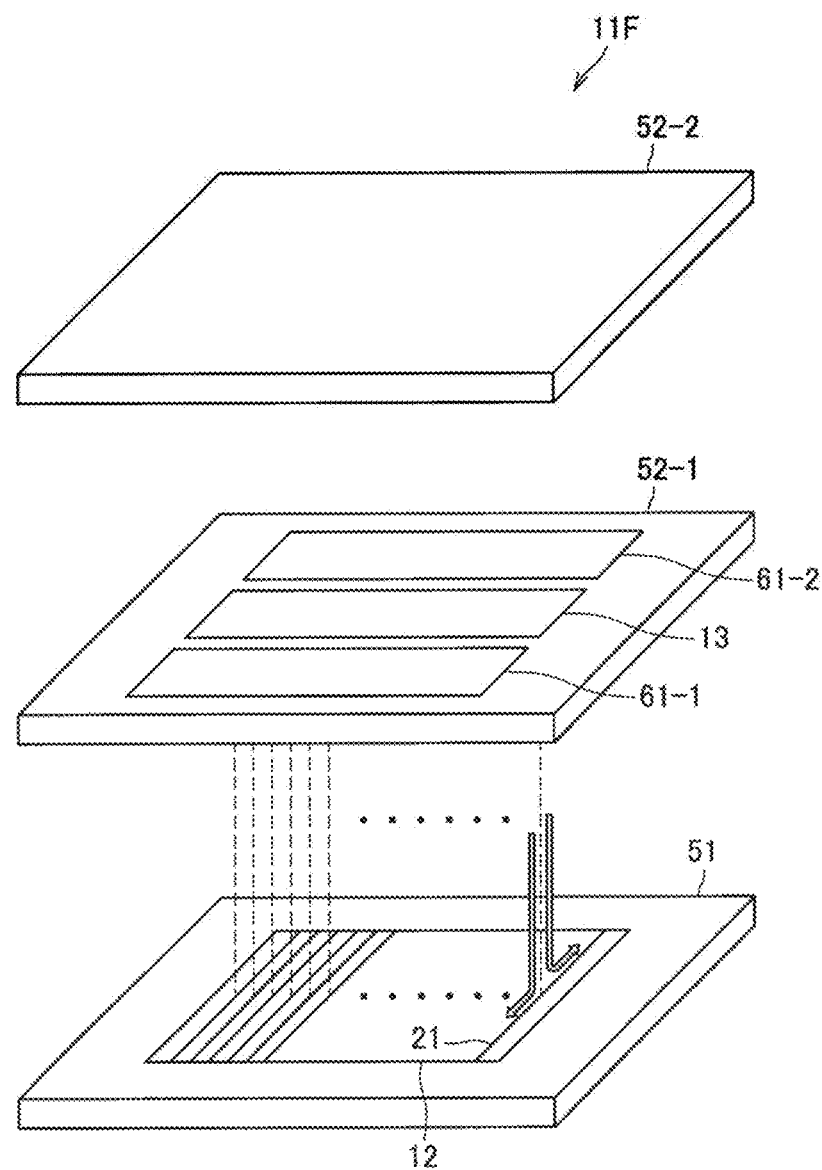
FIG. 23 is a perspective view depicting a configuration example of a seventh embodiment of the sensor chip.

In particular, the sensor chip 11F depicted in FIG. 23 has a stacked structure in which a sensor substrate 51 and two logic substrates 52-1 and 52-2 are stacked. In other words, the present technology can be applied to a structure in which three semiconductor substrates are stacked.

As depicted in FIG. 23, the sensor chip 11F is configured such that a pixel array section 12 is formed on a sensor substrate 51 of the first layer and a global controlling circuit 13 and memories 61-1 and 61-2 are formed on a logic substrate 52-1 of the second layer while, for example, a column ADC 15, a logic circuit 17 and forth not depicted are formed on a logic substrate 52-2 of the third layer.

Also in the sensor chip 11F configured in this manner, by disposing the global controlling circuit 13 on the logic substrate 52-1 along the longitudinal direction of the pixel array section 12 of the sensor substrate 51, control for the sensor elements can be performed at a higher speed similarly as in the sensor chip 11E of FIG. 13.

Further, in the sensor chip 11F in which the sensor substrate 51, logic substrate 52-1 and logic substrate 52-2 are slacked in this order, preferably the global controlling circuit 13 is disposed at the center of the logic substrate 52-1 stacked between the sensor substrate 51 and the logic substrate 52-2. Consequently, the distance from the global controlling circuit 13 to a sensor element disposed at the remote end of the logic substrate 52-1 can be made short. Naturally, if the distance from the global controlling circuit 13 to a sensor element disposed at the remote end of the control line 21 can be made short, then the layout is not limited to such a layout as depicted in FIG. 23.

Figure 24:
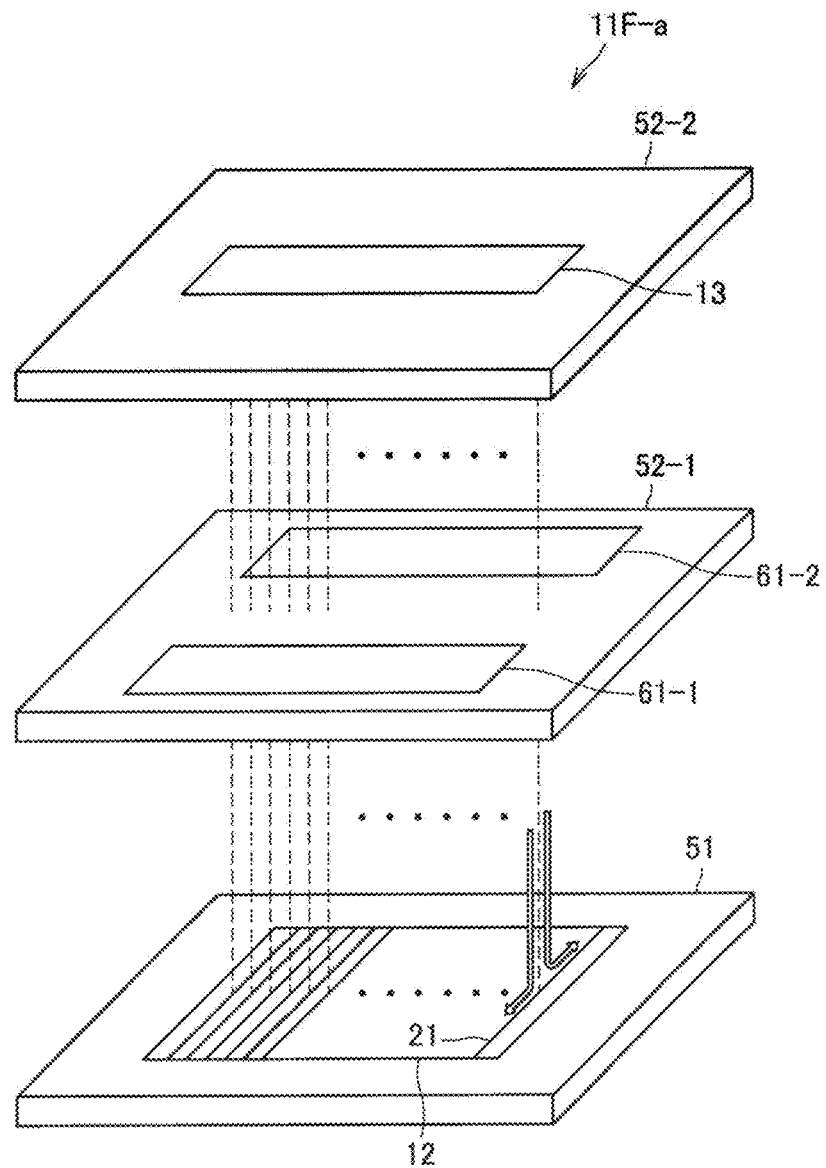
FIG. 24 is a perspective view depicting a first modification of the sensor chip of FIG. 23.

FIG. 24 is a perspective view depicting a first modification of the sensor chip 11F depicted in FIG. 23.

As depicted in FIG. 24, the sensor chip 11F-a is configured such that the pixel array section 12 is formed on the sensor substrate 51 of the first layer; the memories 61-1 and 61-2 are formed on the logic substrate 52-1 of the second layer; and, for example, the global controlling circuit 13, the column ADC 15 and logic circuit 17 not depicted and so forth are formed on the logic substrate 52-2 of the third layer.

Also in the sensor chip 11F-a configured in this manner, by disposing the global controlling circuit 13 on the logic substrate 52-2 so as to extend along the longitudinal direction of the pixel array section 12 of the sensor substrate 51, control for the sensor elements can be performed at a higher speed similarly as in the sensor chip 11E of FIG. 13.

Figure 25:
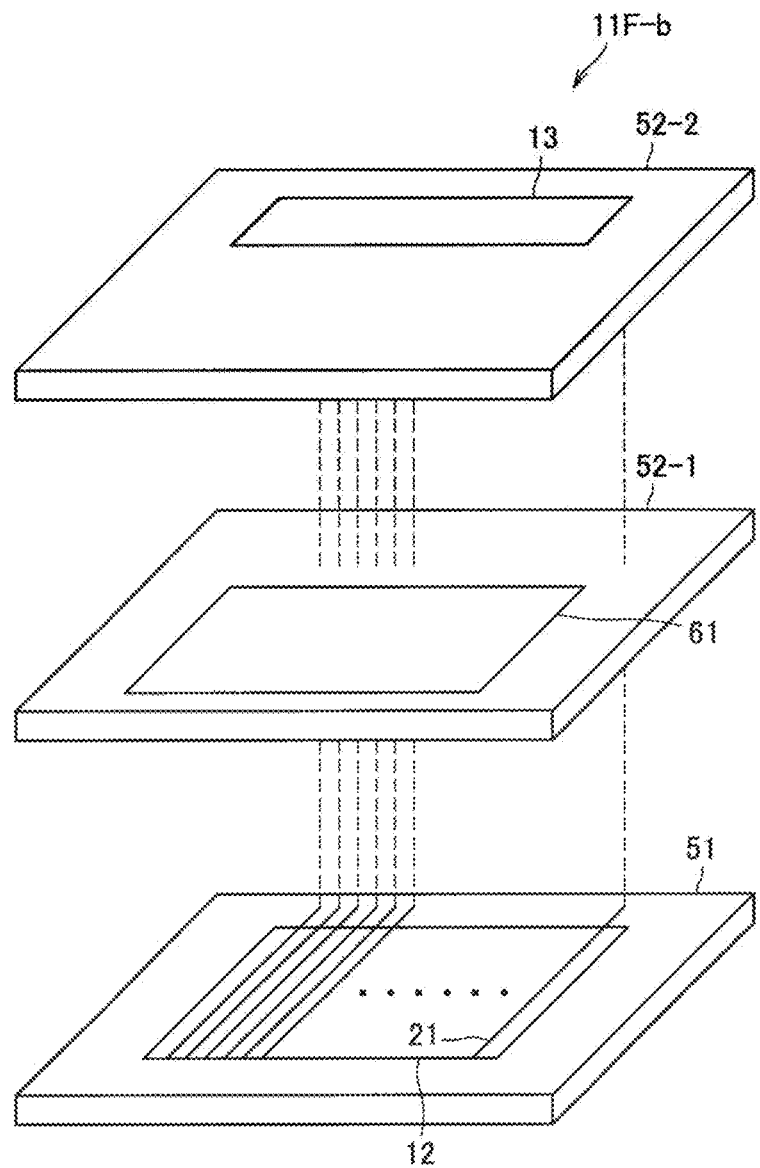
FIG. 25 is a perspective view depicting a second modification of the sensor chip of FIG. 23.

FIG. 25 is a perspective view depicting a second modification of the sensor chip 11F depicted in FIG. 23.

As depicted in FIG. 25, the sensor chip 11F-b is configured such that the pixel array section 12 is formed on the sensor substrate 51 of the first layer; the memory 61 is formed on the logic substrate 52-1 of the second layer; and, for example, the global controlling circuit 13, the column ADC 15 and logic circuit 17 not depicted and so forth are formed on the logic substrate 52-2 of the third layer. It is to be noted that the sensor chip 11F-b has such a connection configuration that the control line 21 is connected to the global controlling circuit 13 utilizing a TSV region formed in a peripheral region of the sensor chip 11F-b, for example, similarly to the sensor chip 11B of FIG. 8.

Also in the sensor chip 11F-b configured in this manner, by disposing the global controlling circuit 13 on the logic substrate 52-2 so as to extend along the longitudinal direction of the pixel array section 12 of the sensor substrate 51, control for the sensor elements can be performed at a higher speed similarly as in the sensor chip 11E of FIG. 13.

It is to be noted that, for example, three or more semiconductor substrates may be stacked, and a global controlling circuit 13 may be disposed at two locations as described hereinabove with reference to FIG. 16 or a global controlling circuit 13 may be disposed at a plurality of locations equal to or greater than two locations. In this case, a semiconductor substrate on which the memory 61 is disposed, the location or divisional number of the memory 61 can be laid out suitably in response to the disposition of the global controlling circuit 13.

For example, such a configuration may be adopted that the pixel array section 12 is disposed on a semiconductor substrate of the first layer; the column ADC 15, logic circuit 17 and so forth are disposed on a semiconductor substrate of the second layer; and the memory 61 is disposed on a semiconductor substrate of the third layer. Also in such a configuration as just described, by disposing the global controlling circuit 13 on the semiconductor substrate of the second layer, the wiring line length can be made short. However, the global controlling circuit 13 may otherwise be disposed on a semiconductor substrate on which the memory 61 is disposed.

<Eighth Configuration Example of Sensor Chip>

An eighth embodiment of a sensor chip to which the present technology is applied is described with reference to FIG. 26. It is to be noted that, from among blocks configuring the sensor chip 11G depicted in FIG. 26, components common to those of the sensor chip 11E of FIG. 14 are denoted by like reference characters, and detailed description of them is omitted.

Figure 26:
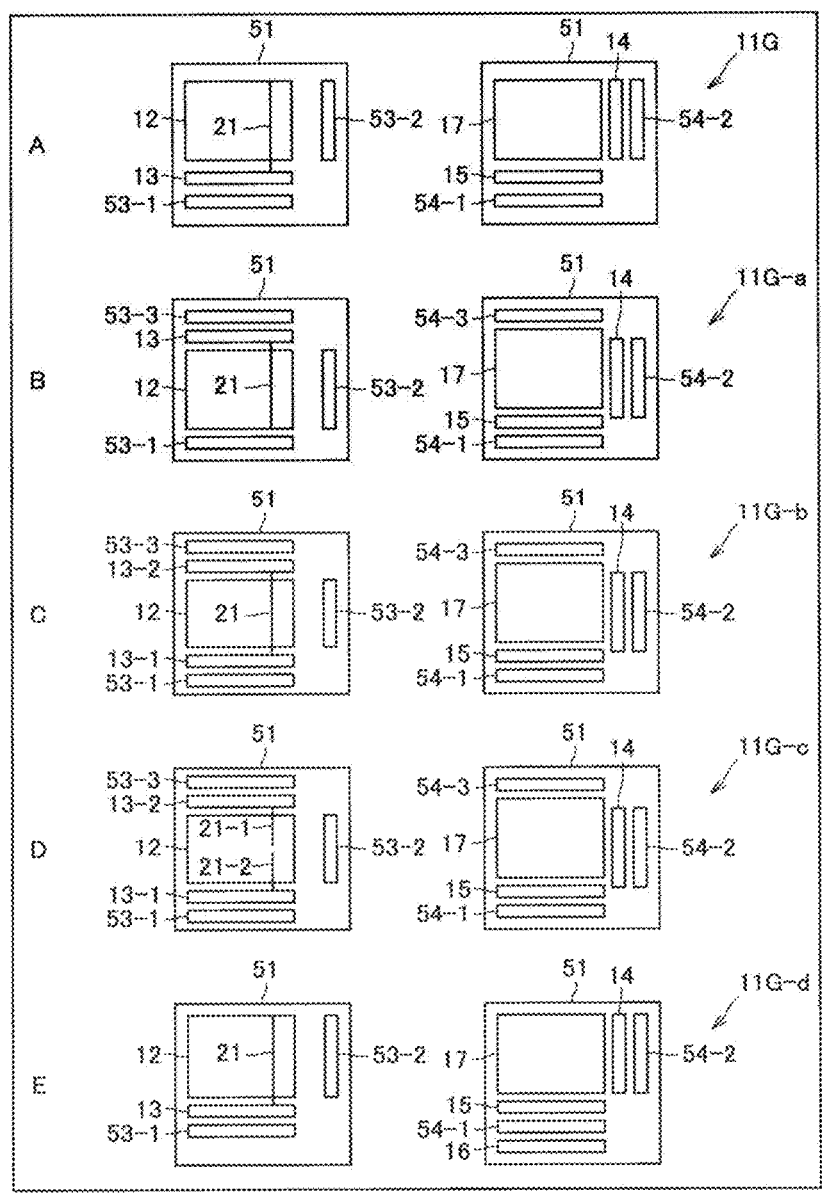
FIG. 26 is a block diagram depicting a configuration example of an eight embodiment of the sensor chip and a modification of the same.

In particular, the disposition of the global controlling circuit 13 in the sensor chip 11 is not limited to those in the embodiments described hereinabove, and such various layouts as depicted in FIG. 26 can be adopted. Naturally, in any disposition, such a layout that is not depicted may be adopted if the global controlling circuit 13 is disposed so as to extend along a long side of the pixel array section 12.

As depicted in FIG. 26A, a sensor chip 11G has such a layout that the pixel array section 12 and the global controlling circuit 13 are disposed on the sensor substrate 51 and the rolling controlling circuit 14, column ADC 15 and logic circuit 17 are disposed on the logic substrate 52. Further, in the sensor chip 11G, the global controlling circuit 13 is disposed on the lower side of the pixel array section 12 so as to extend along a long side of the pixel array section 12.

As depicted in FIG. 26B, a sensor chip 11G-a has such a layout that the pixel array section 12 and the global controlling circuit 13 are disposed on the sensor substrate 51 and the rolling controlling circuit 14, column ADC 15 and logic circuit 17 are disposed on the logic substrate 52. Further, in the sensor chip 11G-a, the global controlling circuit 13 is disposed on the upper side of the pixel array section 12 so as to extend along a long side of the pixel array section 12.

As depicted in FIG. 26C, a sensor chip 11G-b has such a layout that the pixel array section 12 and the global controlling circuits 13-1 and 13-2 are disposed on the sensor substrate 51 and the rolling controlling circuit 14, column ADC 15 and logic circuit 17 are disposed on the logic substrate 52. Further, in the sensor chip 11G-b, the global controlling circuits 13-1 and 13-2 are disposed on the upper side and the lower side of the pixel array section 12 so as to extend along a long side of the pixel array section 12, respectively.

As depicted in FIG. 26D, a sensor chip 11G-c has such a layout that the pixel array section 12 and the global controlling circuits 13-1 and 13-2 are disposed on the sensor substrate 51 and the rolling controlling circuit 14, column ADC 15 and logic circuit 17 are disposed on the logic substrate 52. Further, in the sensor chip 11G-c, the global controlling circuits 13-1 and 13-2 are disposed on the upper side and the lower side of the pixel array section 12 so as to extend along a long side of the pixel array section 12, respectively, and the two control lines 21-1 and 21-2 are disposed such that they are separate at the center of a column of the sensor elements disposed in a matrix on the pixel array section 12.

As depicted in FIG. 26E, a sensor chip 11G-d has such a layout that the pixel array section 12 and the global controlling circuits 13-1 and 13-2 are disposed on the sensor substrate 51 and the rolling controlling circuit 14, column ADC 15 and logic circuit 17 are disposed on the logic substrate 52. Further, in the sensor chip 11G-d, the inputting and outputting section 16 is disposed on the logic substrate 52 so as to extend along a long side of the pixel array section 12.

For example, the sensor chip 11G-d is configured such that it supplies power from the inputting and outputting section 16 to the global controlling circuit 13 through the TSV region 54-1 and the TSV region 53-1. It is to be noted that, in addition to utilization of a TSV, interconnection of copper (Cu) configuring wiring lines, micro bumps and so forth may be utilized to supply power to the global controlling circuit 13. Further, for the wiring line for supplying power to the global controlling circuit 13, a same connection method as that for the control line 21 may be used or a connection method of some other combination may be used. Further, in addition to the configuration in which semiconductor substrates of two layers are stacked, also in a configuration in which semiconductor substrates of three layers are stacked, preferably the global controlling circuit 13 is disposed in the proximity of the inputting and outputting section 16 similarly.

It is to be noted that, while the various layouts depicted in FIG. 26 indicate exampled in which the column ADC 15 is disposed on one side of the logic substrate 52, a layout in which the column ADC 15 is disposed on the opposite upper and lower sides of the logic substrate 52 may be adopted. Further, the position of the column ADC 15 or the logic circuit 17 is not restricted to such disposition as depicted in FIG. 26.

As described above, by applying a stacked structure to the sensor chip 11, the global controlling circuit 13 can be disposed in various layouts, which increases the degree of freedom in layout and increases the effect of controlling the global controlling circuit 13 and the rolling controlling circuit 14 individually.

<Configuration Example of Distance Image Sensor>

Figure 27:
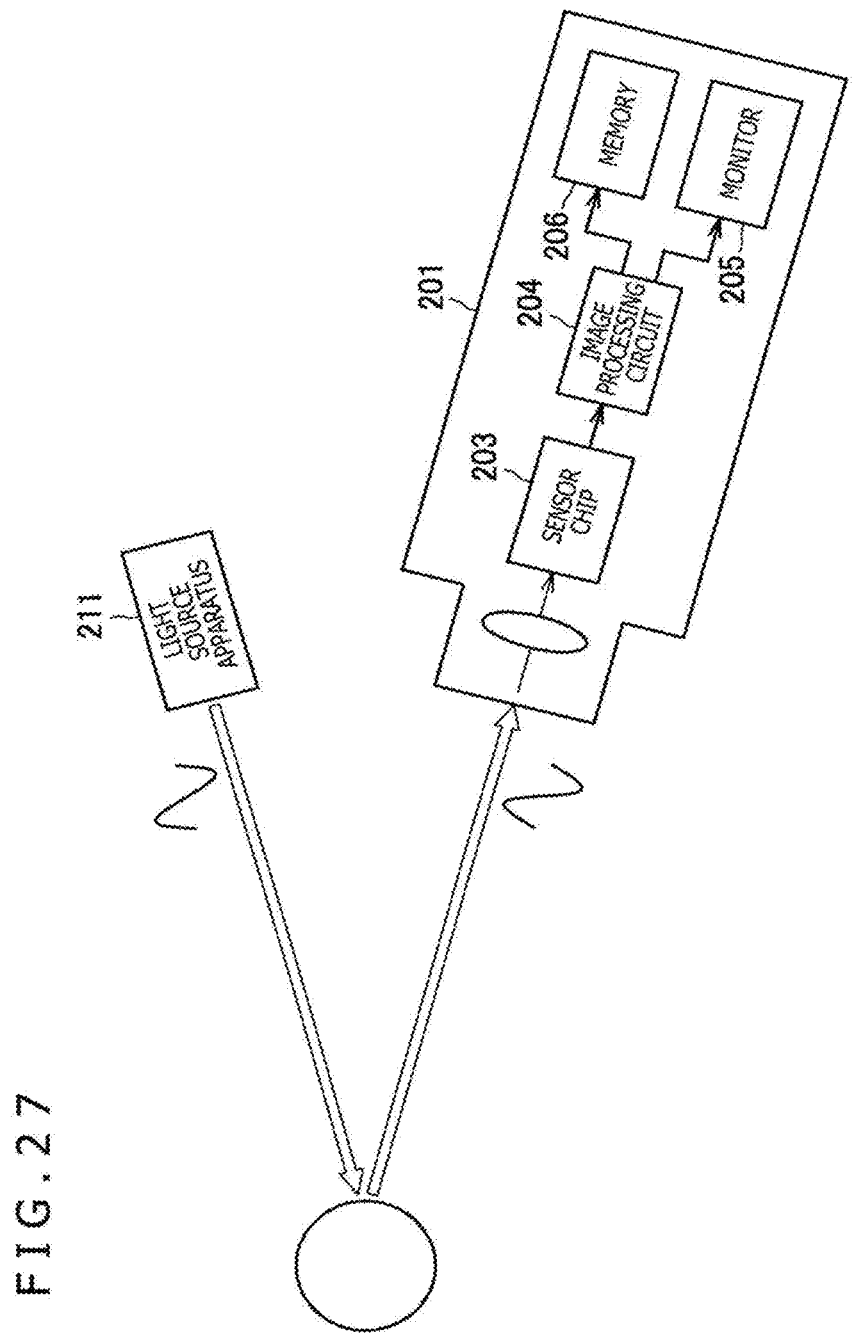
FIG. 27 is a block diagram depicting a configuration example of an imaging apparatus.

FIG. 27 is a block diagram depicting a configuration example of a distance image sensor that is an electronic apparatus utilizing the sensor chip 11.

As depicted in FIG. 27, the distance image sensor 201 is configured including an optical system 202, a sensor chip 203, an image processing circuit 204, a monitor 205 and a memory 206. Thus, the distance image sensor 201 can acquire a distance image according to the distance of an imaging object by receiving light (modulated light or pulse light) projected from a light source apparatus 211 toward the imaging object and reflected by the surface of the imaging object.

The optical system 202 is configured having one or a plurality of lenses and introduces image light (incident light) from an imaging object to the sensor chip 203 such that an image is formed on a light reception face (sensor section) of the sensor chip 203.

As the sensor chip 203, the sensor chip 11 of the embodiments described hereinabove is applied, and a distance signal indicative of a distance determined from a reception signal (APD OUT) outputted from the sensor chip 203 is supplied to the image processing circuit 204.

The image processing circuit 204 performs image processing for constructing a distance image on the basis of a distance signal supplied from the sensor chip 203, and a distance image (image data) obtained by the imaging processing is supplied to and displayed on the monitor 205 or supplied to and stored (recorded) into the memory 206.

In the distance image sensor 201 configured in this manner, by applying the sensor chip 11 described above, for example, a more accurate distance image can be acquired by performance of higher speed control.

[1.3. Particular Configuration Examples of Distance Image Sensor]

In a ToF camera system that adopts the indirect system, light is irradiated in the form of pulses, and a pulse generator for generating such pulses is provided. An existing pulse generator makes a phase by a shift register after division. Accordingly, a phase resolution is determined by a division setting. For example, if a signal of a frequency of 800 MHz is divided by eight, then only eight phases can be made. Further, in an existing pulse generator, steps of division or phase that can be made are limited to multiples of two. Accordingly, it is not possible to obtain a phase of 36 degrees by division by ten. Preferably, a ToF camera system that adopts the indirect system can perform wide setting in order to adaptively change the frequency by a range. Further, although it is necessary for an existing pulse generator to change the frequency of a PLL in order to perform fine setting, if the frequency of the PLL is changed, then time is required before the frequency is stabilized (it is necessary to weight for response time).

Further, an existing pulse generator is great in number of flip-flops and is low in area efficiency. For example, a 32-divider requires 32 flip-flops, and also a shift register of 32 steps requires 32 flip-flops. Accordingly, a pulse generator configured from a divide-by-32 divider and a shift register of 32 steps requires 64 flip-flops.

Thus, taking the foregoing into consideration, the discloser of the present case has conducted an intensive study about the technology of a pulse generator that is used in a ToF camera system that especially adopts the indirect system and can be ready for various settings for a frequency or a phase with a simple configuration. As a result, the discloser of the present case has invented a pulse generator that is used in a ToF camera system that especially adopts the indirect system and can be ready for various settings for a frequency or a phase while it is simple in configuration.

Figure 28:
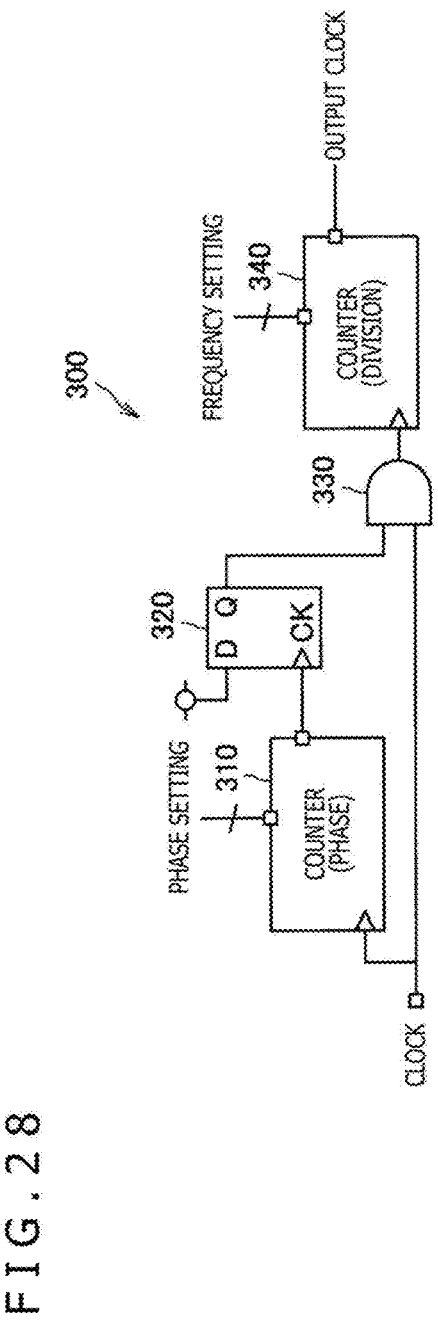
FIG. 28 is an explanatory view depicting a functional configuration example of a pulse generator 300 according to an embodiment of the present disclosure.

Now, a configuration example used in a ToF camera system that especially adopts the indirect system according to an embodiment of the present disclosure is described. FIG. 28 is an explanatory view depicting a functional configuration example of the pulse generator 300 according to the embodiment of the present disclosure. The pulse generator 300 depicted in FIG. 28 is, for example, a pulse generator provided in the distance image sensor 201 depicted in FIG. 27. In the following, the functional configuration example of the pulse generator 300 according to the embodiment of the present disclosure is described with reference to FIG. 28.

As depicted in FIG. 28, the pulse generator 300 according to the embodiment of the present disclosure is configured including counters 310 and 340, a D-type flip-flog 320 and an AND gate 330.

The counter 310 is a programmable counter that counts clocks inputted to the pulse generator 300, for example, clocks generated by a PLL. The counter 310 is a counter for setting a phase and is, for example, a counter that adds a value at the timing of a rising edge of a clock inputted thereto. A phase setting is sent from the outside of the pulse generator 300 to the counter 310. An output of the counter 310 is sent to an input of the D-type flip-flog 320.

The D-type flip-flog 320 uses an output of the counter 310 as a clock CK thereto and outputs a value of an input D from an output Q on the basis of the clock CK. The output of the D-type flip-flog 320 is sent to the AND gate 330.

The AND gate 330 logically ANDs (AND) a clock inputted to the pulse generator 300 and an output of the D-type flip-flog 320, and outputs a result of the ANDing to the counter 340.

The counter 340 is a programmable counter that counts output clocks of the AND gate 330. The counter 340 is a counter for setting division and is, for example, a counter that adds a value at the timing of a rising edge of a clock inputted thereto.

A counter used as the counters 310 and 340 may be any counter if it is a programmable counter. Constituent factors of a programmable counter are that the counter is a multi-bit counter, that the counter receives data of multi bits as an input, that the counter includes a comparator between input data and a count value and so forth. As such counter, a pulse swallow counter, a pulse follower counter, a binary counter, a gray code counter, a Johnson counter and so forth are applicable.

Figure 29:
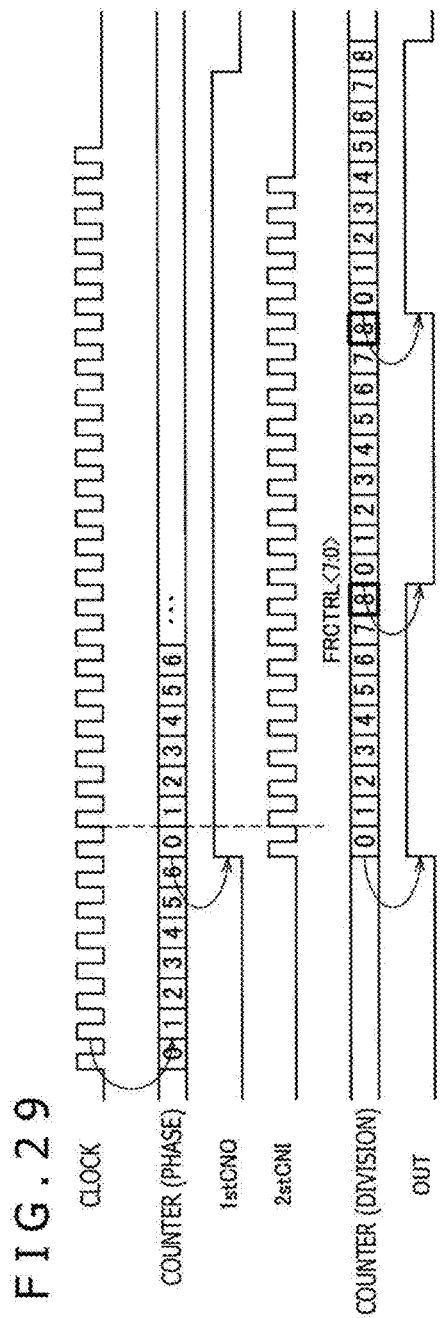
FIG. 29 is an explanatory view of an example of waveforms of signals.

FIG. 29 is an explanatory view depicting a waveform example of a signal inputted to the pulse generator 300, signals generated in the inside of the pulse generator 300 and a signal outputted from the pulse generator 300.

Referring to FIG. 29, "Clock" indicates a clock inputted to the pulse generator 300, and "Counter (phase)" indicates a count value by the counter 310. "1stCNO" indicates an output of the D-type flip-flog 320, and "2stCNI" indicates an output of the AND gate 330. "Counter (division)" indicates a count value by the counter 340, and "OUT" indicates an output of the counter 340.

In the example depicted in FIG. 29, the output of the D-type flip-flog 320 switches from low to high when the count value of the counter 310 becomes "6." Further, when the count value by the counter 340 becomes "8," the output of the counter 340 switches from low to high or from high to low. In particular, the phase and the frequency of a clock to be outputted from the pulse generator 300 can be adjusted by changing the settings of the counters 310 and 340.

By using the clock outputted from the pulse generator 300 for driving of a light source and driving of pixels of a sensor chip, the driving timing of the light source and the driving timing of the pixels of the sensor chip can be adjusted flexibly. For example, it is possible to set $2^8$ as the phase setting and set $2^8$ as the division setting. In this case, the number of flip-flops is eight for each counter and is totaling 16 for the implementation. Accordingly, in comparison with a conventional pulse generator that requires 64 flip-flops, the pulse generator according to the embodiment of the present disclosure can significantly reduce the circuit scale.

It is to be noted that, while, in the pulse generator 300 depicted in FIG. 28, the counter 340 for setting a frequency is provided in the next stage to the counter 310 for setting a phase, the present disclosure is not limited to such an example as just described. In the pulse generator 300 according to the present embodiment, a counter for setting a phase may be provided in the stage next to a counter for setting a frequency.

Figure 30:
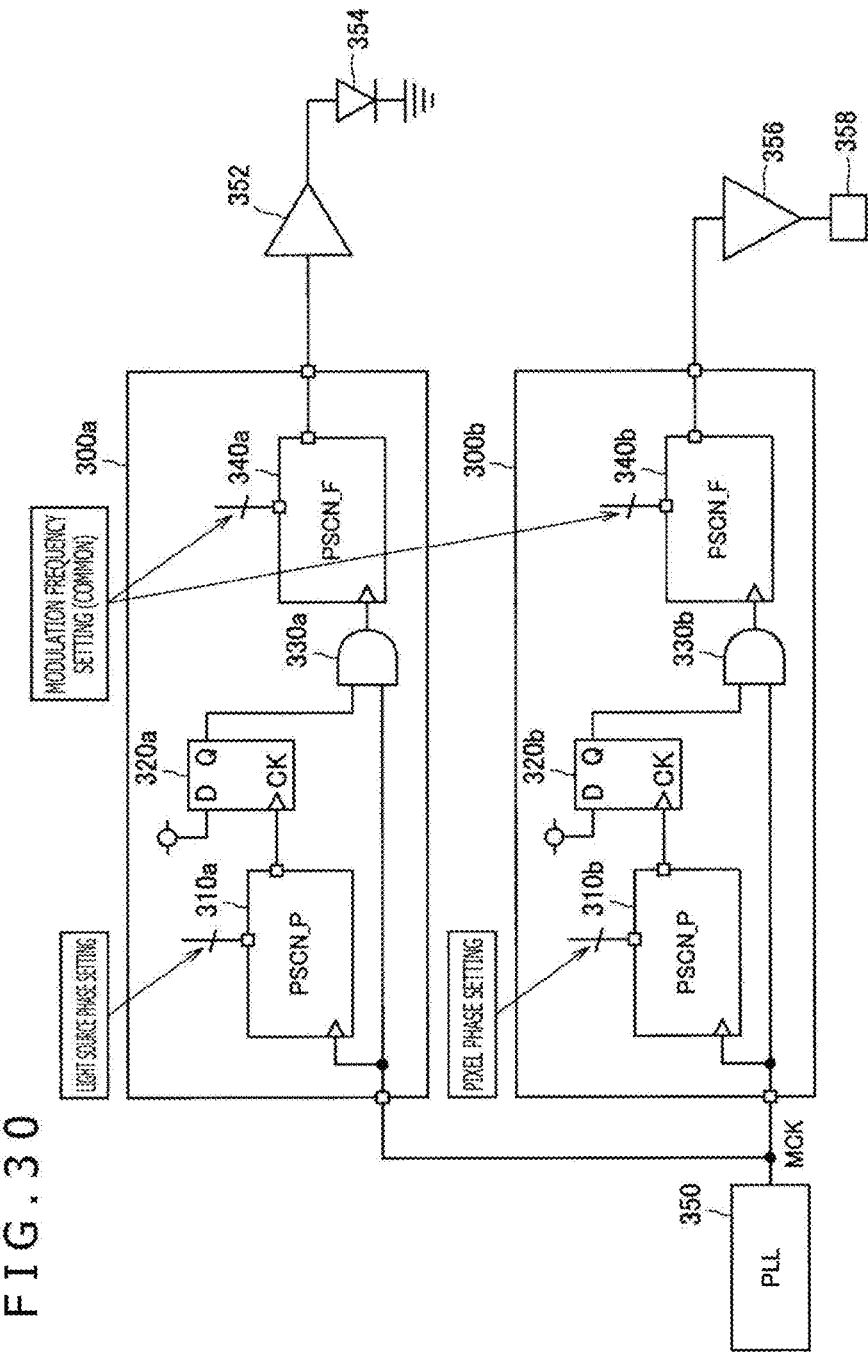
FIG. 30 is an explanatory view depicting a schematic configuration example of a distance image sensor.

FIG. 30 is an explanatory view depicting a schematic configuration example of a distance image sensor that uses the pulse generator according to the embodiment of the present disclosure. In FIG. 30, pulse generators 300a and 300b, a PLL 350, a light source driver 352, a light source 354, a pixel modulation driver 356 and a pixel 358 are depicted. The pixel 358 is a one-tap pixel in which one pixel includes one transistor.

A clock MCK outputted from the PLL 350 is sent to the pulse generators 300a and 300b. Further, to the pulse generator 300a, a phase setting for the light source 354 is inputted, and to the pulse generator 300b, a phase setting for the pixel 358 is inputted. In particular, in order to set a phase difference between a signal outputted from the pulse generator 300a (light source outputting signal) and a signal outputted from the pulse generator 300b (pixel modulation signal), individually unique phase settings are inputted to the pulse generators 300a and 300b. Further, a common modulation frequency setting is inputted to the pulse generators 300a and 300b. Consequently, pulses of a same frequency are outputted from the pulse generators 300a and 300b.

Figure 31:
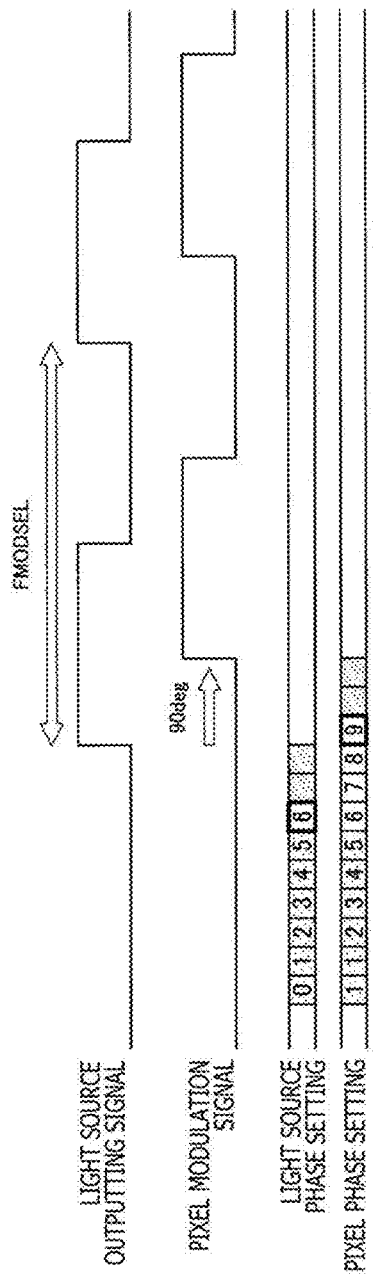
FIG. 31 is an explanatory view depicting an example of phase setting.

FIG. 31 is an explanatory view depicting an example of signals outputted from the pulse generators 300a and 300b and phase settings inputted to the pulse generators 300a and 300b. In the example depicted in FIG. 31, a light source phase setting inputted to the pulse generator 300a is a setting by which, when the count value of the counter 310a becomes "6," the output of the D-type flip-flop 320a switches from low to high. Further, in the example depicted in FIG. 31, the pixel phase setting inputted to the pulse generator 300b is a setting by which, when the count value of the counter 310b becomes "9," the output of the D-type flip-flog 320b switches from low to high. By such settings, the phase difference between the light source outputting signal outputted from the pulse generator 300a and the pixel modulation signal outputted from the pulse generator 300b can be set to 90 degrees.

Figure 32:
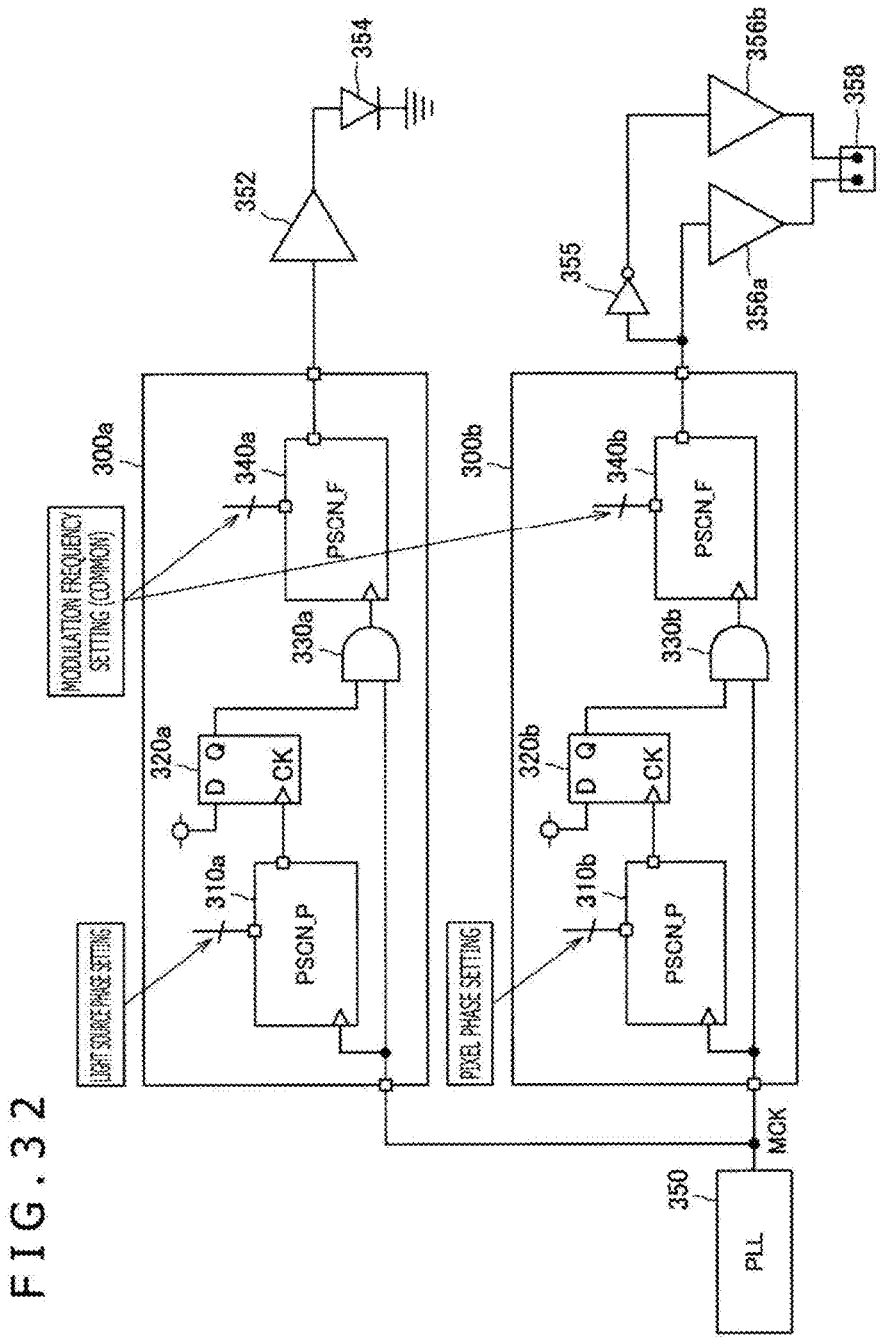
FIG. 32 is an explanatory view depicting a schematic configuration example of a distance image sensor.

Another example is described. FIG. 32 is an explanatory view depicting a schematic configuration example of a distance image sensor that uses the pulse generator according to the embodiment of the present disclosure. In FIG. 32, pulse generators 300a and 300b, a PLL 350, a light source driver 352, a light source 354, an inverter 355, pixel modulation drivers 356a and 356b and a pixel 358' are depicted. The pixel 358' is a two-tap pixel in which two transistors are provided in one pixel and is configured such that a signal from the pulse generator 300b is inputted to the transistors.

In the example depicted in FIG. 32, in order to set a phase difference between a signal to be outputted from the pulse generator 300a (light source outputting signal) and a signal to be outputted from the pulse generator 300b (pixel modulation signal), individually unique phase settings are inputted to the pulse generators 300a and 300b similarly as in the example depicted in FIG. 30. Further, to the pulse generators 300a and 300b, a common modulation frequency setting is inputted. Further, in the example depicted in FIG. 32, the output of the pulse generator 300b is branched into two, one of which is outputted as it is to the pixel modulation driver 356a and the other of which is inverted by the inverter 355 and then outputted to the pixel modulation driver 356b. Consequently, from an output signal from the pulse generator 300b, two signals having phases different by 180 degrees from each other (pixel modulation signals A and B) are generated.

Figure 33:
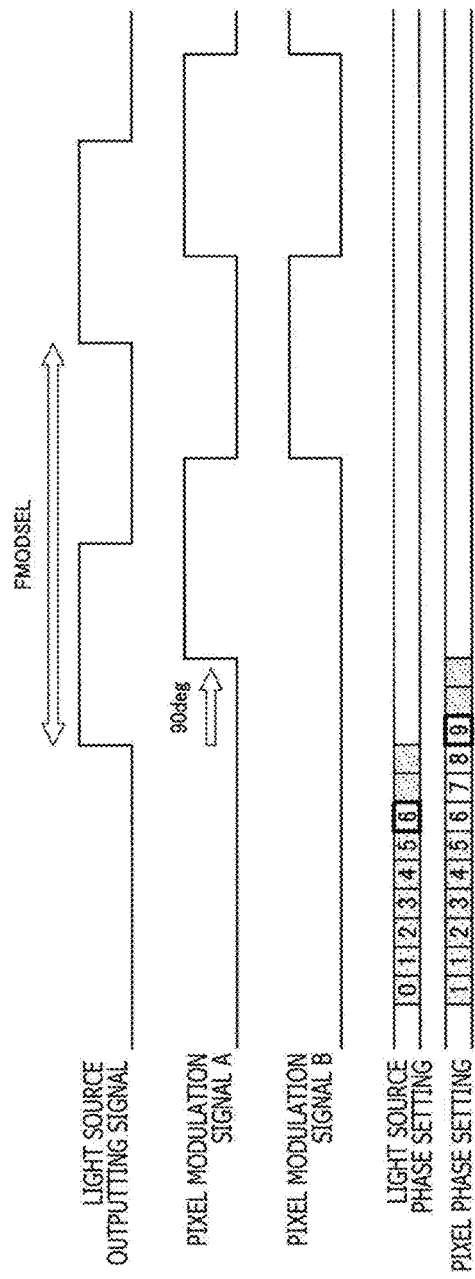
FIG. 33 is an explanatory view depicting another example of phase setting.

FIG. 33 is an explanatory view depicting an example of signals outputted from the pulse generators 300a and 300b and phase settings inputted to the pulse generators 300a and 300b. In the example depicted in FIG. 33, the light source phase setting inputted to the pulse generator 300a is a setting by which, when the count value of the counter 310a becomes "6," the output of the D-type flip-flop 320a switches from low to high. Further, in the example depicted in FIG. 33, the pixel phase setting inputted to the pulse generator 300b is a setting by which, when the count value of the counter 310b becomes "9," the output of the D-type flip-flop 320b switches from low to high. By such settings, the phase difference between the light source outputting signal to be outputted from the pulse generator 300a and the pixel modulation signal A to be outputted from the pulse generator 300b can be set to 90 degrees. Then, since the output of the pulse generator 300b is branched into two and one of the two branch outputs is inverted by the inverter 355 and then outputted to the pixel modulation driver 356b, the phase difference between the pixel modulation signal A and the pixel modulation signal B can be set to 180 degrees.

Figure 34:
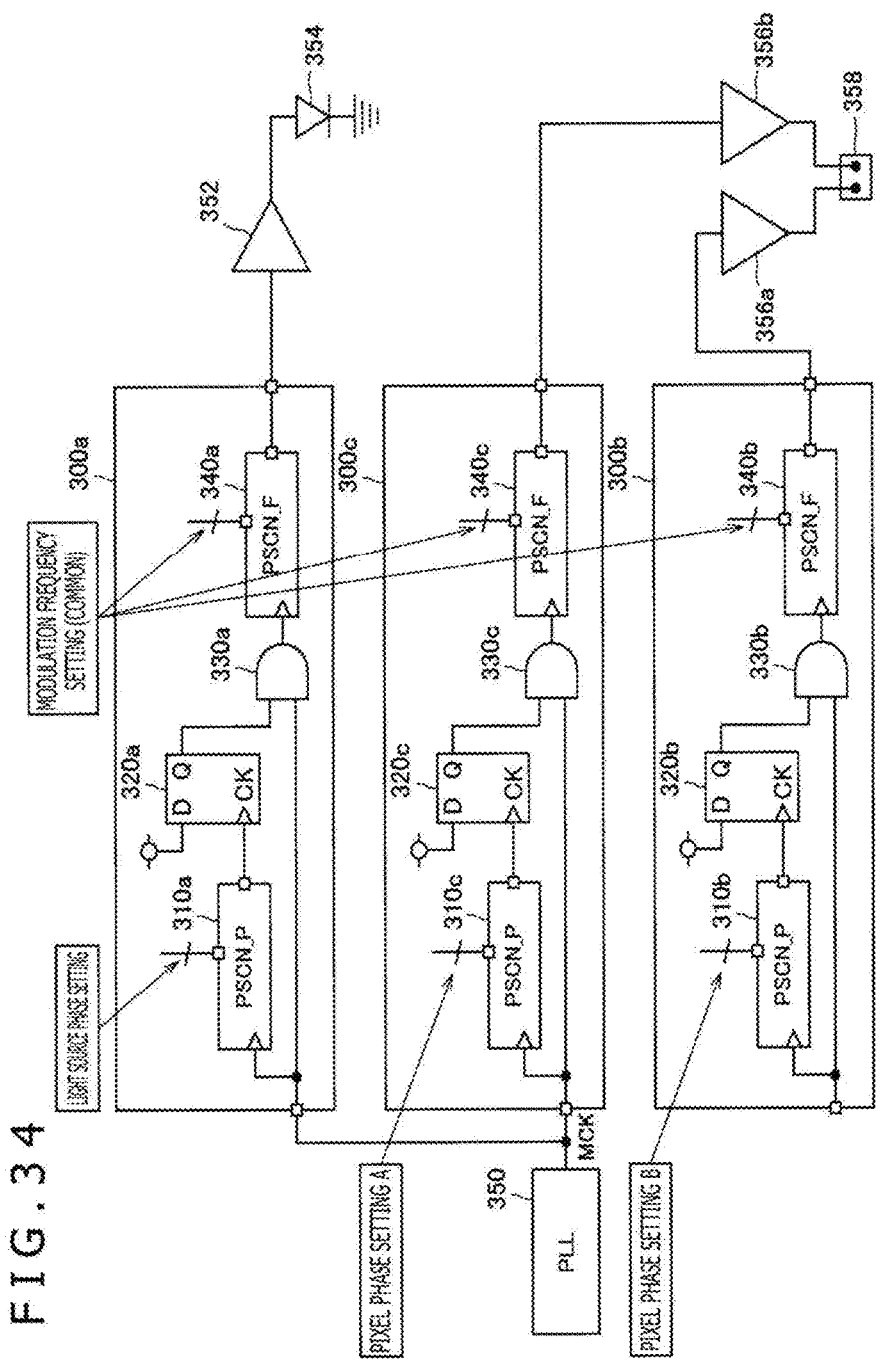
FIG. 34 is an explanatory view depicting a schematic configuration example of the distance image sensor.

A different example is described. FIG. 34 is an explanatory view depicting a schematic configuration example of a distance image sensor that uses the pulse generated according to the embodiment of the present disclosure. In FIG. 34, pulse generators 300a, 300b and 300c, a PLL 350, a light source driver 352, a light source 354, pixel modulation drivers 356a and 356b and a pixel 358'. The pixel 358' is a two-tap pixel in which two transistors are provided in one pixel and is configured such that signals from the pulse generator 300b are inputted to the transistors.

The example depicted in FIG. 34 is not different from the configuration example depicted in FIG. 32 in that a signal from the pulse generator 300a (light source outputting signal) is outputted to the light source 354. On the other hand, the example depicted in FIG. 34 is different from the configuration example depicted in FIG. 32 in that a signal to be outputted from the pixel 358' is generated by the pulse generators 300b and 300c. In particular, in order to set the phase difference among a signal to be outputted from the pulse generator 300a (light source outputting signal), a signal to be outputted from the pulse generator 300b (pixel modulation signal A) and a signal to be outputted from the pulse generator 300c (pixel modulation signal B), individually unique phase settings are inputted to the pulse generators 300a, 300b and 300c.

Figure 35:
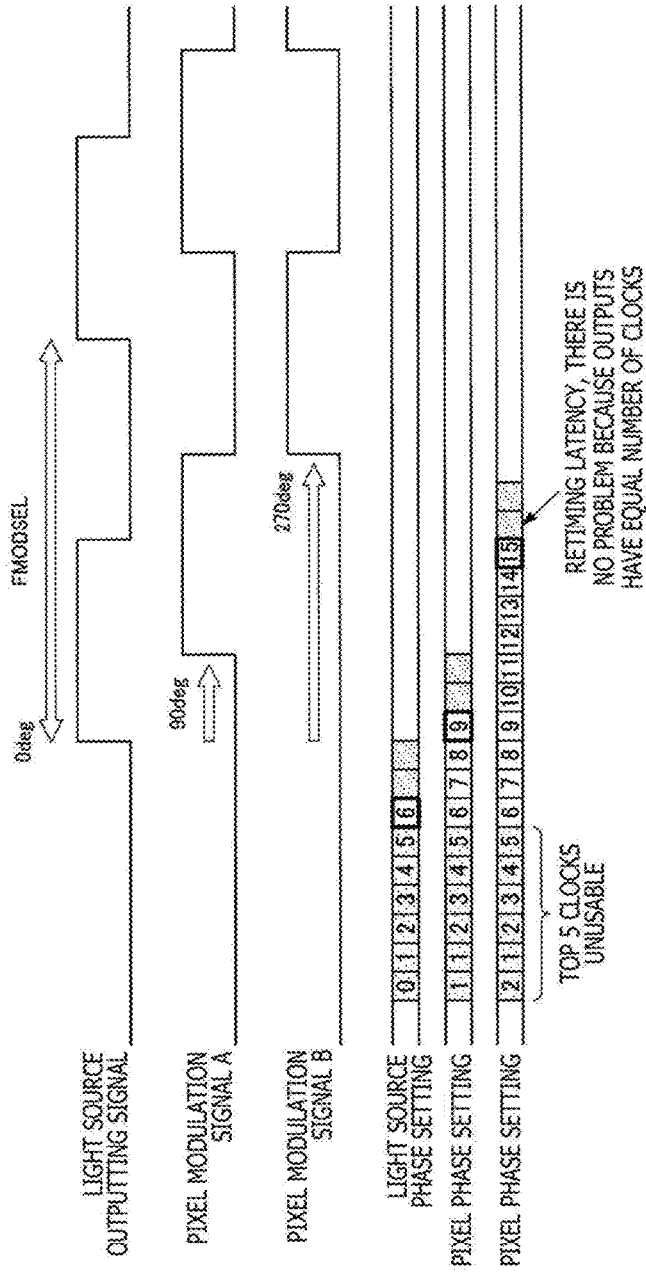
FIG. 35 is an explanatory view depicting an example of phase setting.

FIG. 35 is an explanatory view depicting an example of signals outputted from the pulse generators 300a, 300b and 300c and phase settings inputted to the pulse generators 300a and 300b. In the example depicted in FIG. 35, the light source phase setting to be inputted to the pulse generator 300a is a setting by which, when the count value of the counter 310a becomes "6," the output of the D-type flip-flop 320a switches from low to high. Further, in the example depicted in FIG. 35, the pixel phase setting to be inputted to the pulse generator 300b is a setting by which, when the count value of the counter 310b becomes "9," the output of the D-type flip-flop 320b switches from low to high. Further, in the example depicted in FIG. 35, the pixel phase setting to be inputted to the pulse generator 300c is a setting by which, when the count value of the counter 310c becomes "15," the output of the D-type flip-flop 320c switches from low to high. By such settings, the phase difference between the light source outputting signal to be outputted from the pulse generator 300a and the pixel modulation signal A to be outputted from the pulse generator 300b can be set to 90 degrees. Further, the phase difference between the light source outputting signal to be outputted from the pulse generator 300a and the pixel modulation signal B to be outputted from the pulse generator 300c can be set to 270 degrees.

Figure 36:
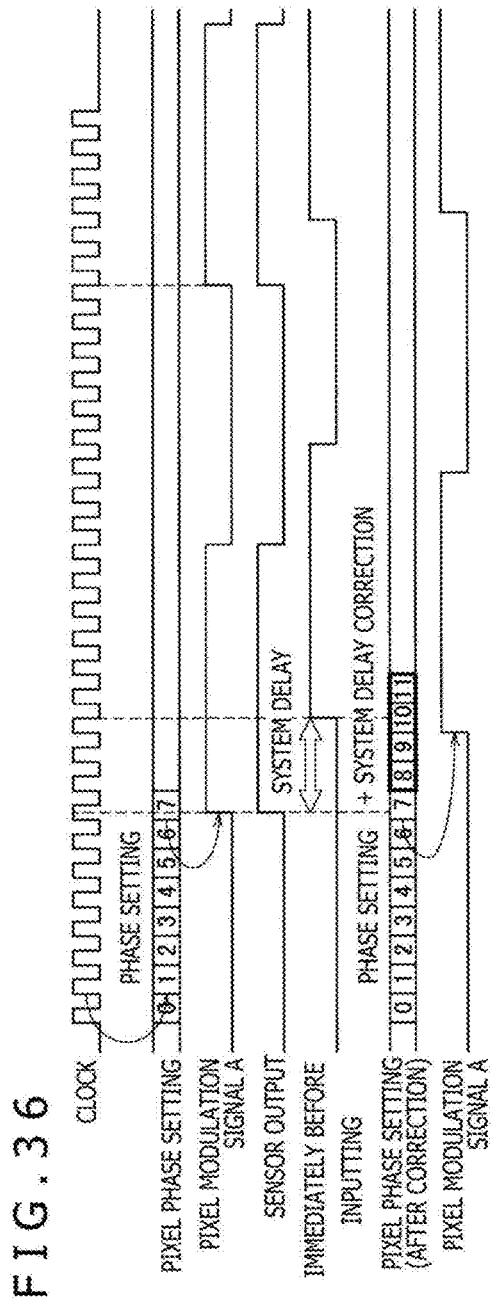
FIG. 36 is an explanatory view depicting an example of a signal outputted from a pulse generator and a phase setting inputted to the pulse generator.

By the configuration in which the pixel phase settings are inputted to the pulse generators in this manner, a system delay can be corrected. The system delay here is a delay of time after a pixel modulation signal is outputted from a pulse generator until the pixel modulation signal is actually inputted to a pixel. FIG. 36 is an explanatory view depicting an example of a signal outputted from a pulse generator and a phase setting inputted to the pulse generator. As depicted in FIG. 36, by providing an offset to a pixel phase setting to be inputted to a pulse generator for a pixel, the offset can be added to the pixel modulation signal without changing the setting of the pixel phase setting to be inputted to a pulse generator for a light source. In other words, by adjusting at least any one of the pulse generator for a light source or the pulse generator for a pixel, calibration for synchronizing a light source driver and a pixel modulation driver with each other can be achieved.

A distance image sensor that includes the pulse generator according to the present embodiment makes operation in a high frequency, for example, in a frequency of, for example, approximately 100 MHz, possible. An existing distance image sensor of the ToF system operates with a low frequency of, for example, approximately 20 MHz. In the case of operation of approximately 20 MHz, even if a displacement of two to three nsec or the like exists between driving of a light source and driving of a pixel, the influence of the displacement is small. However, in the case of operation of approximately 100 MHz, if a displacement by two nsec occurs, then this makes a loss of 25% and the influence of this is large. Since a distance image sensor that includes the pulse generator according to the present embodiment allows unique setting of a light source phase setting and a pixel phase setting, calibration for synchronizing a light source driver and a pixel modulation driver becomes possible by adjusting at least any one of the pulse generator for a light source or the pulse generator for a pixel as described above.

Figure 37:
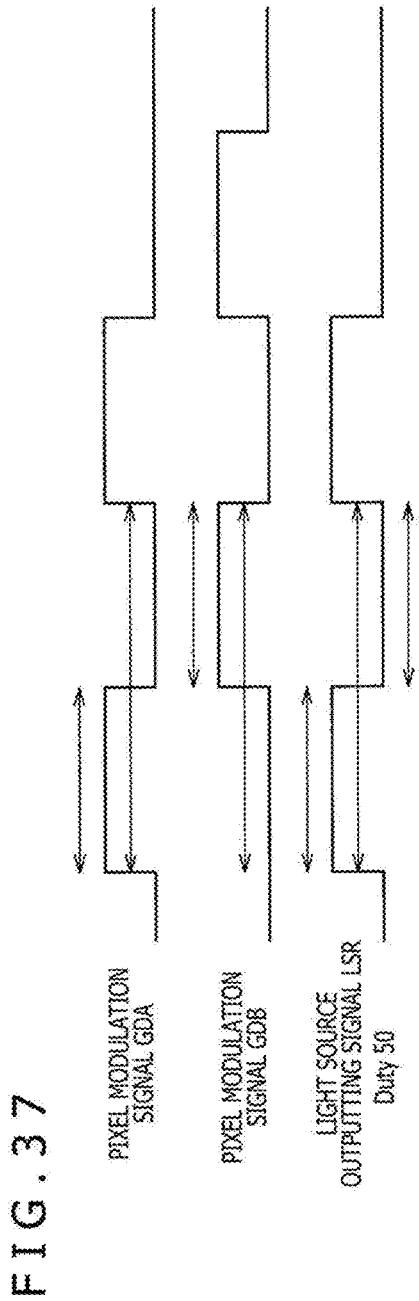
FIG. 37 is an explanatory view depicting an example of a waveform of a light source output signal generated by the pulse generator 300 and having a duty of 50%.

Subsequently, a distance image sensor of the ToF system that can set the duty of a light source to an arbitrary value is described. As described above, the pulse generator 300 generates a light source outputting signal having a duty of 50%. FIG. 37 is an explanatory view depicting an example of a waveform of a light source outputting signal generated by the pulse generator 300 and having a duty of 50%.

Figure 38:
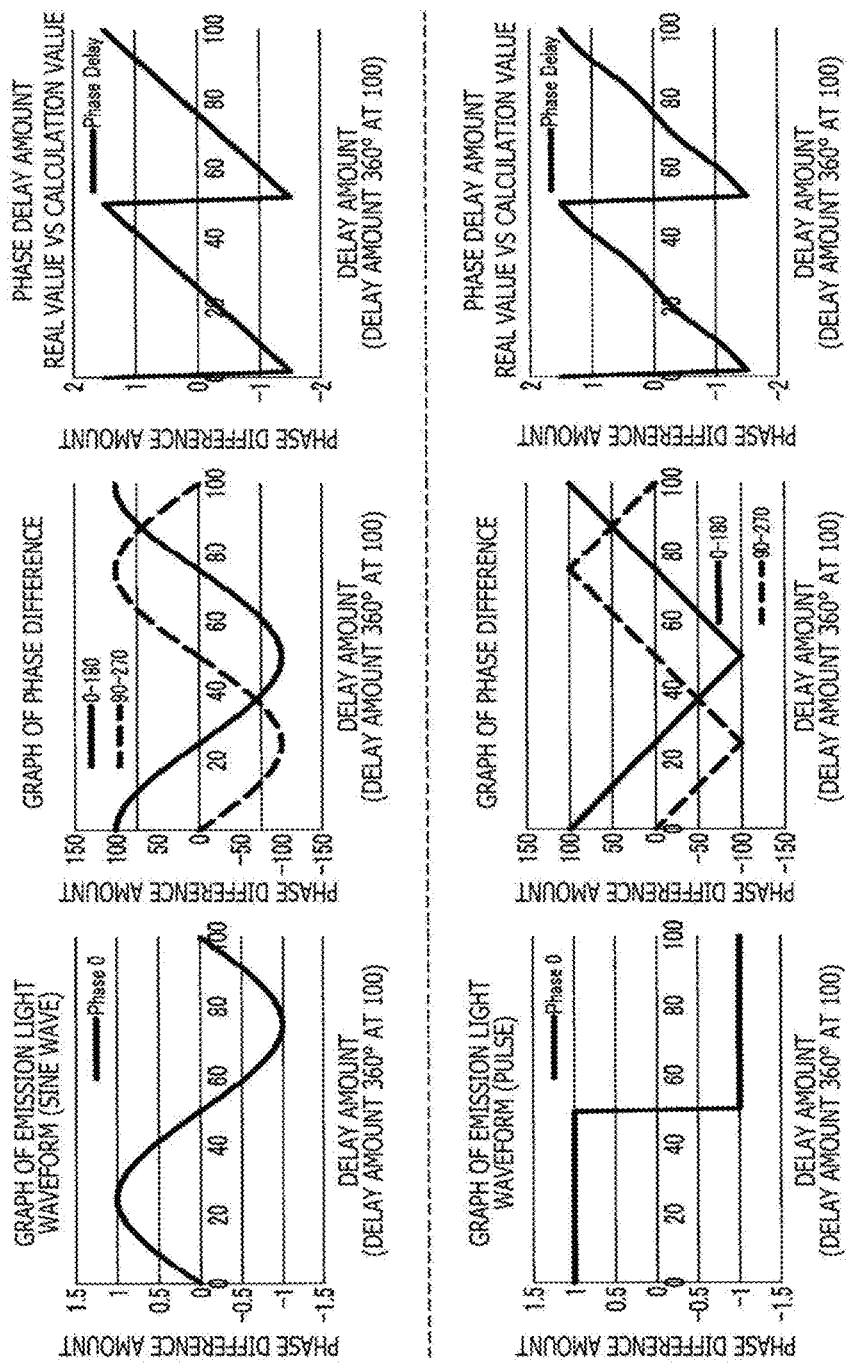
FIG. 38 is an explanatory view depicting a manner in which a distance measurement error is caused by a cyclic error.

However, if light is emitted on the basis of the light source outputting signal whose duty is 50%, then a cyclic error based on a distance measurement principle (continuous method) occurs, and a distance measurement error can be caused by this cyclic error. FIG. 38 is an explanatory view depicting a manner in which a distance measurement error is caused by a cyclic error. The upper stage indicates a manner in the case where the waveform of light emitted from the light source is a sine wave, and the lower stage indicates a manner in the case where the waveform of light emitted from the light source is a square wave. In the graphs, the axis of abscissa indicates the delay amount such that, when the value of the delay amount is 100, the delay amount is 360 degrees. In the continuous method, calculation is performed assuming that the signal is an ideal sine wave. In the case where light is emitted in accordance with a light source outputting signal of a sine wave, no distortion occurs with the phase delay amount as in the case of the graph on the upper right side. On the other hand, in the case where light is emitted in accordance with a light source outputting signal of a square wave, some distortion occurs with the phase delay amount as in the case of the graph on the lower right side. This distortion directly makes a cause of degrading the linearity of distance measurement. Although an existing distance image sensor deals with this cause by correcting the distortion by software, since the error by a cyclic error increases as the distance increases in distance measurement, the influence of the distortion increases.

Therefore, the discloser of the present case has conducted an intensive study about the technology that is used in a ToF camera system that especially adopts the indirect system and can reduce the distance measurement error by a cyclic error with a simple configuration. As a result, the discloser of the present case has invented a technology that is used in a ToF camera system that especially adopts the indirect system and can reduce the distance measurement error by a cyclic error with a simple configuration.

Figure 39:
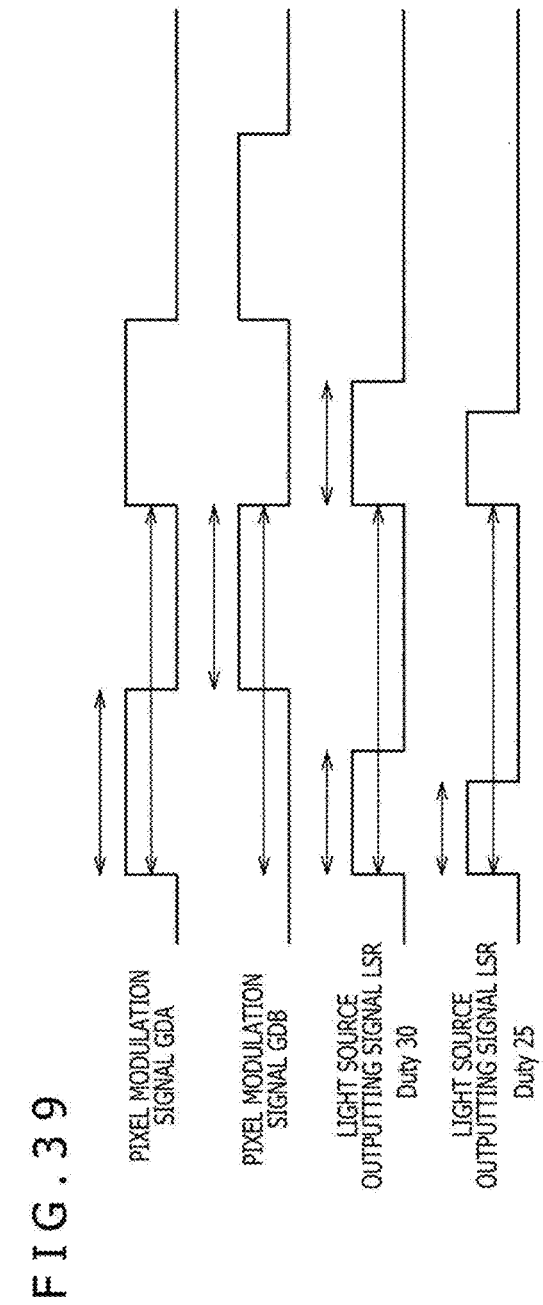
FIG. 39 is an explanatory view depicting an example of a waveform of light source output signals where the duty is 30% and 25% lower than 50%.

The distance image sensor according to the present embodiment reduces the cyclic error by changing the duty of the light source outputting signal, particularly by decreasing the duty of the light source outputting signal to less than 50%. To this end, the distance image sensor according to the present embodiment includes a pulse generator that generates a light source outputting signal whose duty is decreased to less than 50%. FIG. 39 is an explanatory view depicting an example of waveforms of light source outputting signals having duties of 30% and 25% less than 50%.

Figure 40:
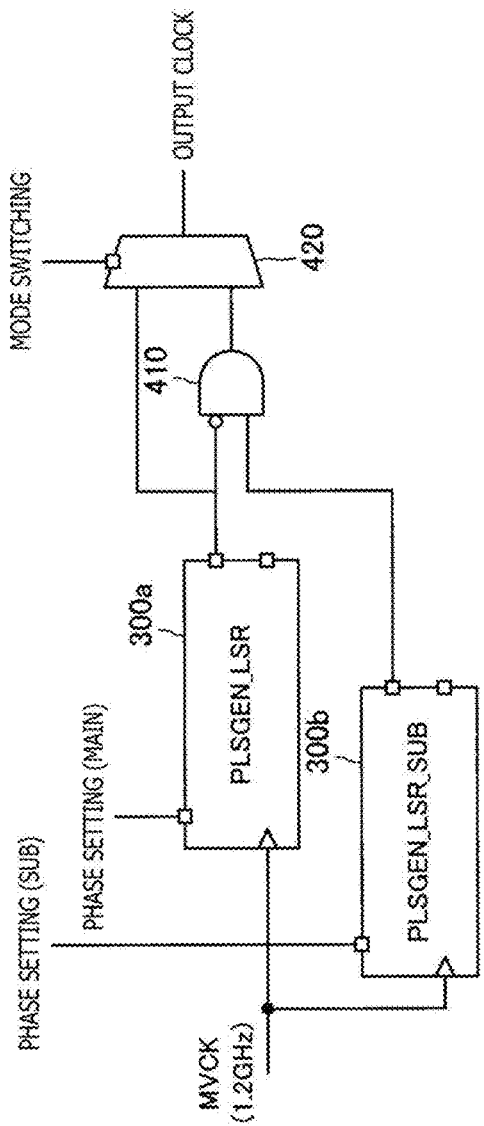
FIG. 40 is an explanatory view depicting a configuration example for outputting a light source outputting signal in a distance image sensor.

A configuration for outputting light source outputting signals having duties of 30% and 25% less than 50% in this manner is described. FIG. 40 is an explanatory view depicting a configuration example for outputting a light source outputting signal in the distance image sensor according to the embodiment of the present disclosure. In FIG. 40, pulse generators 300a and 300b, an AND gate 410 for ANDing (logically ANDing) with an output of the pulse generator 300a and an output of the pulse generator 300b after the output of the pulse generator 300a inverted, and a selector 420 are depicted. Both of the pulse generators 300a and 300b generate a signal for causing a light source to emit light.

The pulse generator 300a is a pulse generator for the object of generating a light source outputting signal whose duty is 50%. Meanwhile, the pulse generator 300b is a pulse generator for the object of adjusting the phase setting to generate a light source outputting signal whose duty is made less than 50% by the combination of a signal generated by the pulse generator 300a and a signal generated by the pulse generator 300b.

Figure 41:
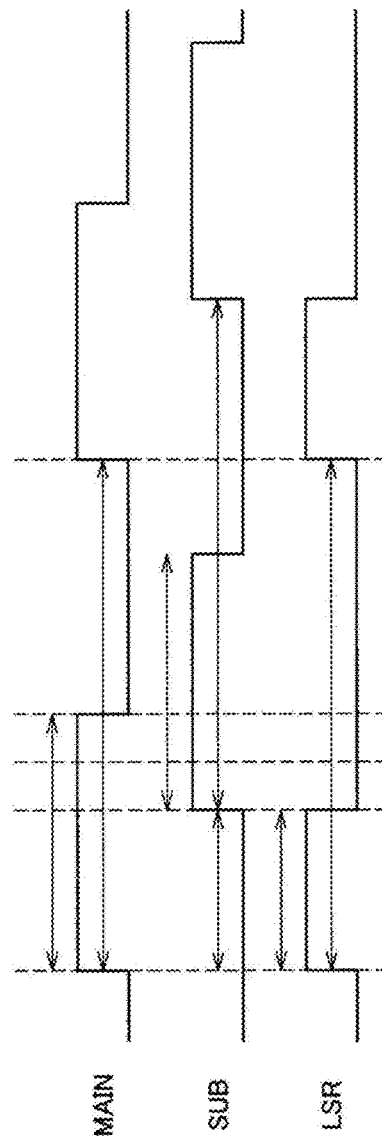
FIG. 41 is an explanatory view depicting an overview of generation of a light source outputting signal where the duty is set lower than 50%.

FIG. 41 is an explanatory view depicting an overview of generation of a light source outputting signal whose duty is made less than 50%. "MAIN" in FIG. 41 depicts an example of a waveform of a signal generated by the pulse generator 300a, and "SUB" depicts an example of a waveform of a signal generated by the pulse generator 300a. Further, "LSR" depicts an example of a waveform of a light source outputting signal whose duty is made less than 50% by the combination of the signal generated by the pulse generator 300a and the signal generated by the pulse generator 300b.

As depicted in FIG. 41, the waveform of the signal generated by the pulse generator 300a and the waveform of the signal generated by the pulse generator 300a have a phase difference therebetween. If, in this state, the signal generated by the pulse generator 300a is, after inverted, ANDed with the signal generated by the pulse generator 300b, then it is possible to generate a light source outputting signal whose duty is made less than 50% like "LSR."

The selector 420 selects and outputs any one of the output of the pulse generator 300a and the output of the AND gate 410. To the selector 420, a mode switching signal is supplied, and the selector 420 selects and outputs any one of the output of the pulse generator 300a, namely, a signal whose duty is 50%, and the output of the AND gate 410, namely, a signal whose duty is less than 50%, in response to the substance of the mode switching signal.

Where the distance image sensor of the ToF system according to the embodiment of the present disclosure has the configuration depicted in FIG. 40, it can cause the light source to emit light with different duties. Further, the distance image sensor of the ToF system according to the embodiment of the present disclosure can reduce the cyclic error by changing the duty of a light source outputting signal, particularly, by reducing the duty to less than 50%.

Figure 42:
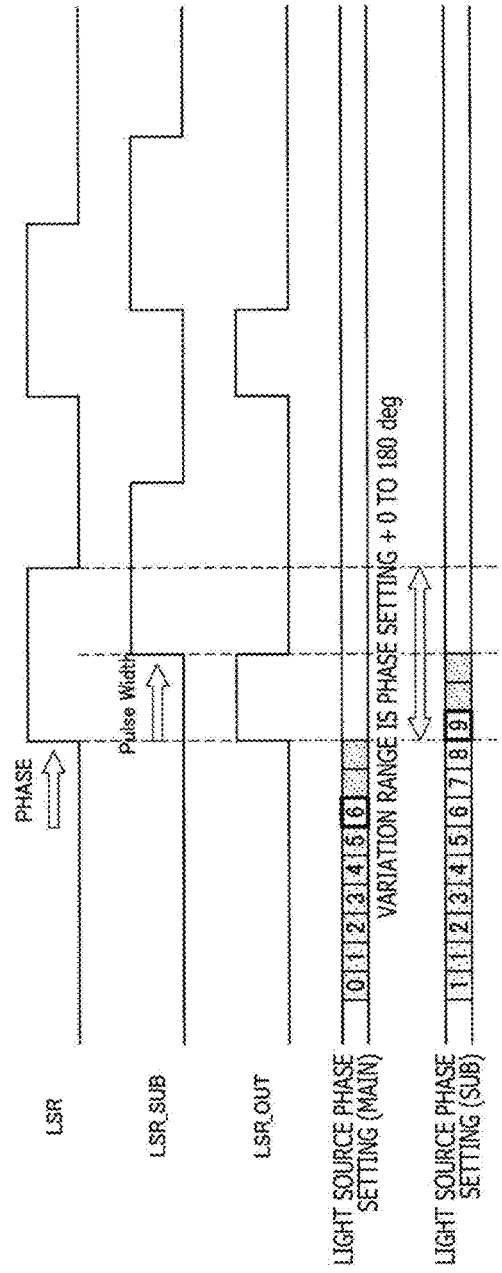
FIG. 42 is an explanatory view depicting an example of light source phase setting.

FIG. 42 is an explanatory view depicting an example of light source phase settings to be set to the pulse generators 300a and 300b. As depicted in FIG. 42, a phase difference can be provided between the waveform (LSR) of a signal generated by the pulse generator 300a and the waveform (LSR_SUB) generated by the pulse generator 300a by making the light source phase setting to be set to the pulse generator 300a and the light source phase setting to be set to the pulse generator 300b different from each other. Further, if the signal generated by the pulse generator 300a is logically ANDed, after the waveform thereof is inverted, with the signal generated by the pulse generator 300b, then it is possible to generate a light source outputting signal whose duty is made smaller than 50% like "LSR_OUT."

Figure 43:
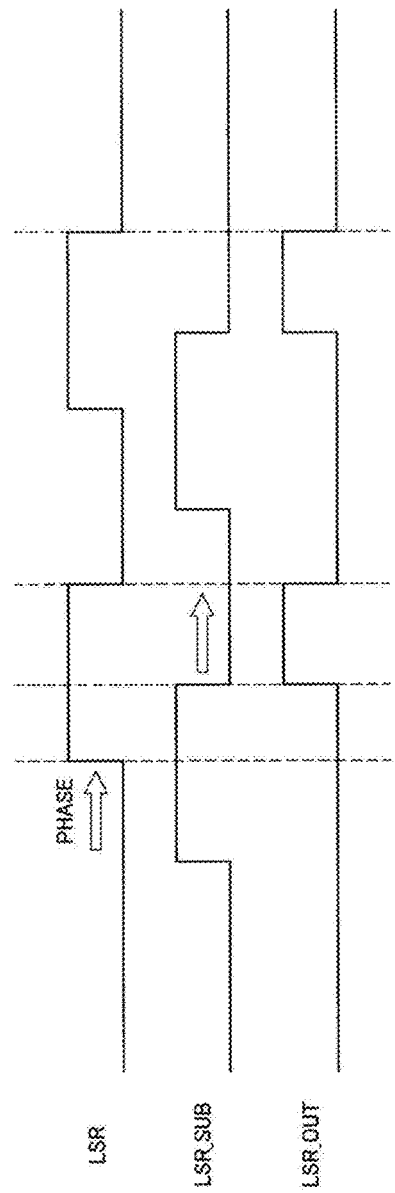
FIG. 43 is an explanatory view depicting an example of waveforms of signals.

Naturally, the phase of the signal generated by the pulse generator 300b may be advanced from the phase of the signal generated by the pulse generator 300a. FIG. 43 is an explanatory view depicting a waveform example of signals generated by the pulse generators 300a and 300b and light source outputting signals generated on the basis of the signals generated by the pulse generators 300a and 300b.

By switching and selecting signals of different duties to make light source outputting signals in this manner, for example, it is possible to cause a light source to emit light whose frequency is made different between a case in which the distance to an object at a long distance is measured and another case in which the distance to an object at a short distance is measured and make the duty smaller than 50% to reduce the cyclic error.

It is to be noted that, although the present example demonstrates an example in which the duty of a light source outputting signal is selected from between 50% and less than 50%, the present disclosure is not limited to such an example as just described.

Figure 44:
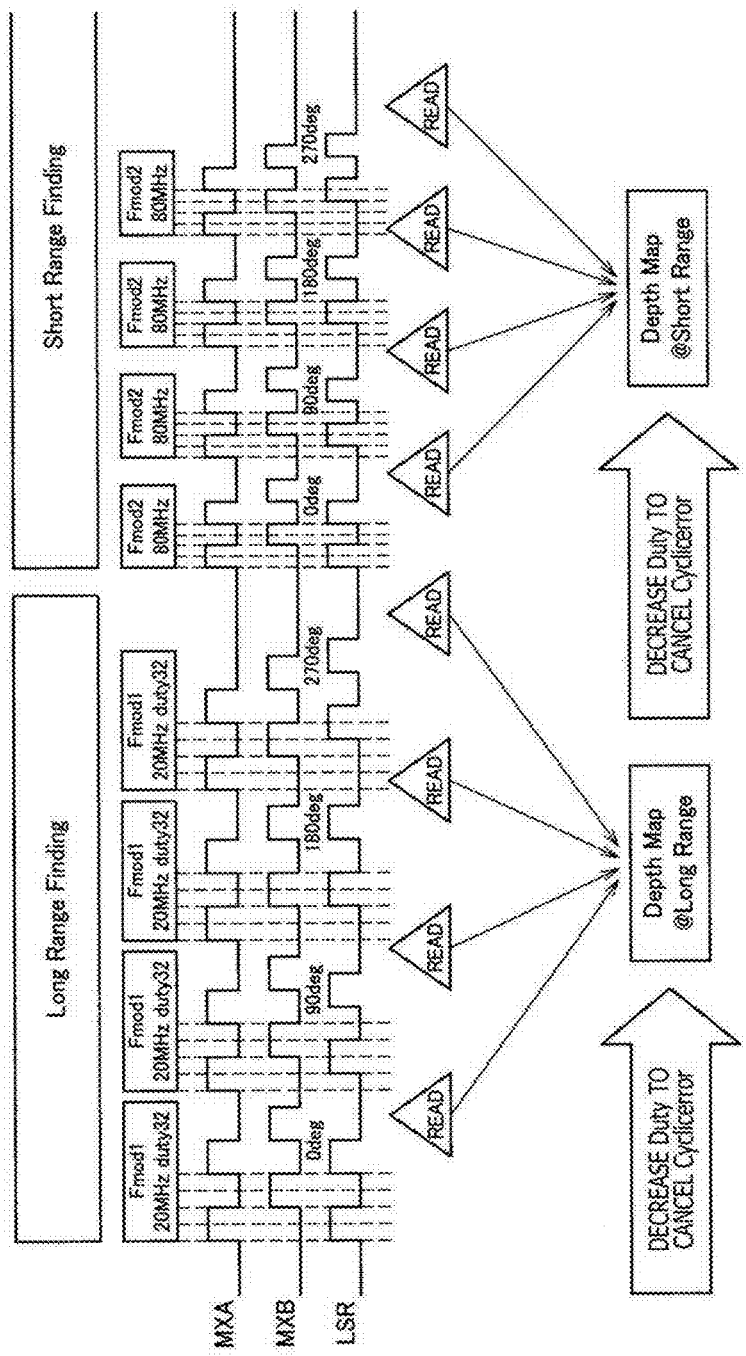
FIG. 44 is an explanatory view depicting a driving example of the distance image sensor.

FIG. 44 is an explanatory view depicting a driving example of a distance image sensor of the ToF system according to the embodiment of the present disclosure. What is depicted in FIG. 44 is an example in which the frequency and the duty of light emitted from a light source is made different between distance measurement of an object at a long distance and distance measurement of an object at a short distance.

In the example depicted in FIG. 44, upon distance measurement of an object at a long distance, light is emitted at a duty of 32% at a frequency of 20 MHz, but upon distance measurement of an object at a short distance, light is emitted at a duty of 32% at a frequency of 80 MHz. Then, in the example depicted in FIG. 44, in the distance measurement of the object at the long distance and the distance measurement of the object at the short distance, measurement is performed in the four phases of zero degrees, 90 degrees, 180 degrees and 270 degrees.

The distance image sensor of the ToF system according to the embodiment of the present disclosure can reduce the cyclic error by causing a light source to emit light in this manner.

Figure 45:
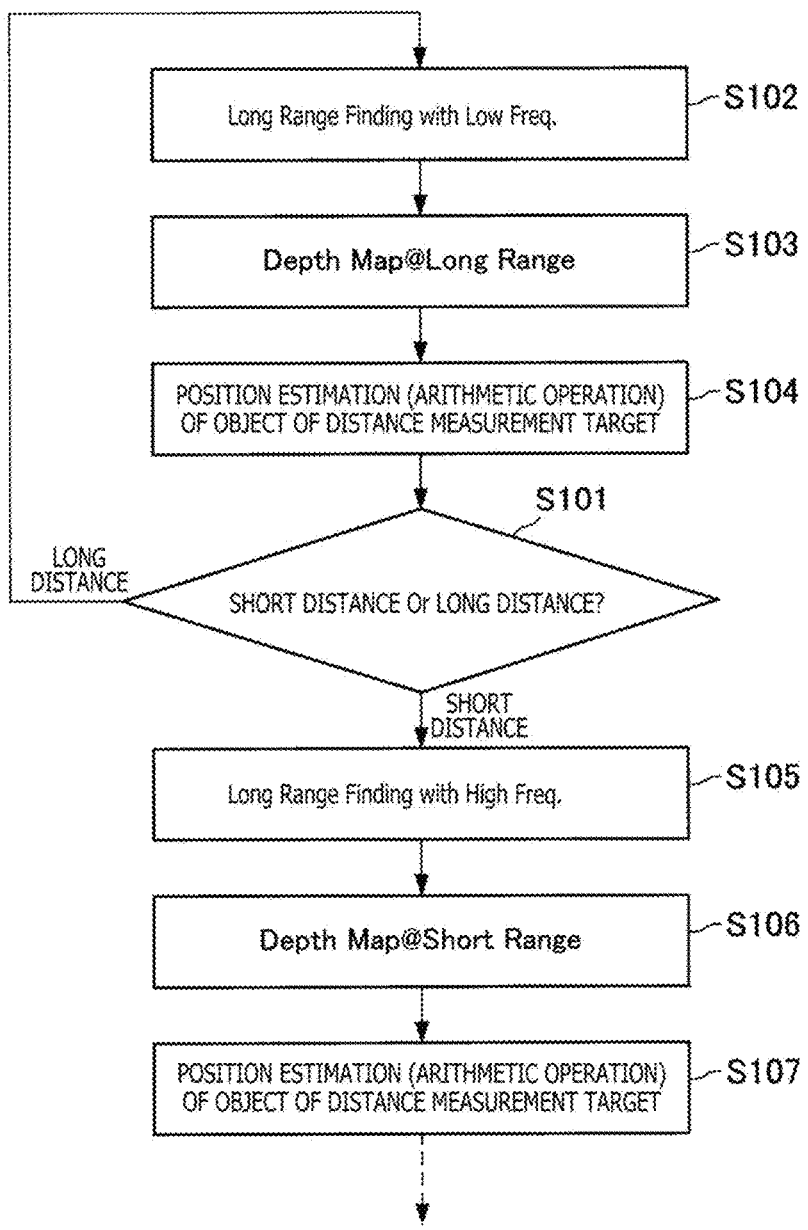
FIG. 45 is a flow chart depicting an operation example of the distance image sensor.

FIG. 45 is a flow chart depicting an operation example of the distance image sensor of the ToF system according to the embodiment of the present disclosure. The distance image sensor decides whether or not an object of a distance measurement target is at a long distance (long distance equal to or longer than a predetermined distance) (step S101). If the object is at a long distance, then the distance image sensor carries out distance measurement with a low frequency (step S102) and generates a depth map at the long distance (step S103). In this distance measurement, the distance image sensor causes the light source to emit light at a duty of less than 50%. Then, the distance image sensor estimates (arithmetically operates) the position of the object of the distance measurement target on the basis of the depth map at the long distance (step S104).

On the other hand, if the object of the distance measurement target is at a short distance, then the distance image sensor carries out distance measurement with a high frequency (step S105) and generates a depth map at the short distance (step S106). In this distance measurement, the distance image sensor causes the light source to emit light at a duty less than 50%. Then, the distance image sensor estimates (arithmetically operates) the position of the object of the distance mea surement on the basis of the depth map at the short distance (step S107).

In this manner, the distance image sensor of the ToF system according to the embodiment of the present disclosure can cause, when it causes light to be emitted from the light source, the light source to emit light at a duty different depending upon the setting. Thereupon, by causing the light source to emit light at a duty less than 50%, the distance image sensor of the ToF system according to the embodiment of the present disclosure can reduce the influence of the cyclic error and increase the accuracy in distance measurement.

Subsequently, a distance image sensor of the ToF system that performs distance measurement by changing the setting of a modulation frequency in a single frame is described.

In a distance image sensor of the indirect ToF system, the modulation frequency and the distance measurement error have an inverse proportional relationship therebetween. Although it is necessary to increase the modulation frequency in order to increase the accuracy to perform measurement, if the modulation frequency is increased, then the distance measurement range is reduced.

In an existing distance image sensor of the indirect ToF system, in the case where two different modulation frequencies are used to perform distance measurement, change of the setting of the modulation frequency is permitted only in cycles for accumulation into pixels and for reading out of the accumulated data. Therefore, in the case where distance measurement is performed using two different modulation frequencies, since frames necessary for depth calculation increases, the time until distance measurement completion increases. Further, if it is tried to change the setting of the modulation frequency during an accumulation period, then the dead time during setting transition becomes long and the ratio of invalid signals increases.

Figure 46:
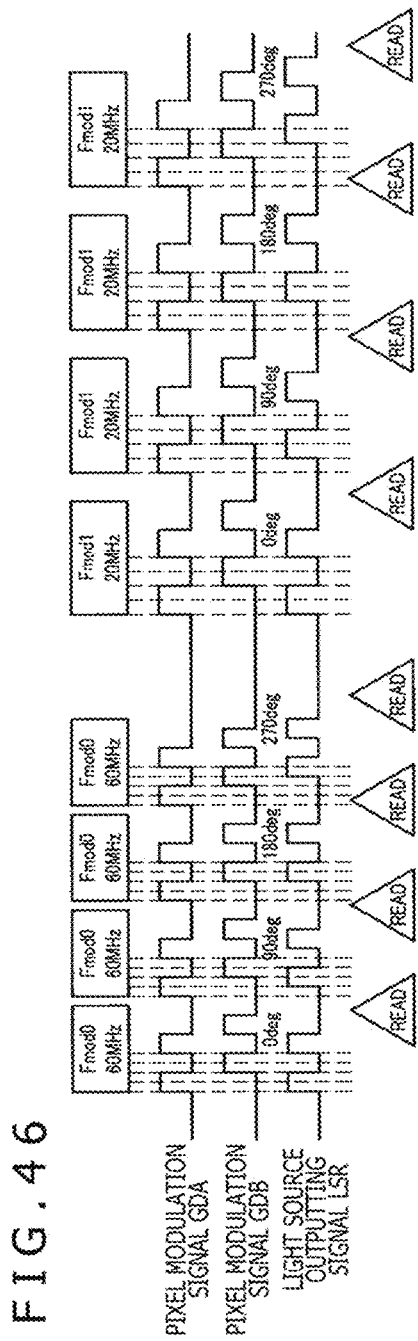
FIG. 46 is an explanatory view depicting an operation example of a distance image sensor of an indirect ToF type.

FIG. 46 is an explanatory view depicting an operation example of a distance image sensor of the indirect ToF system when distance measurement is performed using a same modulation frequency during an accumulation period in a single frame. In the example of FIG. 46, an example is depicted in which distance measurement is performed while the phase is changed at a modulation frequency of 60 MHz and then measurement is performed while the phase is changed at a modulation frequency of 20 MHz. In this case, in the case where the frequency is to be changed, although it is necessary to change the setting of the PLL, a period for stabilization of the PLL becomes required, and it is difficult to change the frequency immediately. Accordingly, time is required for switching of the modulation frequency, and the time before distance measurement completion becomes long.

Figure 47:
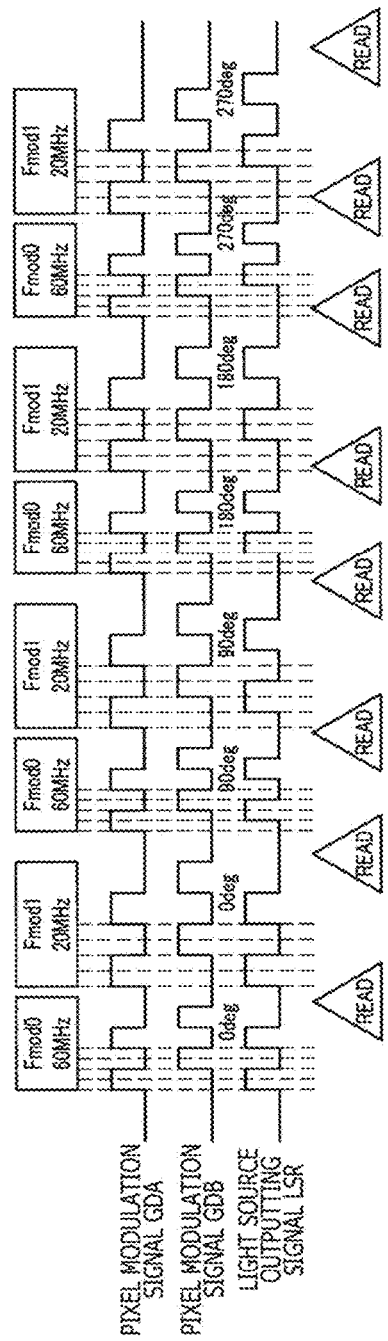
FIG. 47 is an explanatory view depicting an operation example of the distance image sensor of the indirect ToF type.

FIG. 47 is an explanatory view depicting an operation example of a distance image sensor of the indirect ToF system when distance measurement is performed using a same modulation frequency during an accumulation period in one frame. In the example of FIG. 47, an example is depicted in which, where one cycle includes distance measurement with a modulation frequency of 60 MHz and distance measurement with a modulation frequency of 20 MHz, distance measurement is performed while the phase is changed after one cycle comes to an end. In this case, time is required for switching of the modulation frequency, and the time before distance measurement completion becomes long. Further, also in regard to a reading out time number from pixels, eight times of reading out are required before distance measurement completion similarly as in the example depicted in FIG. 46.

Therefore, in the present embodiment, a distance image sensor of the indirect ToF system is demonstrated in which such a pulse generator in which two programmable counters are combined is used to change the setting of the modulation frequency in a short period of time during an accumulation period in a single frame and such change of the setting can be reflected. It is to be noted that the term frame designates a period after accumulation of the image sensor is started until reading out of the image sensor is completed.

Figure 48:
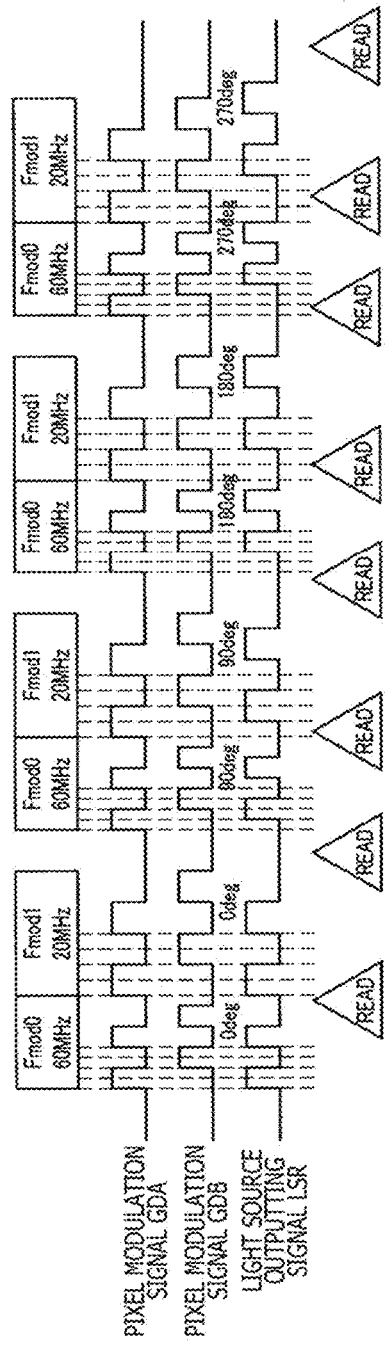
FIG. 48 is an explanatory view depicting an operation example of the distance image sensor of the indirect ToF type.

FIG. 48 is an explanatory view depicting a driving example of a distance image sensor of the indirect ToF system according to the embodiment of the present disclosure. In the present embodiment, during an accumulation period in a single frame, driving with the modulation frequencies of 60 MHz and 20 MHz is executed and results of the driving are acquired by a single time reading out operation from pixels. By driving with different modulation frequencies from each other during an accumulation period in a single frame in this manner, the distance image sensor of the indirect ToF system according to the embodiment of the present disclosure can reduce the reading out time number. Further, the distance image sensor of the indirect ToF system according to the embodiment of the present disclosure can save the reading out time and can improve the frame rate. It is to be noted that, although dead time occurs at a timing at which the setting of the modulation frequency is changed, the period of the dead time is very short in comparison with the period for the stabilization of the PLL described hereinabove.

Figure 49:
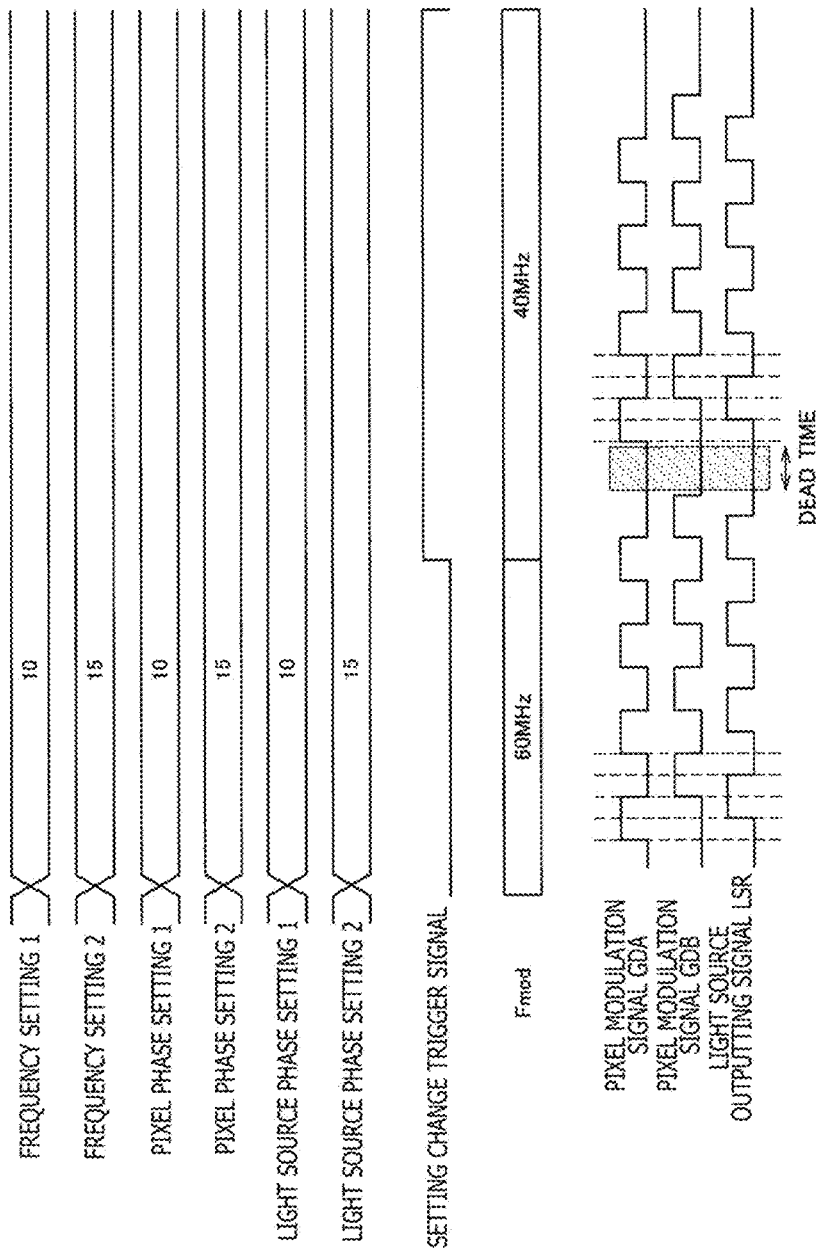
FIG. 49 is an explanatory view depicting a particular example of driving of the distance image sensor of the indirect ToF type.

FIG. 49 is an explanatory view depicting a particular example of driving of a distance image sensor of the indirect ToF system according to the embodiment of the present disclosure. In FIG. 49, an example is depicted in which, as the settings to the pulse generator 300 described above, two different settings are provided for each of the frequency setting, pixel phase setting and light source position setting. The reason why two kinds of phase setting are provided is that, if the modulation frequency changes, then also the setting of the phase changes naturally.

FIG. 49 further depicts a trigger signal for setting change. In the example of FIG. 49, in the case where the trigger is low, the modulation frequency is set to 60 MHz, and in the case where the trigger is high, the modulation frequency is set to 40 MHz. In other words, the setting to the pulse generator 300 switches depending upon the state of the trigger signal for setting change. Thereupon, if the pulse generator 300 detects that the state of the trigger signal for setting change has changed, then the pulse generator 300 resets the value of the counter and outputs a pulse based on the setting after the change. In the lower stage of FIG. 49, a manner is depicted in which the frequency of the pixel modulation signal and the light source outputting signal changes in response to a change of the trigger signal for setting change.

Figure 50:
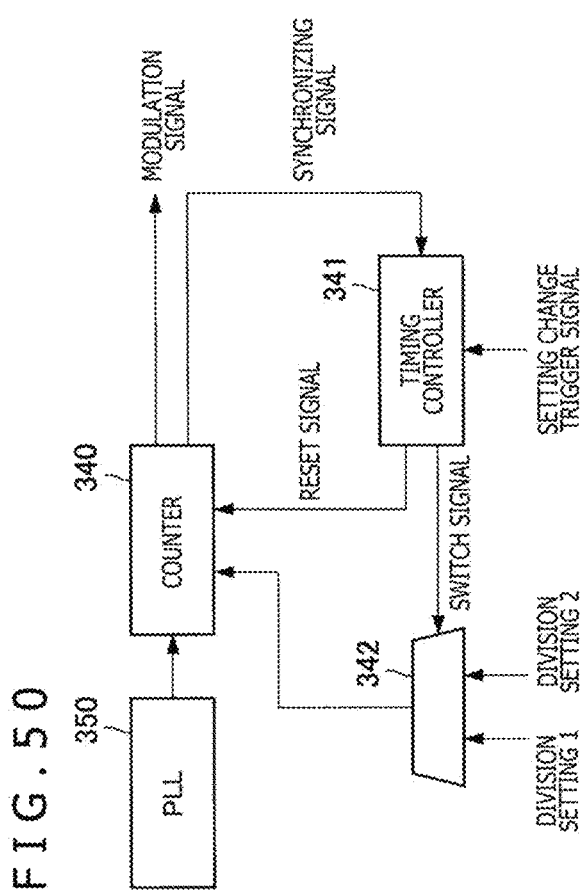
FIG. 50 is an explanatory view depicting an example of a configuration used in the distance image sensor of the indirect ToF type.

FIG. 50 is an explanatory view depicting an example of a configuration used in a distance image sensor of the indirect ToF system according to the embodiment of the present disclosure. In FIG. 50, a counter 340 for setting a modulation frequency, a PLL 350 that outputs a clock, a timing controller 341 that receives an output of the counter 340 as a synchronizing signal and a selector 342 for outputting the setting to the counter 340 are depicted.

The timing controller 341 detects a change of the state of the setting change trigger signal. If the timing controller 341 detects that the state of the setting change trigger signal has changed, then it outputs a switch signal to the selector 342 and outputs a rest signal for resetting the counter value to the counter 340 in order to switch the division setting. The selector 342 selects and outputs one of the two division settings on the basis of the switch signal from the timing controller 341.

For example, it is assumed that the timing controller 341 detects that, when the counter 340 is operating with the division setting 1, the state of the setting change trigger signal has changed. The timing controller 341 latches a setting change trigger signal with a synchronizing signal in the inside thereof and outputs a switch signal and a reset signal within a period within which the modulation signal is low. The selector 342 receiving the switch signal switches the output to the counter 340 from the division setting 1 to a division setting 2. Then, the counter 340 resets the counter value on the basis of the reset signal and starts counting with the division setting 2 to output a modulation signal on the basis of the division setting 2.

The present embodiment can provide a distance image sensor of the indirect ToF system that can change the setting of a modulation frequency in short time during an accumulation period of a single frame using a pulse generator that is a combination of two programmable counters and reflect the change of the setting as described above. By changing the setting of the modulation frequency in short time during an accumulation period in a single frame and reflecting the change of the setting, the distance image sensor of the indirect ToF system according to the embodiment of the present disclosure can reduce the reading out time number before distance measurement completion and reduction of the power consumption can be anticipated. Further, the distance image sensor of the indirect ToF system according to the embodiment of the present disclosure can complete distance measurement in a short period of time in comparison with that in an alternative case in which the setting of the modulation frequency is changed by changing the setting of the PLL. If a plurality of PLLs are provided, then although it is possible also to change the setting of the modulation frequency by switching between the PLLs, the provision of a plurality of PLLs leads to increase of the circuit scale. It is possible for the distance image sensor of the indirect ToF system according to the embodiment of the present disclosure to change the setting of the modulation frequency without increasing the circuit scale.

Since the distance image sensor of the indirect ToF system according to the embodiment of the present disclosure has such a configuration as depicted in FIG. 50, it can change the modulation frequency of the pixel modulation signal and the light source outputting signal by a change of the trigger signal for setting change. Further, the distance image sensor of the indirect ToF system according to the embodiment of the present disclosure can be driven with different modulation frequencies during an accumulation period in a single frame.

Subsequently, a distance image sensor of the indirect ToF system for avoiding erroneous distance measurement when a plurality of cameras measure the distance to a same target is described.

Figure 51:
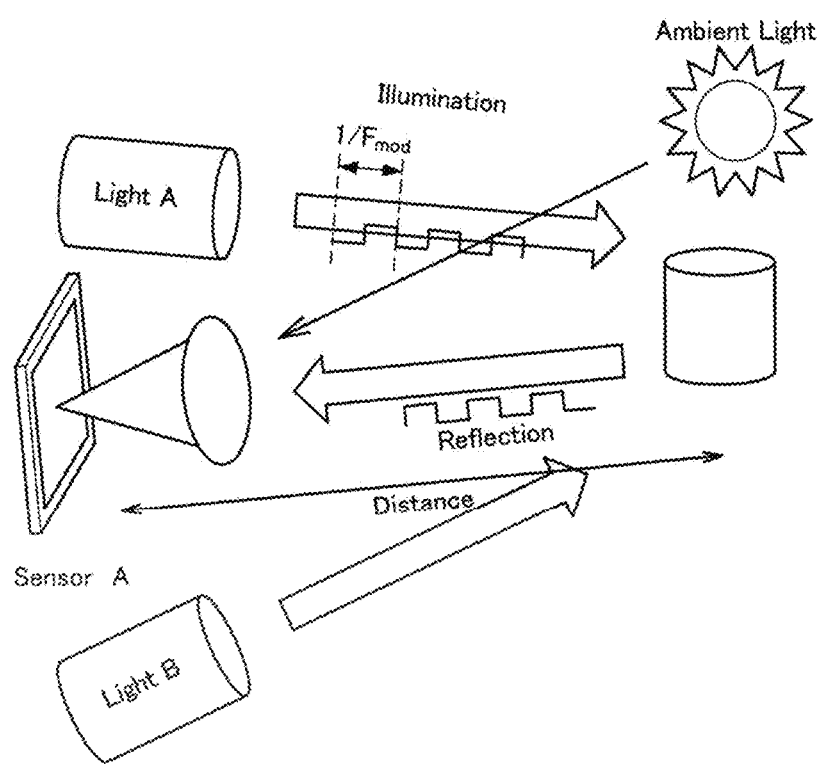
FIG. 51 is an explanatory view depicting a manner in which light is radiated from a plurality of light sources toward a same distance measurement target and a certain image sensor receives the light from them.
Figure 52:
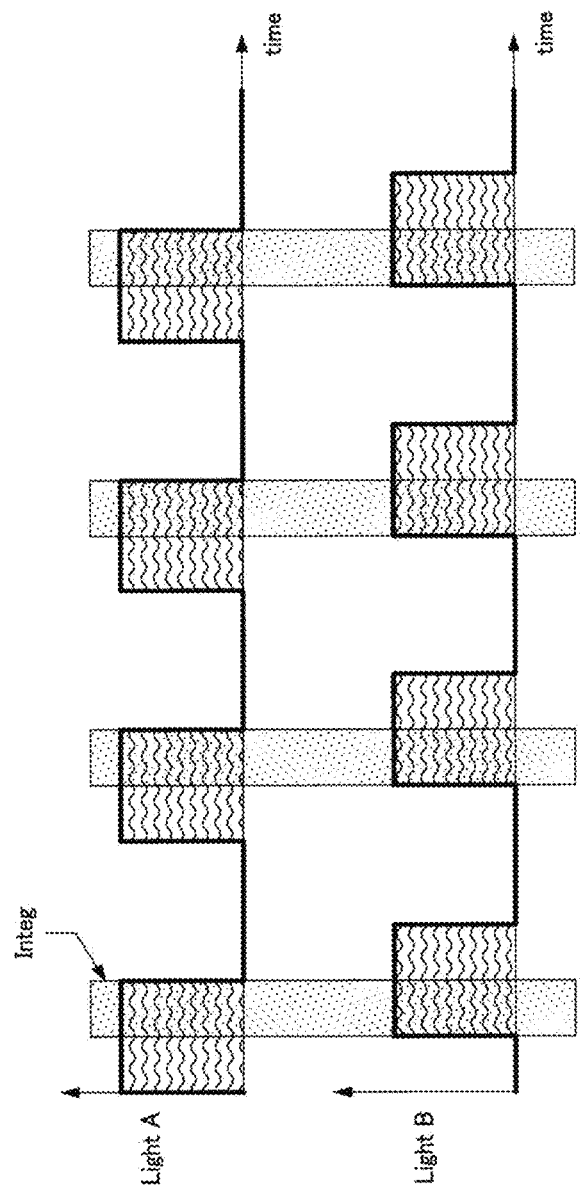
FIG. 52 is an explanatory view depicting a manner in which an overlap of light emission time (modulation time) occurs between a light source A and another light source B.

In an active distance measurement system, light is emitted from a light source and light reflected by an object of the distance measurement target is detected to perform distance measurement to the distance measurement target. In this active distance measurement system, if a plurality of cameras measure the distance to a same target, then signals of them mix up, which gives rise to erroneous distance measurement. FIG. 51 is an explanatory view depicting a manner in which light is irradiated from a plurality of light sources to a same distance measurement target and a certain image sensor receives the light from the plurality of light sources. Although originally it is desirable for the image sensor depicted in FIG. 51 to operate so as to receive light from a light source A, also it possibly occurs that the image sensor receives light from a different light source B. FIG. 52 is an explanatory view depicting a manner in which light emission time (modulation time) overlaps between the light source A and the light source B. If the light emission time overlaps between the light source A and the light source B in this manner, then the image sensor receives light from different light sources at the same time, which gives rise to contamination.

Figure 53:
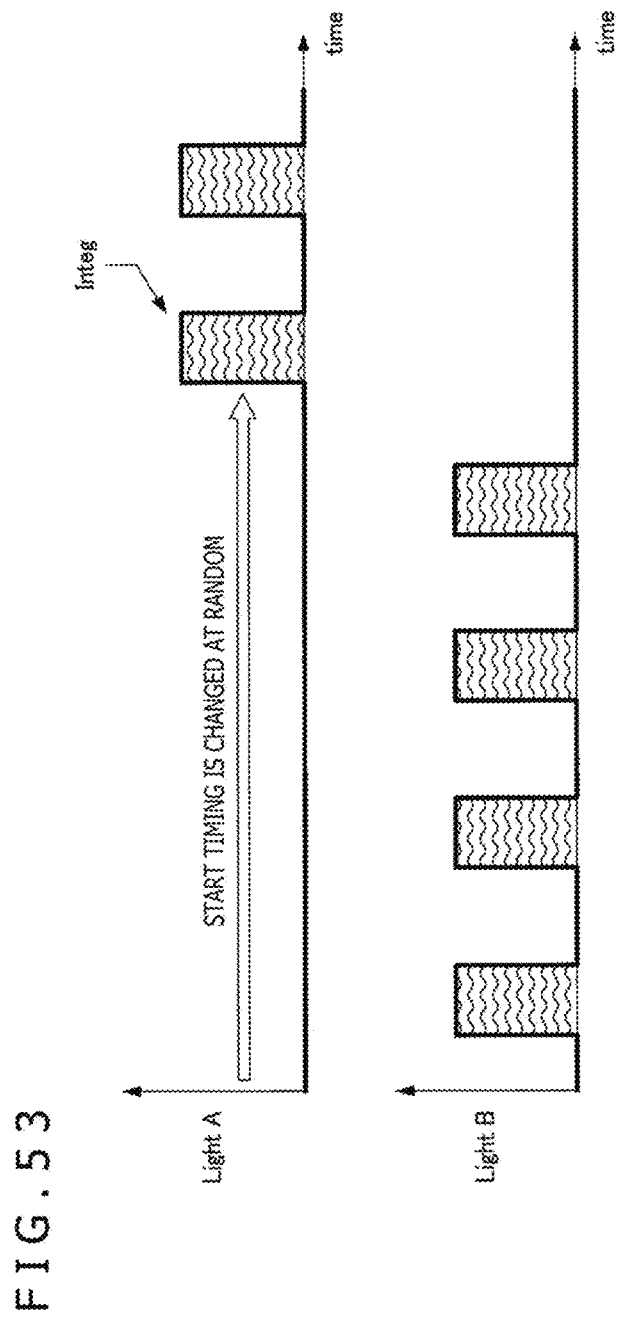
FIG. 53 is an explanatory view depicting a manner in which a light emission timing is displaced at random between the light source A and the light source B.

In the case where the distance to a same target is to be measured by a plurality of cameras in accordance with the active distance measurement system, a technique for decreasing the probability of such overlap by using a random number in the time direction for a light emission timing seems available. FIG. 53 is an explanatory view depicting a manner in which the light emission timings are displaced from each other at random between the light source A and the light source B. However, even if the light emission timings are displaced at random, it is difficult to fully prevent the overlap.

Therefore, in the present embodiment, the phase is inverted by 180 degrees using a toggle signal generated pseudo-randomly as a trigger to encrypt the modulation for interference prevention. Since, to a distance image sensor of the indirect ToF system according to the present embodiment, a modulation pattern of light to be received by an image sensor is known in advance, light modulated in a pattern different from the pattern can be handled as an invalid signal that does not contribute to distance measurement.

Figure 54:
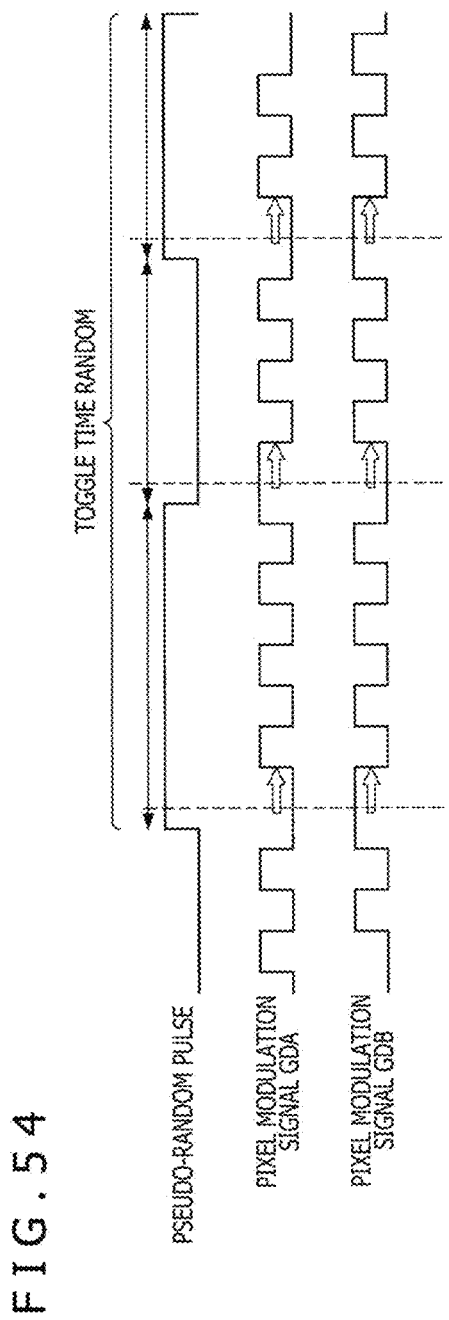
FIG. 54 is an explanatory view depicting an example of a pixel modulation signal.

FIG. 54 is an explanatory view depicting an example of a pixel modulation signal that can be used by a distance image sensor of the indirect ToF system according to the present embodiment and is an explanatory view depicting an example in which the phase of the pixel modulation signal is inverted by 180 degrees at a timing of transition of the state of a pulse based on a bit generated pseudo-randomly (pseudo-random pulse). The pseudo-random pulse is low when the pseudo-randomly generated bit is zero but is high when the pseudo-randomly generated bit is one. In FIG. 54, the phase of the pixel modulation signal transits by 180 degrees at a timing at which the pseudo-random pulse transits from low to high or from high to low. The distance image sensor of the indirect ToF system according to the present embodiment can avoid use of light based on a pulse whose state changes in a different pattern in distance measurement by using the pseudo-random pulse in generation of a modulation signal.

Figure 55:
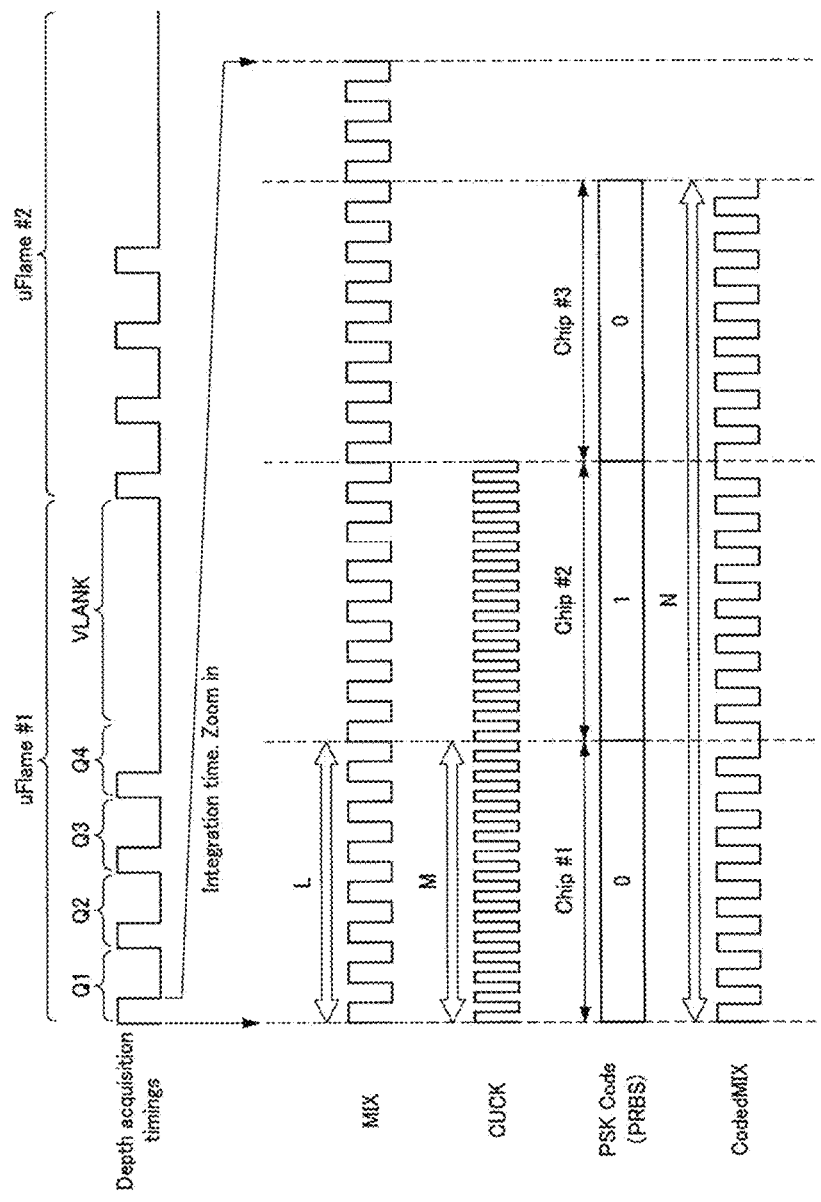
FIG. 55 is an explanatory view illustrating generation of a pseudo random pulse used in the present embodiment.

FIG. 55 is an explanatory view illustrating generation of a pseudo-random pulse used in the present embodiment. FIG. 55 depicts a case in which light reception and reading out are performed four times in one frame. In regard to variables depicted in FIG. 55, N indicates a pseudo-random pattern length, L indicates an encoding cycle length of the modulation signal, and M indicates a cycle in which a pseudo-random pulse is normalized with a logic frequency. The variable N has a bit length of 15 bits, and L can take one of the values of 4, 8, 16 and 32. Further, the variable M has a bit length of 9 bits. For example, if it is assumed that the modulation frequency is 60 MHz, then N=3, L=8 and L=16.

The pseudo-random pulse is generated, for example, in the inside of the sensor chip 11 described hereinabove. For example, the pseudo-random pulse can be generated by the logic circuit 17.

Figure 56:
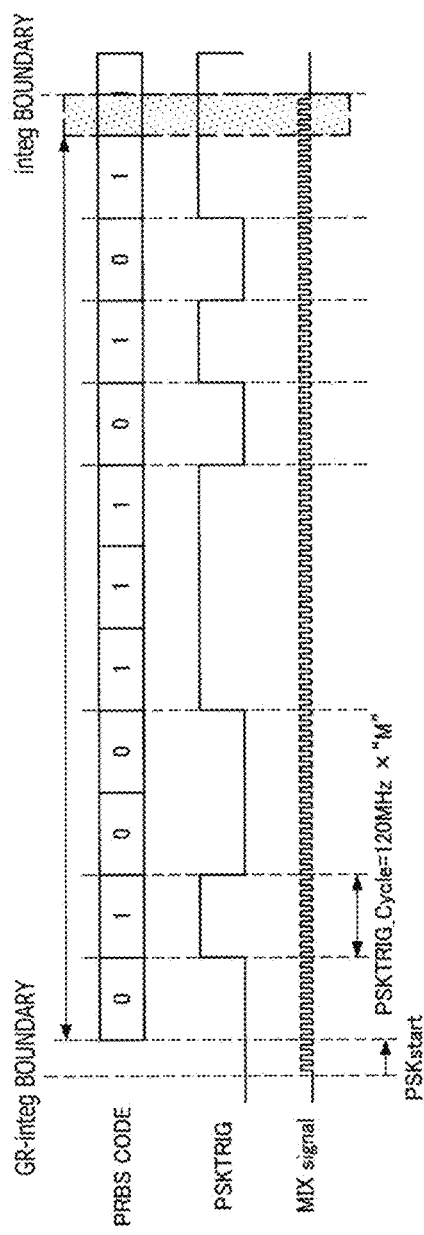
FIG. 56 is an explanatory view depicting an example of signals.

FIG. 56 is an explanatory view depicting an example of a pseudo-random pulse (PSKTRIG) generated on the basis of a bit generated pseudo-randomly and a signal (MIX signal) having a phase inverted by 180 degrees from the pseudo-random pulse by state transition of the pseudo-random pulse. In the example of FIG. 56, during one time reading out, the phase of the modulation signal is changed by state transition of the pseudo-random pulse based on a pseudo-randomly generated bit of 11 bits.

Figure 57:
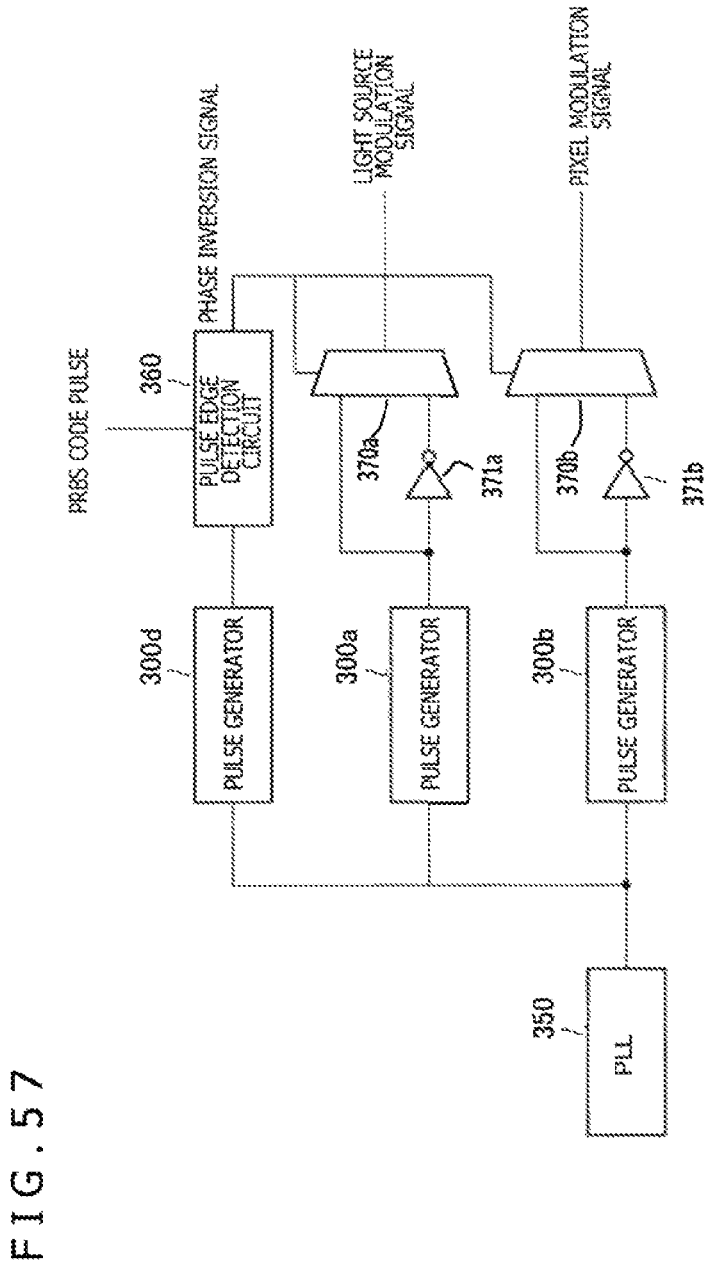
FIG. 57 is an explanatory view depicting a configuration example used in the distance image sensor of the indirect ToF method.

Subsequently, a configuration for inverting the phase of a modulation signal by state transition of the pseudo-random pulse. FIG. 57 is an explanatory view depicting a configuration example used in a distance image sensor of the indirect ToF system according to the embodiment of the present disclosure. In FIG. 57, pulse generators 300*a*, 300*b* and 300*d*, a PLL 350 and a pulse edge detection circuit 360 are depicted. The pulse generator 300*a* is a pulse generator that outputs a light source modulation signal. The pulse generator 300*b* is a pulse generator that outputs a pixel modulation signal. The pulse generator 300*d* is a pulse generator that outputs a reference pulse.

The reference pulse outputted from the pulse generator 300*d* is sent to the pulse edge detection circuit 360. Also a pseudo-random pulse is sent to the pulse edge detection circuit 360. The pulse edge detection circuit 360 detects that state transition of the pseudo-random pulse has occurred by detecting an edge of the pulse. Then, when the pulse edge detection circuit 360 detects that state transition of the pseudo-random pulse has occurred, it outputs a phase inversion signal for inverting the phase of signals to be outputted from the pulse generators 300*a* and 300*b* to selectors 370*a* and 370*b*.

If a phase inversion signal is not sent from the pulse edge detection circuit 360, then the selectors 370*a* and 370*b* output signals outputted from the pulse generators 300*a* and 300*b* as they are. If a phase inversion signal is sent from the pulse edge detection circuit 360, then the selectors 370*a* and 370*b* output signals after the phase of the signals outputted from the pulse generators 300*a* and 300*b* is inverted by inverters 371*a* and 371*b*.

Figure 58:
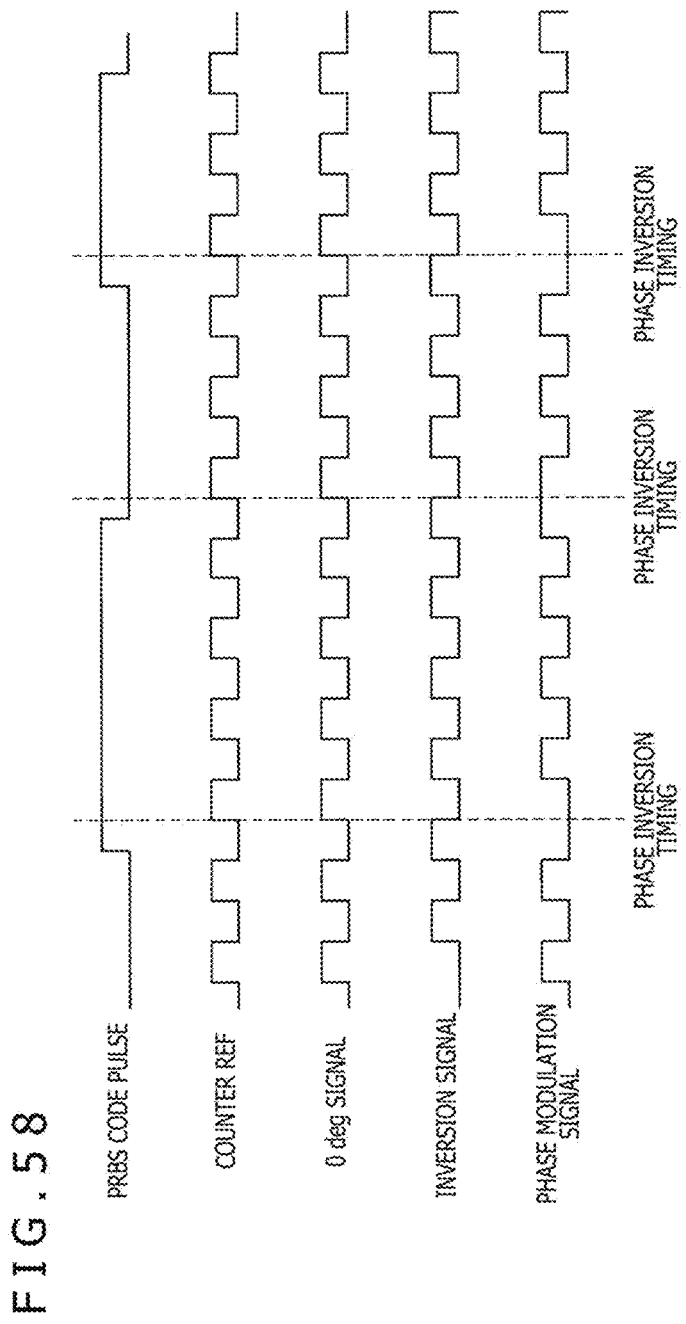
FIG. 58 is an explanatory view depicting an example in which the phase of a modulation signal varies on the basis of a state transition of the pseudo random pulse.

FIG. 58 is an explanatory view depicting an example in which the phase of a modulation signal changes on the basis of state transition of the pseudo-random pulse. In the case where the state of the pseudo-random pulse is low, the modulation signal is a signal (zero deg signal) of a phase same as that of the reference pulse. If the state of the pseudo-random pulse changes to high, then the phase of the modulation signal is inverted at a timing at which the state of the reference pulse immediately after then transits. Thereafter, if the state of the pseudo-random pulse changes to low, then the phase of the modulation signal changes at a timing at which the state of the reference pulse changes immediately after then.

Figure 59:
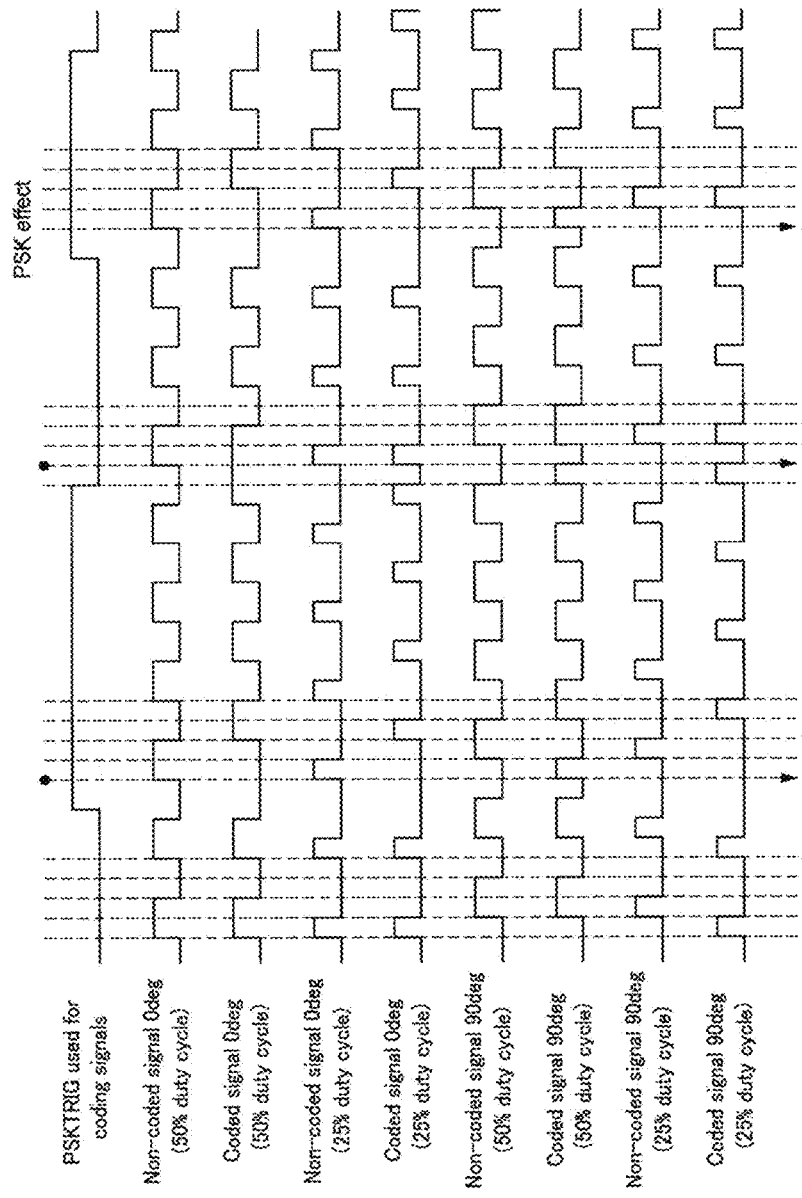
FIG. 59 is an explanatory view depicting an example in which the phase of a modulation signal varies on the basis of a state transition of the pseudo random pulse.

FIG. 59 is an explanatory view depicting an example in which the phase of the modulation signal changes on the basis of state transition of the pseudo-random pulse. The signals depicted in FIG. 59 are, in order from above, a pseudo-random pulse, a non-encrypted signal of zero degrees of a duty of 50%, an encrypted signal of zero degrees of a duty of 50%, a non-encrypted signal of zero degrees of a duty of 25%, an encrypted signal of zero degrees of a duty of 25%, non-encrypted signal of 90 degrees of a duty of 50%, an encrypted signal of 90 degrees of a duty of 50%, a non-encrypted signal of 90 degrees of a duty of 25%, and an encrypted signal of 90 degrees of a duty of 25%.

As described hereinabove, the distance image sensor of the indirect ToF system according to the embodiment of the present disclosure can change the duty of a pulse to be generated by the pulse generator 300. Especially, by setting the duty of the light source outputting signal smaller than 50%, the cyclic error can be reduced. Accordingly, in the FIG. 59, by using the signal of a 50% duty as a pixel modulation signal and using a signal of a 25% duty as a light source outputting signal, while the distance image sensor of the indirect ToF system according to the embodiment of the present disclosure reduces the cyclic error, it can decide light to be used for distance measurement even in the case where the image sensor receives light from a plurality of light sources.

The distance image sensor of the indirect ToF system according to the embodiment of the present disclosure synchronizes the timings at which the phases of the pixel modulation signal and light source outputting signal are shifted with each other as depicted in FIG. 59. By synchronizing the timings at which the phases of the pixel modulation signal and the light source outputting signal are shifted with each other, it can decide light to be used for distance measurement even in the case where the image sensor receives light from a plurality of light sources.

Figure 60:
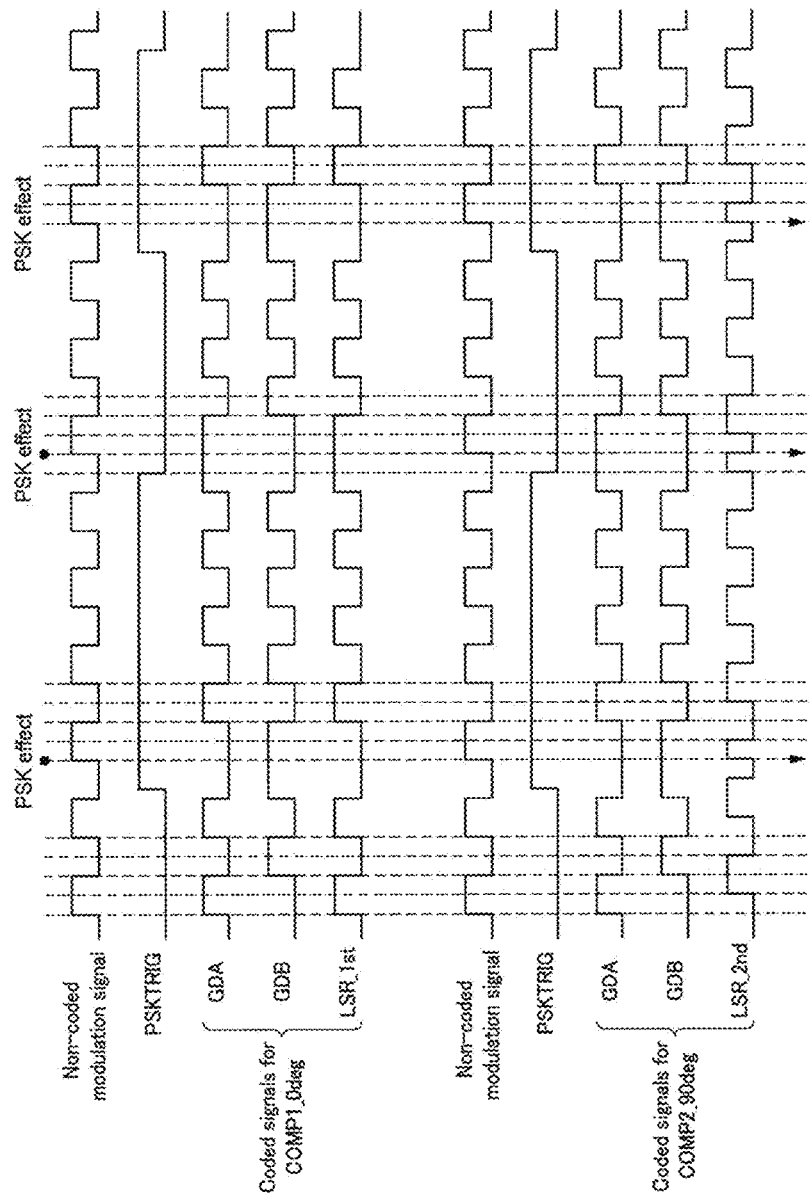
FIG. 60 is an explanatory view depicting an example in which the phase of a modulation signal varies on the basis of a state transition of the pseudo random pulse.

FIG. 60 is an explanatory view depicting an example in which the phase of the modulation signal changes based on state transition of the pseudo-random pulse. The signals depicted in FIG. 60 are, in order from above, a non-encrypted modulation signal, a pseudo-random pulse, a pixel modulation signal A, a pixel modulation signal B, a light source outputting signal of a phase same as that of the non-encrypted modulation signal, a non-encrypted modulation signal, a pseudo-random pulse, a pixel modulation signal A, a pixel modulation signal B and a light source outputting signal having a phase displaced by 90 degrees from that of the non-encrypted modulation signal. The duty of the light source outputting signal depicted in FIG. 60 is 50%.

Figure 61:
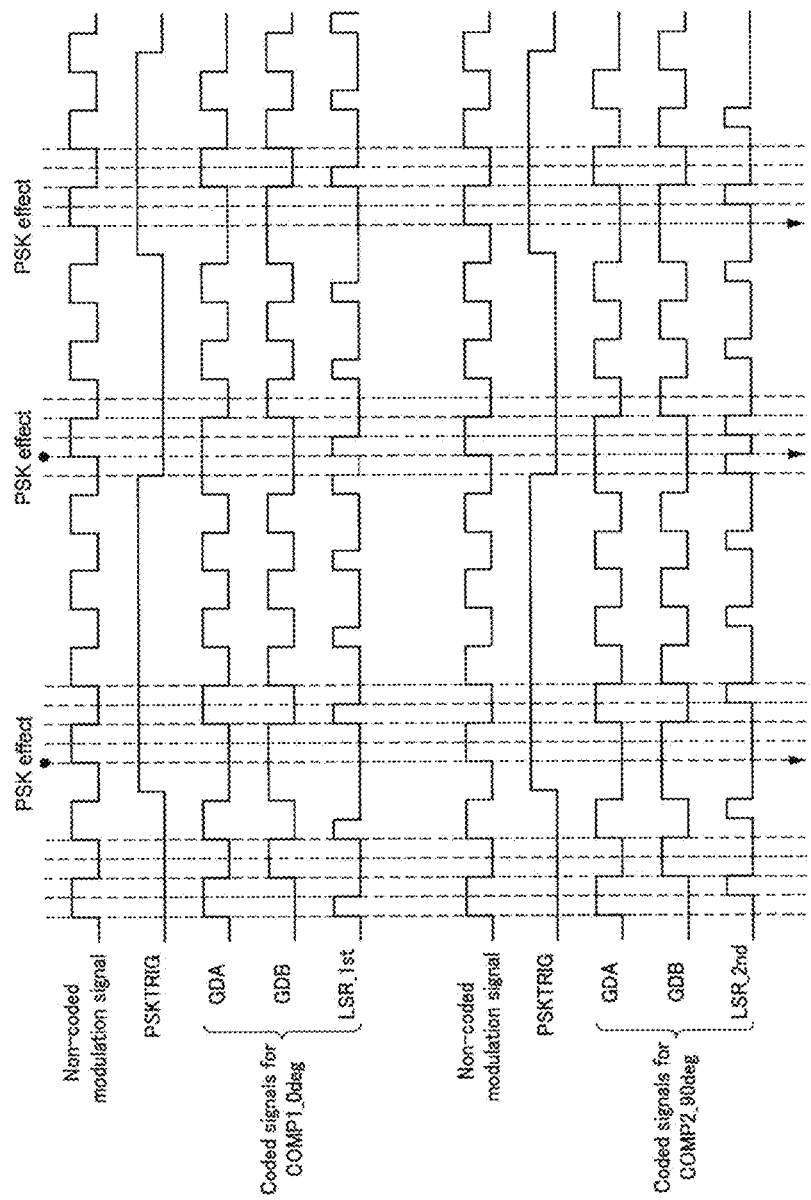
FIG. 61 is an explanatory view depicting an example in which the phase of a modulation signal varies on the basis of a state transition of the pseudo random pulse.

FIG. 61 is an explanatory view depicting another example in which the phase of the modulation signal changes based on state transition of the pseudo-random pulse. The signals depicted in FIG. 61 are, in order from above, a non-encrypted modulation signal, a pseudo-random pulse, a pixel modulation signal A, a pixel modulation signal B, a light source outputting signal of a phase same as that of the non-encrypted modulation signal, a non-encrypted modulation signal, a pseudo-random pulse, a pixel modulation signal A, a pixel modulation signal B and a light source outputting signal having a phase displaced by 90 degrees from that of the non-encrypted modulation signal. The duty of the light source outputting signal depicted in FIG. 61 is 50%.

Figure 62:
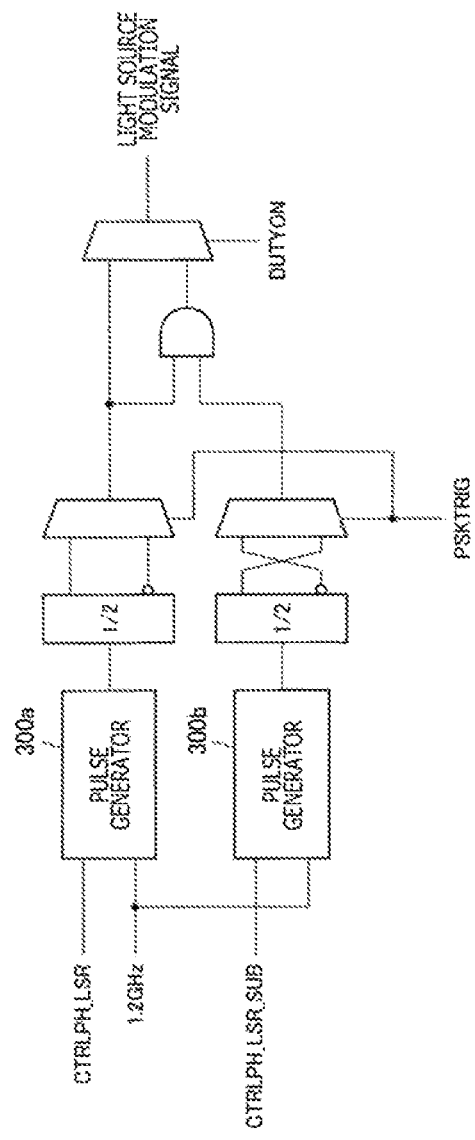
FIG. 62 is an explanatory view depicting an example of a configuration that selects and outputs two signals having different duties from each other from two pulse generators.

FIG. 62 is an explanatory view depicting an example of a configuration that selects and outputs two kinds of signals having different duty ratios from each other from the two pulse generators 300$a$ and 300$b$. As described hereinabove, by making the phases of signals of the pulse generators 300$a$ and 300$b$ different from each other, a signal having a duty smaller than 50% can be generated. Thereupon, one of a signal whose duty is 50% and a signal whose duty is smaller than 50% is outputted as a light source outputting signal depending upon the state of a signal DUTYON.

Figure 63:
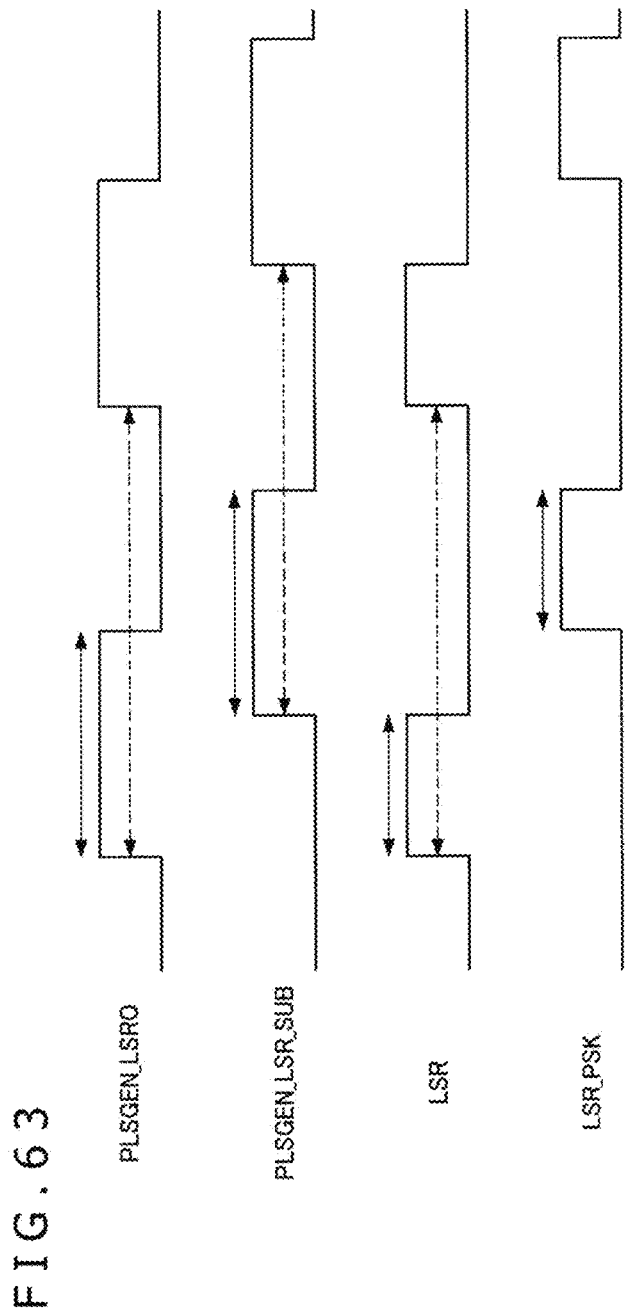
FIG. 63 is an explanatory view depicting an example of a waveform of a signal having a duty smaller than 50% and a waveform of a signal generated on the basis of a pseudo random pulse, which are generated from a pulse generator.

FIG. 63 depicts an example of a waveform of a signal LSR having a duty smaller than 50% and a signal LSR_PSK having a phase inverted from that of the signal LSR on the basis of the pseudo-random pulse, both generated from the pulse generators 300$a$ and 300$b$. In the present embodiment, any one of the signal LSR and the signal LSR_PSK is selected as a signal having a duty smaller than 50% on the basis of a trigger signal PSKTRIG based on the pseudo-random pulse.

The distance image sensor of the indirect ToF system according to the embodiment of the present disclosure generates a pseudo-random pulse in this manner and changes the phase of a light source outputting signal and a pixel modulation signal on the basis of the pseudo-random pulse. In other words, the phase can be inverted. By changing the phase of the light source outputting signal and the pixel modulation signal on the basis of the pseudo-random pulse, the distance image sensor of the indirect ToF system according to the embodiment of the present disclosure can decide whether or not light received by the image sensor is received light emitted from a light source of the distance image sensor itself even in the case where a different distance image sensor that simultaneously measures the distance to a same target exists.

<Application Example to Endoscopic Surgery System>

The technology according to the present disclosure (present technology) can be applied to various products. For example, the technology according to the present disclosure may be applied to an endoscopic surgery system.

Figure 64:
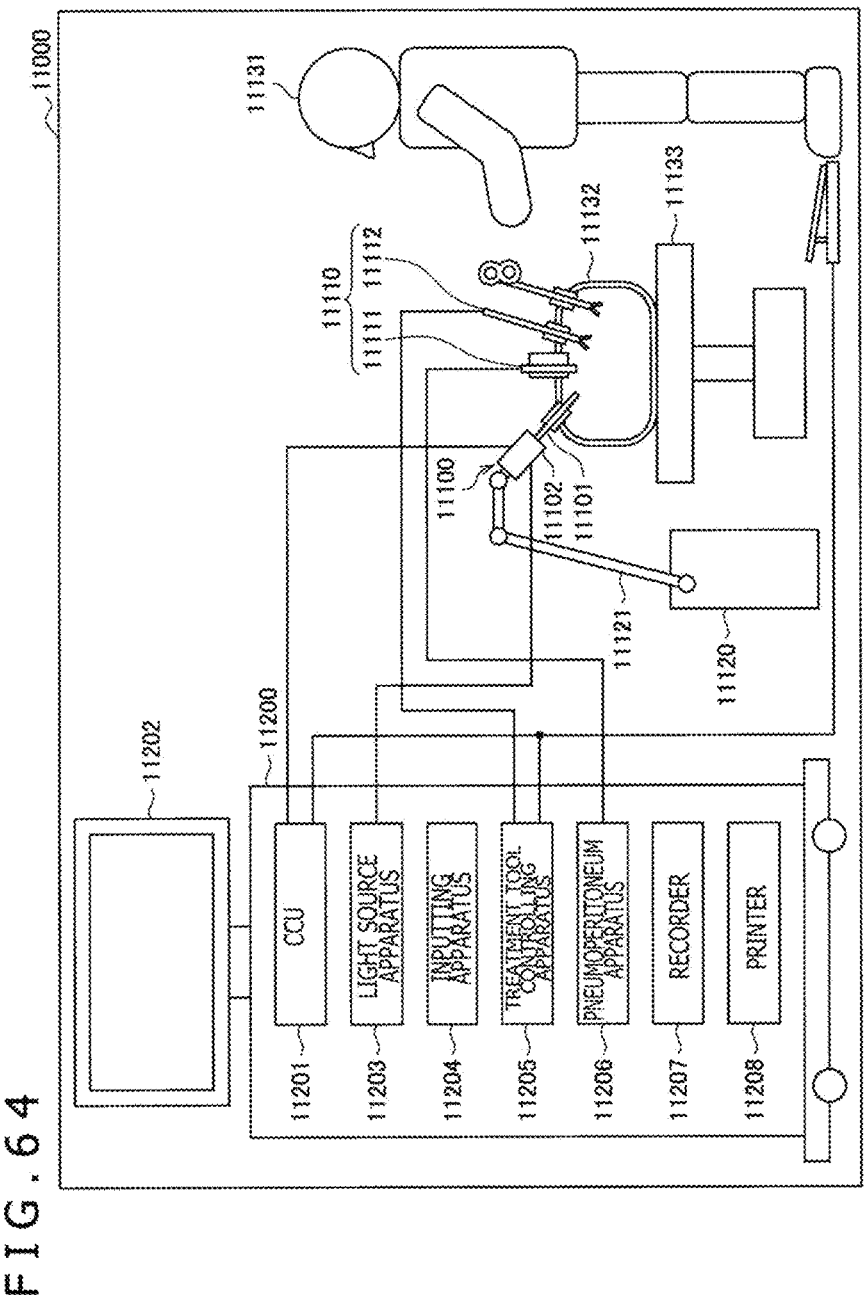
FIG. 64 is a view depicting an example of a schematic configuration of an endoscopic surgery system.

FIG. 64 is a view depicting an example of a schematic configuration of an endoscopic surgery system to which the technology according to an embodiment of the present disclosure (present technology) can be applied.

In FIG. 64, a state is illustrated in which a surgeon (medical doctor) 11131 is using an endoscopic surgery system 11000 to perform surgery for a patient 11132 on a patient bed 11133. As depicted, the endoscopic surgery system 11000 includes an endoscope 11100, other surgical tools 11110 such as a pneumoperitoneum tube 11111 and an energy device 11112, a supporting arm apparatus 11120 which supports the endoscope 11100 thereon, and a cart 11200 on which various apparatus for endoscopic surgery are mounted.

The endoscope 11100 includes a lens barrel 11101 having a region of a predetermined length from a distal end thereof to be inserted into a body cavity of the patient 11132, and a camera head 11102 connected to a proximal end of the lens barrel 11101. In the example depicted, the endoscope 11100 is depicted which includes as a rigid endoscope having the lens barrel 11101 of the hard type. However, the endoscope 11100 may otherwise be included as a flexible endoscope having the lens barrel 11101 of the flexible type.

The lens barrel 11101 has, at a distal end thereof, an opening in which an objective lens is fitted. A light source apparatus 11203 is connected to the endoscope 11100 such that light generated by the light source apparatus 11203 is introduced to a distal end of the lens barrel 11101 by a light guide extending in the inside of the lens barrel 11101 and is irradiated toward an observation target in a body cavity of the patient 11132 through the objective lens. It is to be noted that the endoscope 11100 may be a forward-viewing endoscope or may be an oblique-viewing endoscope or a side-viewing endoscope.

An optical system and an image pickup element are provided in the inside of the camera head 11102 such that reflected light (observation light) from the observation target is condensed on the image pickup element by the optical system. The observation light is photo-electrically converted by the image pickup element to generate an electric signal corresponding to the observation light, namely, an image signal corresponding to an observation image. The image signal is transmitted as RAW data to a CCU 11201.

The CCU 11201 includes a central processing unit (CPU), a graphics processing unit (GPU) or the like and integrally controls operation of the endoscope 11100 and a display apparatus 11202. Further, the CCU 11201 receives an image signal from the camera head 11102 and performs, for the image signal, various image processes for displaying an image based on the image signal such as, for example, a development process (demosaic process).

The display apparatus 11202 displays thereon an image based on an image signal, for which the image processes have been performed by the CCU 11201, under the control of the CCU 11201.

The light source apparatus 11203 includes a light source such as, for example, a LED (Light Emitting Diode) and supplies irradiation light upon imaging of a surgical region to the endoscope 11100.

An inputting apparatus 11204 is an input interface for the endoscopic surgery system 11000. A user can perform inputting of various kinds of information or instruction inputting to the endoscopic surgery system 11000 through the inputting apparatus 11204. For example, the user would input an instruction or a like to change an image pickup condition (type of irradiation light, magnification, focal distance or the like) by the endoscope 11100.

A treatment tool controlling apparatus 11205 controls driving of the energy device 11112 for cautery or incision of a tissue, sealing of a blood vessel or the like. A pneumoperitoneum apparatus 11206 feeds gas into a body cavity of the patient 11132 through the pneumoperitoneum tube 11111 to inflate the body cavity in order to secure the field of view of the endoscope 11100 and secure the working space for the surgeon. A recorder 11207 is an apparatus capable of recording various kinds of information relating to surgery. A printer 11208 is an apparatus capable of printing various kinds of information relating to surgery in various forms such as a text, an image or a graph.

It is to be noted that the light source apparatus 11203 which supplies irradiation light when a surgical region is to be imaged to the endoscope 11100 may include a white light source which includes, for example, an LED, a laser light source or a combination of them. Where a white light source includes a combination of red, green, and blue (RGB) laser light sources, since the output intensity and the output timing can be controlled with a high degree of accuracy for each color (each wavelength), adjustment of the white balance of a picked up image can be performed by the light source apparatus 11203. Further, in this case, if laser beams from the respective RGB laser light sources are irradiated time-divisionally on an observation target and driving of the image pickup elements of the camera head 11102 are controlled in synchronism with the irradiation timings. Then images individually corresponding to the R, G and B colors can be also picked up time-divisionally. According to this method, a color image can be obtained even if color filters are not provided for the image pickup element.

Further, the light source apparatus 11203 may be controlled such that the intensity of light to be outputted is changed for each predetermined time. By controlling driving of the image pickup element of the camera head 11102 in synchronism with the timing of the change of the intensity of light to acquire images time-divisionally and synthesizing the images, an image of a high dynamic range free from underexposed blocked up shadows and overexposed highlights can be created.

Further, the light source apparatus 11203 may be configured to supply light of a predetermined wavelength band ready for special light observation. In special light observation, for example, by utilizing the wavelength dependency of absorption of light in a body tissue to irradiate light of a narrow band in comparison with irradiation light upon ordinary observation (namely, white light), narrow band observation (narrow band imaging) of imaging a predetermined tissue such as a blood vessel of a superficial portion of the mucous membrane or the like in a high contrast is performed. Alternatively, in special light observation, fluorescent observation for obtaining an image from fluorescent light generated by irradiation of excitation light may be performed. In fluorescent observation, it is possible to perform observation of fluorescent light from a body tissue by irradiating excitation light on the body tissue (autofluorescence observation) or to obtain a fluorescent light image by locally injecting a reagent such as indocyanine green (ICG) into a body tissue and irradiating excitation light corresponding to a fluorescent light wavelength of the reagent upon the body tissue. The light source apparatus 11203 can be configured to supply such narrow-band light and/or excitation light suitable for special light observation as described above.

Figure 65:
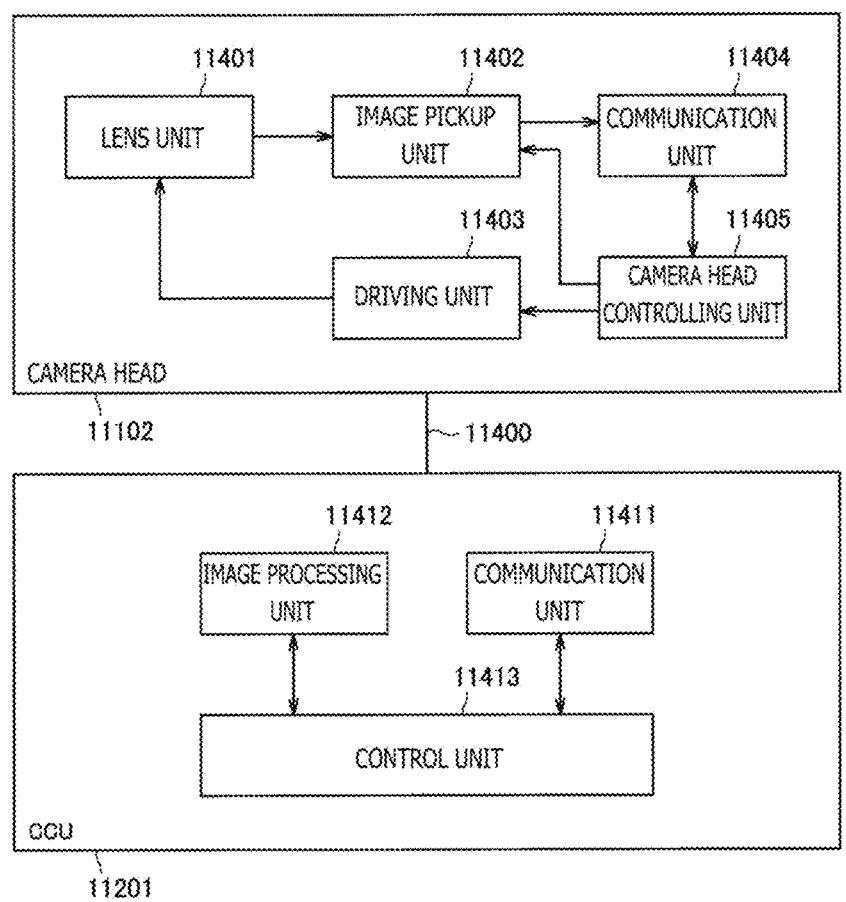
FIG. 65 is a block diagram depicting an example of a functional configuration of a camera head and a CCU.

FIG. 65 is a block diagram depicting an example of a functional configuration of the camera head 11102 and the CCU 11201 depicted in FIG. 64.

The camera head 11102 includes a lens unit 11401, an image pickup unit 11402, a driving unit 11403, a communication unit 11404 and a camera head controlling unit 11405. The CCU 11201 includes a communication unit 11411, an image processing unit 11412 and a control unit 11413. The camera head 11102 and the CCU 11201 are connected for communication to each other by a transmission cable 11400.

The lens unit 11401 is an optical system, provided at a connecting location to the lens barrel 11101. Observation light taken in from a distal end of the lens barrel 11101 is guided to the camera head 11102 and introduced into the lens unit 11401. The lens unit 11401 includes a combination of a plurality of lenses including a zoom lens and a focusing lens.

An image pickup unit 11402 includes the image pickup element. The number of image pickup elements which is included by the image pickup unit 11402 may be one (single-plate type) or a plural number (multi-plate type). Where the image pickup unit 11402 is configured as that of the multi-plate type, for example, image signals corresponding to respective R, G and B are generated by the image pickup elements, and the image signals may be synthesized to obtain a color image. The image pickup unit 11402 may also be configured so as to have a pair of image pickup elements for acquiring respective image signals for the right eye and the left eye ready for three dimensional (3D) display. If 3D display is performed, then the depth of a living body tissue in a surgical region can be comprehended more accurately by the surgeon 11131. It is to be noted that, where the image pickup unit 11402 is configured as that of stereoscopic type, a plurality of systems of lens units 11401 are provided corresponding to the individual image pickup elements.

Further, the image pickup unit 11402 may not necessarily be provided on the camera head 11102. For example, the image pickup unit 11402 may be provided immediately behind the objective lens in the inside of the lens barrel 11101.

The driving unit 11403 includes an actuator and moves the zoom lens and the focusing lens of the lens unit 11401 by a predetermined distance along an optical axis under the control of the camera head controlling unit 11405. Consequently, the magnification and the focal point of a picked up image by the image pickup unit 11402 can be adjusted suitably.

The communication unit 11404 includes a communication apparatus for transmitting and receiving various kinds of information to and from the CCU 11201. The communication unit 11404 transmits an image signal acquired from the image pickup unit 11402 as RAW data to the CCU 11201 through the transmission cable 11400.

In addition, the communication unit 11404 receives a control signal for controlling driving of the camera head 11102 from the CCU 11201 and supplies the control signal to the camera head controlling unit 11405. The control signal includes information relating to image pickup conditions such as, for example, information that a frame rate of a picked up image is designated, information that an exposure value upon image picking up is designated and/or information that a magnification and a focal point of a picked up image are designated.

It is to be noted that the image pickup conditions such as the frame rate, exposure value, magnification or focal point may be designated by the user or may be set automatically by the control unit 11413 of the CCU 11201 on the basis of an acquired image signal. In the latter case, an auto exposure (AE) function, an auto focus (AF) function and an auto white balance (AWB) function are incorporated in the endoscope 11100.

The camera head controlling unit 11405 controls driving of the camera head 11102 on the basis of a control signal from the CCU 11201 received through the communication unit 11404.

The communication unit 11411 includes a communication apparatus for transmitting and receiving various kinds of information to and from the camera head 11102. The communication unit 11411 receives an image signal transmitted thereto from the camera head 11102 through the transmission cable 11400.

Further, the communication unit 11411 transmits a control signal for controlling driving of the camera head 11102 to the camera head 11102. The image signal and the control signal can be transmitted by electrical communication, optical communication or the like.

The image processing unit 11412 performs various image processes for an image signal in the form of RAW data transmitted thereto from the camera head 11102.

The control unit 11413 performs various kinds of control relating to image picking up of a surgical region or the like by the endoscope 11100 and display of a picked up image obtained by image picking up of the surgical region or the like. For example, the control unit 11413 creates a control signal for controlling driving of the camera head 11102.

Further, the control unit 11413 controls, on the basis of an image signal for which image processes have been performed by the image processing unit 11412, the display apparatus 11202 to display a picked up image in which the surgical region or the like is imaged. Thereupon, the control unit 11413 may recognize various objects in the picked up image using various image recognition technologies. For example, the control unit 11413 can recognize a surgical tool such as forceps, a particular living body region, bleeding, mist when the energy device 11112 is used and so forth by detecting the shape, color and so forth of edges of objects included in a picked up image. The control unit 11413 may cause, when it controls the display apparatus 11202 to display a picked up image, various kinds of surgery supporting information to be displayed in an overlapping manner with an image of the surgical region using a result of the recognition. Where surgery supporting information is displayed in an overlapping manner and presented to the surgeon 11131, the burden on the surgeon 11131 can be reduced and the surgeon 11131 can proceed with the surgery with certainty.

The transmission cable 11400 which connects the camera head 11102 and the CCU 11201 to each other is an electric signal cable ready for communication of an electric signal, an optical fiber ready for optical communication or a composite cable ready for both of electrical and optical communications.

Here, while, in the example depicted, communication is performed by wired communication using the transmission cable 11400, the communication between the camera head 11102 and the CCU 11201 may be performed by wireless communication.

An example of an endoscopic surgery system to which the technology according to the present disclosure can be applied has been described. The technology according to the present disclosure can be applied, from within the configuration described above, for example, to the endoscope 11100, (the image pickup unit 11402 of) the camera head 11102, (the image processing unit 11412 of) the CCU 11201 and so forth.

It is to be noted here that, while an endoscopic surgery system has been described as an example, the technology according to the present disclosure may be applied, for example, to a microscopic surgery system or the like.

<Application Example of Moving Body>

The technology according to the present disclosure (present technology) can be applied to various products. For example, the technology according to the present disclosure may be implemented as an apparatus that is incorporated in any type of moving body such as an automobile, an electric car, a hybrid electric car, a motorcycle, a bicycle, a personal mobility, an airplane, a drone, a ship, a robot and so forth.

Figure 66:
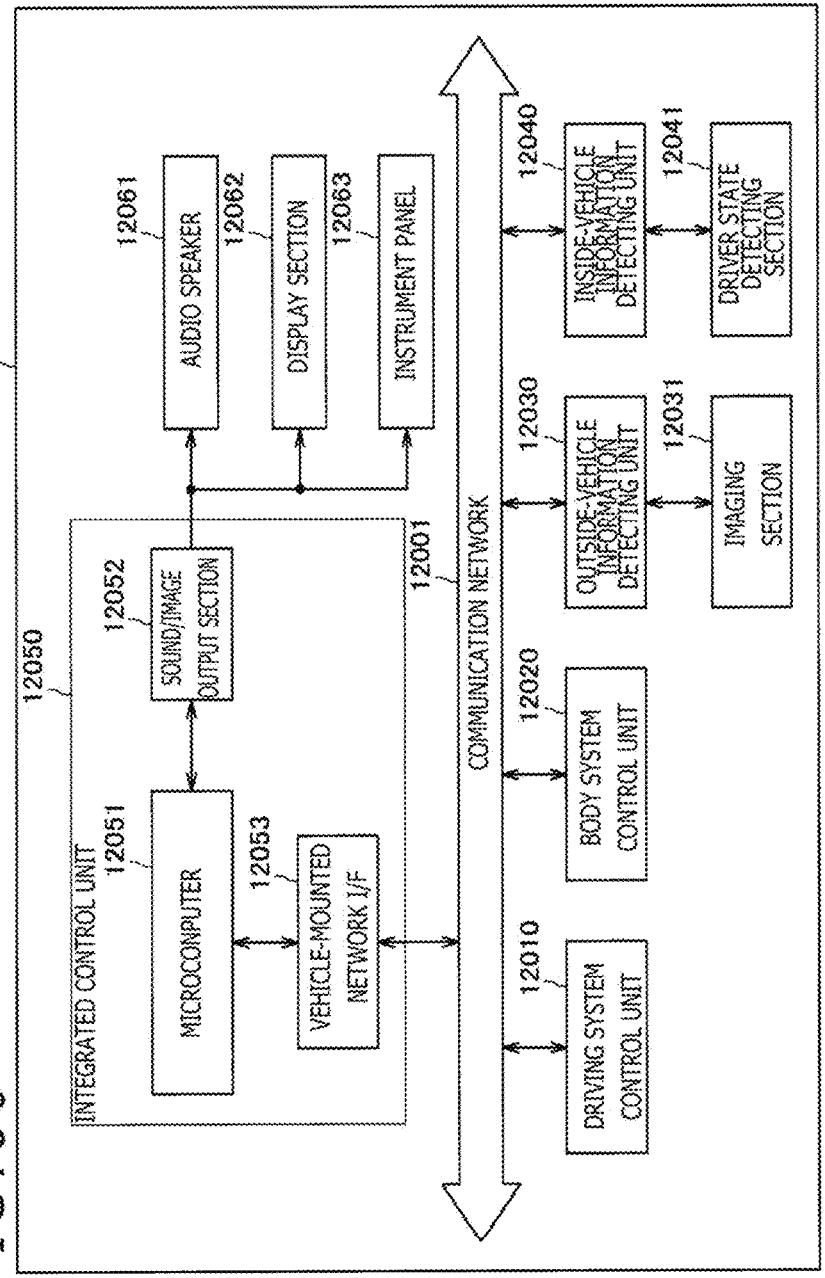
FIG. 66 is a block diagram depicting an example of schematic configuration of a vehicle control system.

FIG. 66 is a block diagram depicting an example of schematic configuration of a vehicle control system as an example of a mobile body control system to which the technology according to an embodiment of the present disclosure can be applied.

The vehicle control system 12000 includes a plurality of electronic control units connected to each other via a communication network 12001. In the example depicted in FIG. 66, the vehicle control system 12000 includes a driving system control unit 12010, a body system control unit 12020, an outside-vehicle information detecting unit 12030, an in-vehicle information detecting unit 12040, and an integrated control unit 12050. In addition, a microcomputer 12051, a sound/image output section 12052, and a vehicle-mounted network interface (I/F) 12053 are illustrated as a functional configuration of the integrated control unit 12050.

The driving system control unit 12010 controls the operation of devices related to the driving system of the vehicle in accordance with various kinds of programs. For example, the driving system control unit 12010 functions as a control device for a driving force generating device for generating the driving force of the vehicle, such as an internal combustion engine, a driving motor, or the like, a driving force transmitting mechanism for transmitting the driving force to wheels, a steering mechanism for adjusting the steering angle of the vehicle, a braking device for generating the braking force of the vehicle, and the like.

The body system control unit 12020 controls the operation of various kinds of devices provided to a vehicle body in accordance with various kinds of programs. For example, the body system control unit 12020 functions as a control device for a keyless entry system, a smart key system, a power window device, or various kinds of lamps such as a headlamp, a backup lamp, a brake lamp, a turn signal, a fog lamp, or the like. In this case, radio waves transmitted from a mobile device as an alternative to a key or signals of various kinds of switches can be input to the body system control unit 12020. The body system control unit 12020 receives these input radio waves or signals, and controls a door lock device, the power window device, the lamps, or the like of the vehicle.

The outside-vehicle information detecting unit 12030 detects information about the outside of the vehicle including the vehicle control system 12000. For example, the outside-vehicle information detecting unit 12030 is connected with an imaging section 12031. The outside-vehicle information detecting unit 12030 makes the imaging section 12031 image an image of the outside of the vehicle, and receives the imaged image. On the basis of the received image, the outside-vehicle information detecting unit 12030 may perform processing of detecting an object such as a human, a vehicle, an obstacle, a sign, a character on a road surface, or the like, or processing of detecting a distance thereto.

The imaging section 12031 is an optical sensor that receives light, and which outputs an electric signal corresponding to a received light amount of the light. The imaging section 12031 can output the electric signal as an image, or can output the electric signal as information about a measured distance. In addition, the light received by the imaging section 12031 may be visible light, or may be invisible light such as infrared rays or the like.

The in-vehicle information detecting unit 12040 detects information about the inside of the vehicle. The in-vehicle information detecting unit 12040 is, for example, connected with a driver state detecting section 12041 that detects the state of a driver. The driver state detecting section 12041, for example, includes a camera that images the driver. On the basis of detection information input from the driver state detecting section 12041, the in-vehicle information detecting unit 12040 may calculate a degree of fatigue of the driver or a degree of concentration of the driver, or may determine whether the driver is dozing.

The microcomputer 12051 can calculate a control target value for the driving force generating device, the steering mechanism, or the braking device on the basis of the information about the inside or outside of the vehicle which information is obtained by the outside-vehicle information detecting unit 12030 or the in-vehicle information detecting unit 12040, and output a control command to the driving system control unit 12010. For example, the microcomputer 12051 can perform cooperative control intended to implement functions of an advanced driver assistance system (ADAS) which functions include collision avoidance or shock mitigation for the vehicle, following driving based on a following distance, vehicle speed maintaining driving, a warning of collision of the vehicle, a warning of deviation of the vehicle from a lane, or the like.

In addition, the microcomputer 12051 can perform cooperative control intended for automatic driving, which makes the vehicle to travel autonomously without depending on the operation of the driver, or the like, by controlling the driving force generating device, the steering mechanism, the braking device, or the like on the basis of the information about the outside or inside of the vehicle which information is obtained by the outside-vehicle information detecting unit 12030 or the in-vehicle information detecting unit 12040.

In addition, the microcomputer 12051 can output a control command to the body system control unit 12020 on the basis of the information about the outside of the vehicle which information is obtained by the outside-vehicle information detecting unit 12030. For example, the microcomputer 12051 can perform cooperative control intended to prevent a glare by controlling the headlamp so as to change from a high beam to a low beam, for example, in accordance with the position of a preceding vehicle or an oncoming vehicle detected by the outside-vehicle information detecting unit 12030.

The sound/image output section 12052 transmits an output signal of at least one of a sound and an image to an output device capable of visually or auditorily notifying information to an occupant of the vehicle or the outside of the vehicle. In the example of FIG. 66, an audio speaker 12061, a display section 12062, and an instrument panel 12063 are illustrated as the output device. The display section 12062 may, for example, include at least one of an on-board display and a head-up display.

Figure 67:
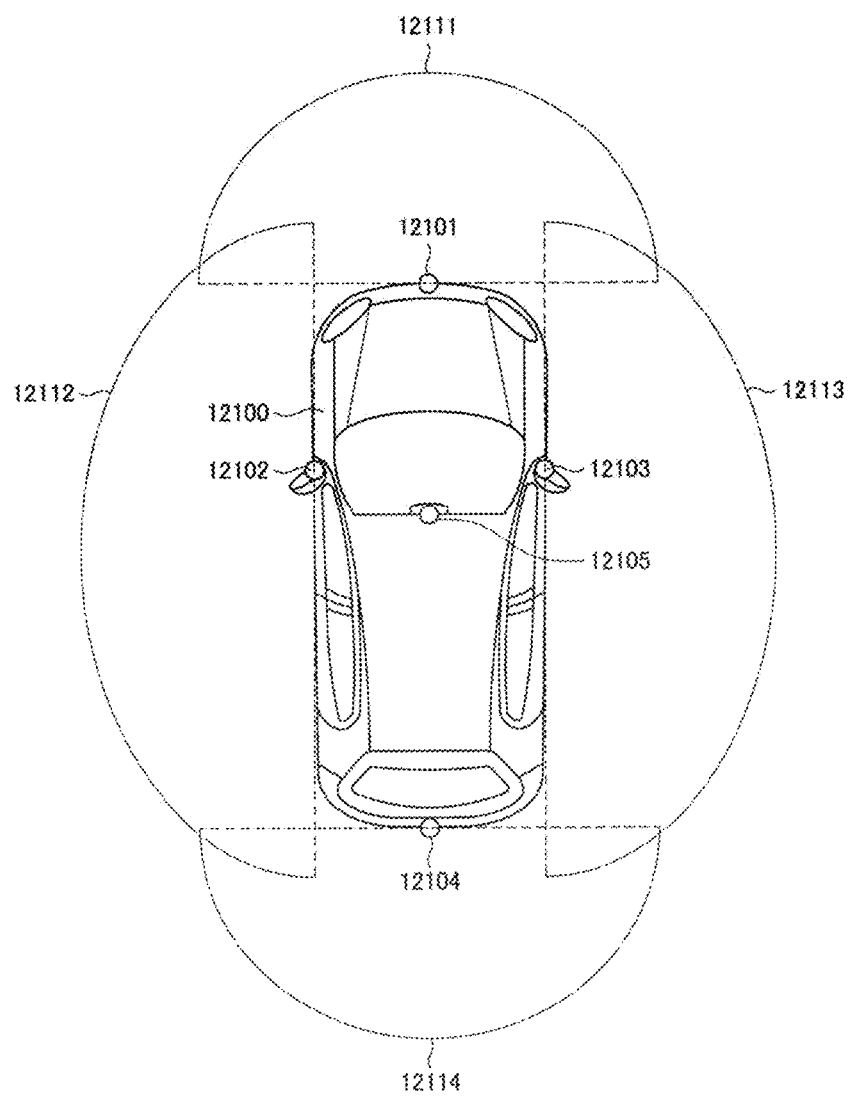
FIG. 67 is a diagram of assistance in explaining an example of installation positions of an outside-vehicle information detecting section and an imaging section.

FIG. 67 is a diagram depicting an example of the installation position of the imaging section 12031.

In FIG. 67, on the vehicle 12100, the imaging section 12031 includes imaging sections 12101, 12102, 12103, 12104, and 12105.

The imaging sections 12101, 12102, 12103, 12104, and 12105 are, for example, disposed at positions on a front nose, sideview mirrors, a rear bumper, and a back door of the vehicle 12100 as well as a position on an upper portion of a windshield within the interior of the vehicle. The imaging section 12101 provided to the front nose and the imaging section 12105 provided to the upper portion of the windshield within the interior of the vehicle obtain mainly an image of the front of the vehicle 12100. The imaging sections 12102 and 12103 provided to the sideview mirrors obtain mainly an image of the sides of the vehicle 12100. The image of the front of the vehicle 12100. The imaging sections 12101 and 12105 provided to the rear bumper or the back door obtains mainly an image of the rear of the vehicle 12100. The image of the front obtained by the imaging sections 12101 and 12105 is used mainly to detect a preceding vehicle, a pedestrian, an obstacle, a signal, a traffic sign, a lane, or the like.

Incidentally, FIG. 67 depicts an example of photographing ranges of the imaging sections 12101 to 12104. An imaging range 12111 represents the imaging range of the imaging section 12101 provided to the front nose. Imaging ranges 12112 and 12113 respectively represent the imaging ranges of the imaging sections 12102 and 12103 provided to the sideview mirrors. An imaging range 12114 represents the imaging range of the imaging section 12104 provided to the rear bumper or the back door. A bird's-eye image of the vehicle 12100 as viewed from above is obtained by superimposing image data imaged by the imaging sections 12101 to 12104, for example.

At least one of the imaging sections 12101 to 12104 may have a function of obtaining distance information. For example, at least one of the imaging sections 12101 to 12104 may be a stereo camera constituted of a plurality of imaging elements, or may be an imaging element having pixels for phase difference detection.

For example, the microcomputer 12051 can determine a distance to each three-dimensional object within the imaging ranges 12111 to 12114 and a temporal change in the distance (relative speed with respect to the vehicle 12100) on the basis of the distance information obtained from the imaging sections 12101 to 12104, and thereby extract, as a preceding vehicle, a nearest three-dimensional object in particular that is present on a traveling path of the vehicle 12100 and which travels in substantially the same direction as the vehicle 12100 at a predetermined speed (for example, equal to or more than 0 km/hour). Further, the microcomputer 12051 can set a following distance to be maintained in front of a preceding vehicle in advance, and perform automatic brake control (including following stop control), automatic acceleration control (including following start control), or the like. It is thus possible to perform cooperative control intended for automatic driving that makes the vehicle travel autonomously without depending on the operation of the driver or the like.

For example, the microcomputer 12051 can classify three-dimensional object data on three-dimensional objects into three-dimensional object data of a two-wheeled vehicle, a standard-sized vehicle, a large-sized vehicle, a pedestrian, a utility pole, and other three-dimensional objects on the basis of the distance information obtained from the imaging sections 12101 to 12104, extract the classified three-dimensional object data, and use the extracted three-dimensional object data for automatic avoidance of an obstacle. For example, the microcomputer 12051 identifies obstacles around the vehicle 12100 as obstacles that the driver of the vehicle 12100 can recognize visually and obstacles that are difficult for the driver of the vehicle 12100 to recognize visually. Then, the microcomputer 12051 determines a collision risk indicating a risk of collision with each obstacle. In a situation in which the collision risk is equal to or higher than a set value and there is thus a possibility of collision, the microcomputer 12051 outputs a warning to the driver via the audio speaker 12061 or the display section 12062, and performs forced deceleration or avoidance steering via the driving system control unit 12010. The microcomputer 12051 can thereby assist in driving to avoid collision.

At least one of the imaging sections 12101 to 12104 may be an infrared camera that detects infrared rays. The microcomputer 12051 can, for example, recognize a pedestrian by determining whether or not there is a pedestrian in imaged images of the imaging sections 12101 to 12104. Such recognition of a pedestrian is, for example, performed by a procedure of extracting characteristic points in the imaged images of the imaging sections 12101 to 12104 as infrared cameras and a procedure of determining whether or not it is the pedestrian by performing pattern matching processing on a series of characteristic points representing the contour of the object. When the microcomputer 12051 determines that there is a pedestrian in the imaged images of the imaging sections 12101 to 12104, and thus recognizes the pedestrian, the sound/image output section 12052 controls the display section 12062 so that a square contour line for emphasis is displayed so as to be superimposed on the recognized pedestrian. The sound/image output section 12052 may also control the display section 12062 so that an icon or the like representing the pedestrian is displayed at a desired position.

An example of a vehicle control system to which the technology according to the present disclosure can be applied has been described. The technology according to the present disclosure can be applied to the imaging section 12031 or the like in the configuration described above.

<2. Summary>

As described above, according to the embodiment of the present disclosure, there is provided a configuration that is used in a camera system that adopts the indirect ToF system and can suppress occurrence of the cyclic error with a simple configuration.

Although the preferred embodiments of the present disclosure have been described in detail with reference to the accompanying drawings, the technical scope of the present disclosure is not limited to such embodiments as described above. It is apparent that those who have common knowledge in the technical field of the present disclosure can conceive various alternations or modifications without departing from the technical scope described in the claims, and it is recognized that also they naturally belong to the technical scope of the present disclosure.

Further, the advantageous effects described in the present specification are explanatory and exemplary to the last and are not restrictive. In other words, the technology according to the present disclosure can play, together with or in places of the advantageous effects described above, other advantageous effects that are apparent to those skilled in the art from the description of the present specification.

It is to be noted that also such configurations as described below belong to the technical scope of the present disclosure.

(1)

A signal generation apparatus including:

a first pulse generator configured to generate a pulse to be supplied to a light source that irradiates light upon a distance measurement target;

a second pulse generator configured to generate a pulse to be supplied to a pixel that receives the light reflected by the distance measurement target; and a signal generation section configured to generate a pseudo-random signal for inverting a phase of signals to be generated by the first pulse generator and the second pulse generator.

(2)

The signal generation apparatus according to (1) above, further including:

a detection section configured to detect a transition of a state of the pseudo-random signal, in which when the detection section detects a transition of a state of the pseudo-random signal, the detection section outputs a signal for inverting the phase of the signals to be generated by the first pulse generator and the second pulse generator.

(3)

The signal generation apparatus according to (1) or (2) above, in which inversion timings of the phase of the signal to be generated by the first pulse generator and the signal to be generated by the second pulse generator are synchronized with each other.

(4)

The signal generation apparatus according to any one of (1) to (3) above, in which each of the first pulse generator and the second pulse generator includes:

a first counter configured to determine a phase of the pulse to be outputted and used for distance measurement of the distance measurement target using an input signal; and a second counter configured to determine a frequency of the pulse using the input signal.

(5)

The signal generation apparatus according to (4) above, in which a setting of the phase to the first pulse generator and a setting of the phase to the second pulse generator are settings different from each other.

(6)

The signal generation apparatus according to any one of (1) to (5) above, further including:

a signal selection section configured to select and output a duty of a signal to be outputted from the first pulse generator from between a first duty and a second duty different from the first duty.

(7)

The signal generation apparatus according to (6) above, in which the first duty is fixed and the second duty is variable.

(8)

The signal generation apparatus according to (6) or (7) above, in which the first pulse generator includes a main pulse generator and a sub pulse generator, the signal of the first duty is a signal generated by the main pulse generator, and the signal of the second duty is generated from the signal generated by the main pulse generator and the signal generated by the sub pulse generator.

(9)

The signal generation apparatus according to any one of (1) to (8) above, in which the signal generation apparatus is used in a distance measurement sensor of an indirect type.

REFERENCE SIGNS LIST

201: Distance image sensor
202: Optical system
203: Sensor chip
204: Image processing circuit
205: Monitor
206: Memory
211: Light source apparatus
300: Pulse generator
310: Counter
320: Flip-flop
330: And gate
340: Counter
350: PLL
352: Light source driver
354: Light source
355: Inverter
356: Pixel modulation driver
358: Pixel

The invention claimed is:

1. A signal generation apparatus comprising:
a first pulse generator circuit configured to generate a pulse supplied to a light source that irradiates light upon a distance measurement target;
a second pulse generator circuit configured to generate a pulse supplied to a pixel that receives the light reflected by the distance measurement target; and
a signal generation circuit configured to generate a pseudo-random signal for inverting or not inverting, according to a state of the pseudo-random signal, a phase of signals generated by the first pulse generator circuit and the second pulse generator circuit.

2. The signal generation apparatus according to claim 1, further comprising:
a detection circuit configured to detect a transition of the state of the pseudo-random signal, wherein
when the detection circuit detects a transition of the state of the pseudo-random signal, the detection circuit outputs a signal for inverting the phase of the signals generated by the first pulse generator circuit and the second pulse generator circuit.

3. The signal generation apparatus according to claim 1, wherein
inversion timings of the phase of the signal generated by the first pulse generator circuit and the signal generated by the second pulse generator circuit are synchronized with each other.

4. The signal generation apparatus according to claim 1, wherein
each of the first pulse generator circuit and the second pulse generator circuit includes: a first counter configured to determine a phase of the pulse outputted and used for distance measurement of the distance measurement target using an input signal; and a second counter configured to determine a frequency of the pulse using the input signal.

5. The signal generation apparatus according to claim 1, wherein
a setting of the phase to the first pulse generator circuit and a setting of the phase to the second pulse generator circuit are different from each other.

6. The signal generation apparatus according to claim 1, further comprising:
a signal selection circuit configured to select and output a duty of a signal outputted from the first pulse generator circuit from between a first duty and a second duty different from the first duty.

7. The signal generation apparatus according to claim 6, wherein
the first duty is fixed and the second duty is variable.

8. The signal generation apparatus according to claim 6, wherein
the first pulse generator circuit includes a main pulse generator and a sub pulse generator,
the signal of the first duty is generated by the main pulse generator, and
the signal of the second duty is generated from the signal generated by the main pulse generator and the signal generated by the sub pulse generator.

9. The signal generation apparatus according to claim 1, wherein
the signal generation apparatus is used in a distance measurement sensor of an indirect type.

* * * * *